(12) United States Patent
Zharov et al.

(10) Patent No.: US 11,571,255 B2
(45) Date of Patent: Feb. 7, 2023

(54) DEVICE AND METHOD FOR IN VIVO DETECTION OF CLOTS WITHIN CIRCULATORY VESSELS

(71) Applicant: Bioventures, LLC, Little Rock, AR (US)

(72) Inventors: Vladimir Pavlovich Zharov, Little Rock, AR (US); Ekaterina Galanzha, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 0 days.

(21) Appl. No.: 17/496,995

(22) Filed: Oct. 8, 2021

(65) Prior Publication Data

US 2022/0125514 A1  Apr. 28, 2022

Related U.S. Application Data

(60) Continuation of application No. 15/240,712, filed on Aug. 18, 2016, now Pat. No. 11,154,360, which is a
(Continued)

(51) Int. Cl.
*A61B 5/00* (2006.01)
*A61B 5/02* (2006.01)
(Continued)

(52) U.S. Cl.
CPC .......... *A61B 18/245* (2013.01); *A61B 5/0059* (2013.01); *A61B 5/0095* (2013.01);
(Continued)

(58) Field of Classification Search
CPC ................ A61B 5/0093; A61B 5/0095; G01N 15/14–1484; G01N 2015/1402–1497
See application file for complete search history.

(56) References Cited

U.S. PATENT DOCUMENTS

| | | | |
|---|---|---|---|
| 4,333,474 A | 6/1982 | Nigam | |
| 5,972,721 A | 10/1999 | Bruno et al. | |

(Continued)

FOREIGN PATENT DOCUMENTS

| | | |
|---|---|---|
| DE | 10343442 A1 | 4/2005 |
| WO | 2006049570 A2 | 5/2006 |

(Continued)

OTHER PUBLICATIONS

Zharov, V.P. et al. "In Vivo Photothermal Flow Cytometry: Imaging and Detection of Individual Cells in Blood and Lymph Flow". Journal of Cellular Biochemistry 97:916-932 (2006) (Year: 2006).*

(Continued)

*Primary Examiner* — Keith M Raymond
*Assistant Examiner* — Milton Truong
(74) *Attorney, Agent, or Firm* — Polsinelli PC

(57) ABSTRACT

A device and method of using the device to detect the presence and composition of clots and other target objects in a circulatory vessel of a living subject is described. In particular, devices and methods of detecting the presence and composition of clots and other target objects in a circulatory vessel of a living subject using in vivo photoacoustic flow cytometry techniques is described.

17 Claims, 19 Drawing Sheets

Related U.S. Application Data division of application No. 13/253,767, filed on Oct. 5, 2011, now Pat. No. 9,451,884, which is a continuation-in-part of application No. 12/945,576, filed on Nov. 12, 2010, now Pat. No. 9,144,383, which is a continuation-in-part of application No. 12/334,217, filed on Dec. 12, 2008, now abandoned.

(60) Provisional application No. 61/013,543, filed on Dec. 13, 2007.

(51) Int. Cl.
| | |
|---|---|
| A61B 18/24 | (2006.01) |
| A61B 8/06 | (2006.01) |
| A61B 8/08 | (2006.01) |
| A61K 49/22 | (2006.01) |
| B03C 1/28 | (2006.01) |
| B03C 1/30 | (2006.01) |
| G01N 21/17 | (2006.01) |
| G01N 29/24 | (2006.01) |
| G01N 29/44 | (2006.01) |
| A61B 5/145 | (2006.01) |
| A61B 5/1495 | (2006.01) |
| A61B 18/18 | (2006.01) |
| A61B 18/20 | (2006.01) |
| G01N 15/14 | (2006.01) |
| A61B 18/00 | (2006.01) |

(52) U.S. Cl.
CPC ........ *A61B 5/02007* (2013.01); *A61B 5/1495* (2013.01); *A61B 5/14535* (2013.01); *A61B 5/412* (2013.01); *A61B 5/415* (2013.01); *A61B 5/416* (2013.01); *A61B 5/418* (2013.01); *A61B 5/4839* (2013.01); *A61B 5/7282* (2013.01); *A61B 5/742* (2013.01); *A61B 5/7405* (2013.01); *A61B 5/746* (2013.01); *A61B 5/7455* (2013.01); *A61B 8/06* (2013.01); *A61B 8/481* (2013.01); *A61K 49/22* (2013.01); *B03C 1/288* (2013.01); *B03C 1/30* (2013.01); *G01N 21/1702* (2013.01); *G01N 29/2418* (2013.01); *G01N 29/4427* (2013.01); *A61B 8/08* (2013.01); *A61B 18/1815* (2013.01); *A61B 18/20* (2013.01); *A61B 2018/0041* (2013.01); *A61B 2018/0088* (2013.01); *A61B 2018/00577* (2013.01); *B03C 2201/06* (2013.01); *B03C 2201/26* (2013.01); *G01N 15/147* (2013.01); *G01N 15/1425* (2013.01); *G01N 15/1434* (2013.01); *G01N 2015/1477* (2013.01); *G01N 2201/0221* (2013.01)

(56) References Cited

U.S. PATENT DOCUMENTS

| | | | |
|---|---|---|---|
| 6,368,318 | B1 | 4/2002 | Visuri et al. |
| 6,428,531 | B1 | 8/2002 | Visuri et al. |
| 6,466,806 | B1 | 10/2002 | Geva et al. |
| 6,514,203 | B2 | 2/2003 | Bukshpan |
| 6,530,944 | B2 | 3/2003 | West et al. |
| 6,710,871 | B1 | 3/2004 | Goix |
| 6,833,540 | B2 | 12/2004 | MacKenzie et al. |
| 6,846,288 | B2 | 1/2005 | Nagar et al. |
| 7,220,385 | B2 | 5/2007 | Blecka et al. |
| 7,500,953 | B2 | 3/2009 | Oraevsky et al. |
| 9,144,383 | B2 | 9/2015 | Zharov |
| 9,217,703 | B2 | 12/2015 | Zharov |
| 9,451,884 | B2 | 9/2016 | Zharov et al. |
| 11,154,360 | B2 | 10/2021 | Zharov |
| 11,259,704 | B2 | 3/2022 | Zharov |
| 2002/0099283 | A1 | 7/2002 | Christ et al. |
| 2003/0216663 | A1 | 11/2003 | Jersey-Willuhn et al. |
| 2004/0039379 | A1 | 2/2004 | Viator et al. |
| 2004/0188602 | A1 | 9/2004 | Chinn et al. |
| 2005/0004458 | A1 | 1/2005 | Kanayama et al. |
| 2005/0124869 | A1 | 6/2005 | Hefti et al. |
| 2005/0175540 | A1 | 8/2005 | Oraevsky et al. |
| 2006/0078949 | A1 | 4/2006 | Offer et al. |
| 2006/0122583 | A1 | 6/2006 | Pesach et al. |
| 2007/0015978 | A1 | 1/2007 | Kanayama et al. |
| 2007/0015992 | A1 | 1/2007 | Filkins et al. |
| 2007/0121697 | A1 | 5/2007 | Burgholzer et al. |
| 2007/0213613 | A1 | 9/2007 | Ishida et al. |
| 2007/0232940 | A1* | 10/2007 | Fine .............. A61B 5/1455 600/479 |
| 2007/0269345 | A1 | 11/2007 | Schilffarth et al. |
| 2007/0292495 | A1 | 12/2007 | Ludwig et al. |
| 2008/0149566 | A1 | 6/2008 | Messersmith et al. |
| 2008/0160090 | A1 | 7/2008 | Oraevsky et al. |
| 2008/0269847 | A1 | 10/2008 | Nemenov |
| 2008/0269849 | A1 | 10/2008 | Lewis |
| 2009/0093713 | A1 | 4/2009 | Hyde et al. |
| 2009/0156932 | A1 | 6/2009 | Zharov |
| 2009/0227997 | A1 | 9/2009 | Wang et al. |
| 2009/0292195 | A1 | 11/2009 | Boydon et al. |
| 2009/0326614 | A1 | 12/2009 | El-Sayed et al. |
| 2010/0278923 | A1 | 11/2010 | Chen et al. |
| 2011/0105867 | A1 | 5/2011 | Schultz et al. |
| 2011/0117028 | A1 | 5/2011 | Zharov |
| 2011/0134426 | A1 | 6/2011 | Kaduchak et al. |
| 2011/0218140 | A1 | 9/2011 | Gonsalves et al. |
| 2011/0306865 | A1 | 12/2011 | Thornton et al. |
| 2012/0022360 | A1 | 1/2012 | Kemp |
| 2012/0065490 | A1 | 3/2012 | Zharov et al. |
| 2012/0179227 | A1 | 7/2012 | Schomacker et al. |
| 2012/0202278 | A1 | 8/2012 | Wagner et al. |
| 2012/0237605 | A1 | 9/2012 | Messersmith et al. |
| 2013/0030307 | A1 | 1/2013 | Rajan et al. |
| 2013/0060122 | A1 | 3/2013 | Zharov |
| 2013/0123604 | A1 | 5/2013 | Oyama |
| 2015/0065685 | A1 | 3/2015 | Arany et al. |
| 2015/0150463 | A1 | 6/2015 | Smeltzer et al. |
| 2015/0282716 | A1 | 10/2015 | Smeltzer et al. |
| 2015/0335741 | A1 | 11/2015 | Smeltzer et al. |
| 2015/0351640 | A1 | 12/2015 | Zharov |
| 2016/0058297 | A1 | 3/2016 | Zharov |
| 2016/0354150 | A1 | 12/2016 | Zharov |
| 2018/0000351 | A1 | 1/2018 | Zharov |

FOREIGN PATENT DOCUMENTS

| | | |
|---|---|---|
| WO | 2013067419 A1 | 5/2013 |
| WO | 2014052449 A1 | 4/2014 |
| WO | 2016109831 A1 | 7/2016 |
| WO | 2016196791 A1 | 12/2016 |

OTHER PUBLICATIONS

Galanzha, E.I. et al. "Advances in small animal mesentery models for in vivo flow cytometry, dynamic microscopy, and drug screening". World J Gastroenterol 13(2): 192-218 (2007) (Year: 2007).*

Aguirre-Ghiso, J., "On the theory of self-seeding: implications for metastasis progression in humans," Breast Cancer Res., 2010, pp. 1-2, vol. 12, No. 304.

Alexander, J., "The Normal Blood Clotting Time in the Light of Experience with the 'Two-syringe' Technique," J. Clin. Pathol., 1955, pp. 227-228, vol. 8.

Alix-Panabieres, C. et al., "Circulating Tumor Cells and Circulating Tumor DNA," Annu. Rev. Med., 2012, pp. 199-215, vol. 63.

Alix-Panabieres, C. et al., "Circulating Tumor Cells: Liquid Biopsy of Cancer," Clin. Chem., 2013, pp. 110-118, vol. 59, No. 1.

Allan, A. et al., "Detection and Quantification of Circulating Tumor Cells in Mouse Models of Human Breast Cancer Using Immunomagnetic Enrichment and Multiparameter Flow Cytometry," Cytometry Part A, May 2005, pp. 4-14, vol. 65A, No. 1, Wiley-Liss, Inc.

(56) References Cited

OTHER PUBLICATIONS

Alunni-Fabbroni, M. et al., "Circulating tumour cells in clinical practice: Methods of detection and possible characterization," Methods, 2010, pp. 289-297, vol. 50, Elsevier Inc.

Ara, G. et al., "Irradiation of Pigmented Melanoma Cells With High Intensity Pulsed Radiation Generates Acoustic Waves and Kills Cell," Lasers in Surgery and Medicine, 1990, pp. 52-59, vol. 10, No. 1.

Autebert, J. et al., "Microfluidic: an innovative tool for efficient cell sorting," Methods, 2012, pp. 297-307, vol. 57, No. 3, Elsevier.

Baeuerle, P. et al., "EpCAM (CD326) finding its own role in cancer," Br. J. Cancer, Feb. 12, 2007, pp. 417-423, vol. 96.

Berciaud, S. et al., "Photothermal Heterodyne Imaging of Individual Nonfluorescent Nanoclusters and Nanocrystals," Phys. Rev. Lett., Dec. 17, 2004, p. 257402-1 to 257402-4, vol. 93.

Bhattacharyya, B. et al., "Gold nanoparticle-mediated detection of circulating cancer cells," NIH Public Access Author Manuscript,Mar. 1, 2013, pp. 1-18, published in final form as Clin. Lab. Med., Mar. 2012, pp. 89-101, vol. 32, No. 1.

Bhattacharyya, K. et al., "Detection, isolation, and capture of circulating breast cancer cells with photoacoustic flow cytometry," Proc. SPIE, 2013, 9 pgs., vol. 8570A.

Biris, A. et al., "In vivo Raman flow cytometry for real-time detection of carbon nanotube kinetics in lymph, blood, and tissues," J. Biomed. Opt., Mar./Apr. 2009, pp. 021006-1-021006-10, vol. 14, No. 2.

Birtill, D. et al., "Photoacoustic Spectroscopy," Central Laser Facility Annual Report, 2010-2011, Laser for Science Facility-Biology, 25 pgs.

Blab, G. et al., "Optical readout of gold nanoparticle-based DNA microarrays without silver enhancement," Biophys. J. Biophys. Lett., 2006, pp. L13-L15, vol. 90, No. 1.

Bland, J. et al., "Statistical methods for assessing agreement between two methods of clinical measurement," Lancet, Feb. 8, 1986, pp. 307-310, vol. 1.

Boutrus, S. et al., "Portable two-color in vivo flow cytometer for real-time detection of fluorescently-labeled circulating cells," NIH Public Access Author Manuscript, Dec. 28, 2009, pp. 1-8, published in final edited form as J. Biomed. Opt., 2007, p. 020507, vol. 12, No. 2.

Brusnichkin, A. et al., "Ultrasensitive label-free photothermal imaging, spectral identification, and quantification of cytochrome c in mitochondria, live cells, and solutions," NIH Public Access Author Manuscript, May 11, 2012, pp. 1-28, Published in final edited form as J. Biophotonics, Dec. 2010, pp. 791-806, vol. 3, No. 12.

Budd, G. et al., "Circulating Tumor Cells versus Imaging-Predicting Overall Survival in Metastatic Breast Cancer," Clin. Cancer Res., Nov. 1, 2006, pp. 6403-6409, vol. 12, No. 21.

Chaffer, C. et al., "A Perspective on Cancer Cell Metastasis," Sci., Mar. 25, 2011, pp. 1559-1564, vol. 25, No. 331.

Chen, Y. et al., "Platelet CD62P Expression and Microparticle in Murine Acquired Immune Deficiency Syndrome and Chronic Ethanol Consumption," Alcohol Alcoholism, Jan. 1, 2003, pp. 25-30, vol. 38, No. 1.

Chitnis, P. et al., "Feasibility of optoacoustic visualization of high-intensity focused ultrasound-induced thermal lesions in live tissue," J. Biomed Opt., Mar./Apr. 2010, pp. 021313-1 to 021313-5, vol. 15, No. 2.

Chu, J. et al., "The Role of Cancer Stem Cells in the Organ Tropism of Breast Cancer Metastasis: A Mechanistic Balance between the "Seed" and the "Soil"?," Int. J. Breast Cancer, 2012, pp. 1-12, vol. 2012, Article ID 209748, Hindawi Publishing Corporation.

Cristofanilli, M. et al., "Circulating tumor cells, disease progression, and survival in metastatic breast cancer," N. Engl. J. Med., 2004, pp. 781-791, vol. 351.

Cristofanilli, M. et al., "Circulating Tumor Cells: A Novel Prognostic Factor for Newly Diagnosed Metastatic Breast Cancer," J. Clin. Oncol., Mar. 1, 2005, pp. 1420-1430, vol. 23, No. 7.

Debruyn, M. et al., "Melanoma-associated Chondroitin Sulfate Proteoglycan (MCSP)-targeted delivery of soluble TRAIL potently inhibits melanoma outgrowth in vitro and in vivo," Mol. Cancer, 2010, pp. 1-14, vol. 9, No. 301.

Degiorgi, V. et al., "Application of a Filtration- and Isolation-by-Size Technique for the Detection of Circulating Tumor Cells in Cutaneous Melanoma," J. Invest. Dermatol., 2010, pp. 2440-2447, vol. 130.

De La Zerda, A. et al., "Advanced contrast nanoagents for photoacoustic molecular imaging, cytometry, blood test and photothermal theranostics," Contrast Media Mol. Imaging, 2011, pp. 346-369, vol. 6, John Wiley & Sons, Ltd.

Dick, J., "Breast cancer stem cells revealed," PNAS, Apr. 1, 2003, pp. 3547-3549, vol. 100, No. 7.

European Extended Search Report dated Aug. 10, 2018 from related European Patent Application No. 15876378.9; 13 pgs.

Freeman, J. et al., "Evaluation of a multi-marker immunomagnetic enrichment assay for the quantification of circulating melanoma cells," J. Transl. Med., 2012, pp. 1-9, vol. 10, No. 192.

Fukunaga-Kalabis, M. et al., "Beyond ABC: Another Mechanism of Drug Resistance in Melanoma Side Population," J. Invest. Dermatol., 2012, pp. 2317-2319, vol. 132.

Gaiduk, A. et al., "Room-Temperature Detection of a Single Molecule's Absorption by Photothermal Contrast," Sci., Oct. 15, 2010, pp. 353-356, vol. 330.

Galanzha, E. et al., "In vivo integrated flow image cytometry and lymph/blood vessels dynamic microscopy," J. Biomed. Opt., Sep /Oct. 2005, pp. 054018-1-054018-8, vol. 10, No. 5.

Galanzha, E. et al., "Advances in small animal mesentery models for in vivo flow cytometry, dynamic microscopy, and drug screening," World J. Gastroenterol., Jan. 14, 2007, pp. 192-218, vol. 13, No. 2, The WJG Press.

Galanzha, E. et al., "In vivo multispectral, multiparameter, photoacoustic lymph flow cytometry with natural cell focusing, label-free detection and multicolor nanoparticle probes," Cytometry A, 2008, pp. 884-894, vol. 73A, No. 10, with NIH Public Access Author Manuscript, Oct. 1, 2009, pp. 1-19.

Galanzha, E. et al., "In vivo, Noninvasive, Label-Free Detection and Eradication of Circulating Metastatic Melanoma Cells Using Two-Color Photoacoustic Flow Cytometry with a Diode Laser," Cancer Res., 2009, pp. 7926-7934, vol. 69, No. 20.

Galanzha, E. et al., "In vivo fiber-based multicolor photoacoustic detection and photothermal purging of metastasis in sentinel lymph nodes targeted by nanoparticles," NIH Public Access Author Manuscript, May 24, 2013, pp. 1-17, published in final edited form as J. Biophoton., Sep. 2009, pp. 528-539, vol. 2.

Galanzha, E. et al., "Nanotechnology-based molecular photoacoustic and photothermal flow cytometry platform for in-vivo detection and killing of circulating cancer stem cells," J. Biophoton., 2009, pp. 725-735, vol. 2, No. 12.

Galanzha, E. et al., "In vivo magnetic enrichment and multiplex photoacoustic detection of circulating tumour cells," NIH Public Access Author Manuscript, May 24, 2013, pp. 1-13, published in final edited form as Nat. Nanotechnol., Dec. 2009, pp. 855-860, vol. 4, No. 12.

Galanzha, E. et al., "In Vivo Photoacoustic and Photothermal Cytometry for Monitoring Multiple Blood Rheology Parameters," Cytometry Part A, Oct. 2011, pp. 746-757, vol. 79, No. 10.

Galanzha, E. et al., "In Vivo Flow Cytometry of Circulating Clots Using Negative Photothermal and Photoacoustic Contrasts," Cytometry Part A, Oct. 2011, pp. 814-824, vol. 79A, No. 10, with Corrigendum, Cytometry Part A, 2011, pp. 1024, vol. 79A, No. 12.

Galanzha, E. et al., "Photoacoustic flow cytometry," Methods, Jul. 2012, pp. 280-296, vol. 57, No. 3, with HHS Public Access Author Manuscript, Mar. 19, 2016, pp. 1-44, Academic Press.

Galanzha, E. et al., "In vivo Magnetic Enrichment, Photoacoustic Diagnosis, and Photothermal Purging of Infected Blood Using Multifunctional Gold and Magnetic Nanoparticles," PLoS One, Sep. 2012, pp. 1-14, vol. 7, No. 9, e45557.

Galanzha, E. et al., "Circulating tumor cell detection and capturing using photoacoustic flow cytometry in vivo and ex vivo," Cancers, Manuscript, 2013, pp. 1-45, vol. 5.

(56) References Cited

OTHER PUBLICATIONS

Galanzha, E. et al., "Photoacoustic and photothermal cytometry using photoswitchable proteins and nanoparticles with ultrasharp resonances" J. Biophoton., Jan. 2015, pp. 81-93, vol. 8, No. 1-2, Wiley-VCH Verlag GmbH & Co. KGaA, Weinheim.
Garrett, T et al., "Bacterial adhesion and biofilms on surfaces," Progress in Natural Science, 2008, pp. 1049-1056, vol. 18, Elsevier.
Givan, A., "Flow Cytometry. An Introduction," Methods in Molecular Biology, Flow Cytometry Protocols, Second Edition, 2004, pp. 1-31, vol. 263, Humana Press.
Goddard, G. et al., "Ultrasonic Particle-Concentration for Sheathless Focusing of Particles for Analysis in a Flow Cytometer," Cytometry Part A, 2006, pp. 66-74, vol. 69A.
Gutierrez-Juarez, G. et al., "Optical Photoacoustic Detection of Circulating Melanoma Cells In Vitro," Int. J. Thermophys , 2010, pp. 784-792, vol. 31, Springer Science+Business Media, LLC.
Stott, S. et al., "Isolation of circulating tumor cells using a microvertex-generating herringbone-chip," PNAS, Oct. 26, 2010, pp. 18392-18397, vol. 107, No. 43.
Tamaki, E. et al., "Single-Cell Analysis by a Scanning Thermal Lens Microscope with a Microchip: Direct Monitoring of Cytochrome c Distribution during Apoptosis Process," Anal. Chem., Apr. 1, 2002, pp. 1560-1564, vol. 74, No. 7.
Tanev, S. et al., "Flow Cytometry with Gold Nanoparticles and their Clusters as scattering Contrast Agents: FDTD Simulation of Light-Cell Interaction," NIH Public Access Author Manuscript, Sep. 1, 2010, pp. 1-24, published in final edited form as J. Biophotonics, Sep. 2009, pp. 505-520, vol. 2, Nos. 8-9.
Tibbe, A. et al., "Statistical Considerations for Enumeration of Circulating Tumor Cells," Cytometry Part A, 2007, pp. 154-162, vol. 71A.
Tokeshi, M. et al., "Determination of Subyoctomole Amounts of Nonfluorescent Molecules Using a Thermal Lens Microscope: Subsingle-Molecule Determination," Anal. Chem., May 1, 2001, pp. 2112-2116, vol. 73, No. 9.
Tuchin, V. et al., "Towards in vivo flow cytometry," HHS Public Access Author Manuscript, Mar. 2, 2016, pp. 1-4, published in final edited form as J. Biophotonics, Sep. 2009, pp. 457-458, vol. 2, No. 0.
Tuchin, V. et al., "In Vivo Flow Cytometry: A Horizon of Opportunities," Cytometry Part A, 2011, pp. 737-745, vol. 79A.
Ulmer, A. et al., "Detecting Circulating Melanoma Cells," J. Invest. Dermatol., 2011, pp. 1774-1775, vol. 131.
Van Dijk, M. et al., "Absorption and scattering microscopy of single metal nanoparticles," Phys. Chem. Chem. Phys., 2006, pp. 3486-3495, vol. 8.
Wang, L., "Multiscale photoacoustic microscopy and computed tomography," NIH Public Access Author Manuscript, Aug. 29, 2010, pp. 1-16, published in final edited form as Nat. Photonics, Aug. 29, 2009, pp. 503-509, vol. 3, No. 9.
Wang, Y. et al., "Fiber-laser-based photoacoustic microscopy and melanoma cell detection," J. Biomed. Opt., Jan. 2011, pp. 011014-1 to 011014-4, vol. 16, No. 1.
Wang, L. et al., "Photoacoustic Tomography: In Vivo Imaging from Organelles to Organs," Sci., Mar. 23, 2012, pp. 1458-1462, vol. 335.
Wang, Z. et al., "CD146, a multi-functional molecule beyond adhesion," Cancer Lett., 2013, pp. 150-162, vol. 330.
Wei, X. et al., "Selective Uptake of Indocyanine Green by Reticulocytes in Circulation," Invest. Ophthalmol. Vis. Sci., Oct. 2003, pp. 4489-4496, vol. 44, No. 10.
Weight, R. et al., "Photoacoustic detection of metastatic melanoma cells in the human circulatory system," Opt. Lett., Oct. 15, 2006, pp. 2998-3000, vol. 31, No. 20, Optical Society of America.
Wicha, M. et al., "Circulating Tumor Cells: Not All Detected Cells Are Bad and Not All Bad Cells Are Detected," J. Clin. Oncol., 2011, pp. 1508-1511, vol. 29.
Williams, S., "Circulating Tumor Cells," PNAS, Mar. 26, 2013, p. 4861, vol. 110, No. 13.
Witzig, T. et al., "Detection of Circulating Cytokeratin-positive Cells in the Blood of Breast Cancer Patients Using Immunomagnetic Enrichment and Digital Microscopy," Clin. Cancer Res., May 2002, pp. 1085-1091, vol. 8.
Xu, M. et al., "Photoacoustic imaging in biomedicine," Rev. Sci. Instrum., 2006, pp. 041101-1 to 041101-22, vol. 77.
Xu, X. et al., "Circulating Tumor Cells and Melanoma Progression," J. Invest. Dermatol., 2010, pp. 2349-2351, vol. 130.
Yang, J. et al., "Melanoma Proteoglycan Modifies Gene Expression to Stimulate Tumor Cell Motility, Growth, and Epithelial-to-Mesenchymal Transition," Cancer Res., 2009, pp. 7538-7547, vol. 69, No. 19.
Yu, M. et al., "Circulating tumor cells: approaches to isolation and characterization," J. Cell Biol., 2011, pp. 373-382, vol. 192, No. 3.
Yu, M. et al., "Circulating Breast Tumor Cells Exhibit Dynamic Changes in Epithelial and Mesenchymal Composition," Sci., Feb. 1, 2013, pp. 580-584, vol. 339.
Zharov, V. et al., "Photothermal detection of local thermal effects during selective nanophotothermolysis," Appl. Phys. Lett., Dec. 15, 2003, pp. 1-3, vol. 83, No. 24.
Zharov, V. et al., "Infrared imaging of subcutaneous veins," Lasers Surg. Med., Jan. 2004, pp. 56-61, vol. 34, No. 1, Wiley-Liss, Inc.
Zharov, V. et al., "Photothermal Imaging of Nanoparticles and Cells," IEEE Journal of Selected Topics in Quantum Electronics, Jul./Aug. 2005, pp. 733-751, vol. 11, No. 4.
Zharov, V. et al., "Microbubbles-overlapping mode for laser killing of cancer cells with absorbing nanoparticle clusters," J. Physics D: Appl. Phys., 2005, pp. 2571-2581, vol. 38.
Zharov, V. et al., "Photoacoustic tweezers with a pulsed laser source: theory and experiments," J. Physics D: Appl. Phys., 2005, pp. 1-13, vol. 38, IOP Publishing Ltd, United Kingdom.
Zharov, V. et al., "Photothermal image flow cytometry in vivo," Opt. Lett., Mar. 15, 2005, pp. 628-630, vol. 30, No. 6.
Zharov, V. et al., "In Vivo Photothermal Flow Cytometry: Imaging and Detection of Individual Cells in Blood and Lymph Flow," J. Cellular Biochem., 2006, pp. 916-932, vol. 97, No. 5.
Zharov, V. et al., "In vivo photoacoustic flow cytometry for monitoring of circulating single cancer cells and contrast agents," Opt. Lett., Dec. 15, 2006, pp. 3623-3625, vol. 31, No. 24.
Zharov, V. et al., "Photothermal Flow Cytometry In Vitro for Detection and Imaging of Individual Moving Cells," Cytometry Part A, 2007, pp. 191-206, vol. 71 A.
Zharov, V. et al., "Confocal photothermal flow cytometry in vivo," Proc. SPIE, Apr. 2005, pp. 15-26, vol. 5697.
Zharov, V. et al., "Integrated photothermal flow cytometry in vivo," J. Biomed. Opt., Sep./Oct. 2005, pp. 051502-1-051502-13, vol. 10, No. 5.
Zharov, V. et al., "Nanocluster model of photothermal assay: application for high-sensitive monitoring of nicotine-induced changes in metabolism, apoptosis, and necrosis at a cellular level," J. Biomed. Opt., Jul./Aug. 2005, pp. 044011-1-044011-15, vol. 10, No. 4.
Zharov, V. et al., "Self-assembling nanoclusters in living systems: application for integrated photothermal nanodiagnostics and nanotherapy," J. Nanomed., Dec. 2005, pp. 326-345, vol. 1, No. 4.
Zharov, V. et al., "Synergistic enhancement of selective nanophotothermolysis with gold nanoclusters: Potential for cancer therapy," Laser Surg. Med., 2005, pp. 219-226, vol. 37, No. 3.
Zharov, V. et al., "In vivo high-speed imaging of individual cells in fast blood flow," J. Biomed. Opt., Sep./Oct. 2006, pp. 054034-1-054034-4, vol. 11, No. 5.
Zharov, V. et al., "Photothermal Nanotherapeutics and Nanodiagnostics for Selective Killing of Bacteria Targeted with Gold Nanoparticles," Biophys. J., Jan. 2006, pp. 619-627, vol. 90, Biophysical Society.
Zharov, V. et al., "Photoacoustic flow cytometry: principle and application for real-time detection of circulating nanoparticles, pathogens, and contrast dyes in vivo," J. Biomed. Opt., Sep. 1, 2007, pp. 051503-1-051503-14, vol. 12, No. 5.
Zharov, V. et al., "Ultrasharp nonlinear photothermal and photoacoustic resonances and holes beyond the spectral limit," HHS Public Access Author Manuscript, Jan. 2, 2015, pp. 1-16, published in final edited form as Nat. Photonics, Feb. 2011, pp. 110-116, vol. 5, No. 2.

(56) References Cited

OTHER PUBLICATIONS

Zhe, X. et al., "Circulating tumor cells: finding the needle in the haystack," Am. J. Cancer Res., 2011, pp. 740-751, vol. No. 6.
Zheng, H. et al., "Detection of the Cancer Marker CD146 Expression in Melanoma Cells with Semiconductor Quantum Dot Label," J. Biomed. Nanotechnol., Aug. 2010, pp. 303-311, vol. 6, No. 4.
O'Brien, C. et al., "Capture of circulating tumor cells using photoacoustic flowmetry and two phase flow," J. Biomed. Opt., Jun. 2012, pp. 061221-1 to 061221-9, vol. 17, No. 6.
Office Action dated Nov. 30, 2011 from related U.S. Appl. No. 12/334,217; 12 pgs.
Office Action dated Apr. 26, 2012 from related U.S. Appl. No. 12/334,217; 10 pgs.
Office Action dated Oct. 6, 2014 from related U.S. Appl. No. 13/253,767; 18 pgs.
Office Action dated Apr. 16, 2015 from related U.S. Appl. No. 13/253,767; 17 pgs.
Office Action dated Jul. 30, 2015 from related U.S. Appl. No. 13/253,767; 16 pgs.
Office Action dated Feb. 22, 2016 from related U.S. Appl. No. 13/253,767; 7 pgs.
Office Action dated Feb. 13, 2014 from related U.S. Appl. No. 13/661,551; 11 pgs.
Office Action dated Oct. 7, 2014 from related U.S. Appl. No. 13/661,551; 10 pgs.
Office Action dated Apr. 3, 2015 from related U.S. Appl. No. 13/661,551; 11 pgs.
Office Action dated Jan. 30, 2017 from related U.S. Appl. No. 14/552,143; 14 pgs.
Office Action dated Oct. 26, 2016 from related U.S. Appl. No. 14/668,418; 11 pgs.
Office Action dated May 24, 2017 from related U.S. Appl. No. 14/668,418; 12 pgs.
Office Action dated Nov. 27, 2017 from related U.S. Appl. No. 14/728,849; 9 pgs.
Office Action dated Dec. 8, 2017 from related U.S. Appl. No. 14/668,418; 29 pgs.
Office Action dated Dec. 14, 2017 from related U.S. Appl. No. 14/552,143; 9 pgs.
Office Action dated Jul. 13, 2018 from related U.S. Appl. No. 14/728,849; 12 pgs.
Office Action dated Jul. 13, 2018 from related U.S. Appl. No. 14/552,143; 9 pgs.
Office Action dated Aug. 10, 2018 from related U.S. Appl. No. 14/668,418; 16 pgs.
Office Action dated Sep. 26, 2018 from related U.S. Appl. No. 14/754,034; 7 pgs.
Office Action dated Feb. 8, 2019 from related U.S. Appl. No. 15/240,712; 37 pgs.
Office Action dated Aug. 22, 2019 from related U.S. Appl. No. 15/240,712; 13 pgs.
Office Action dated Oct. 11, 2019 from related U.S. Appl. No. 14/939,039; 9 pgs.
Office Action dated Jun. 25, 2020 from related U.S. Appl. No. 15/240,712; 18 pgs.
Office Action dated Dec. 16, 2020 from related U.S. Appl. No. 14/939,039; 9 pgs.
Office Action dated Jan. 21, 2021 from related U.S. Appl. No. 15/240,712; pgs.
Ozkumur, E. et al., "Inertial Focusing for Tumor Antigen-Dependent and- Independent Sorting of Rare Circulating Tumor Cells," NIH Public Access Author Manuscript, Oct. 3, 2013, pp. 1-20, published in final edited form as Sci. Transl. Med., Apr. 3, 2013, pp. 179ra47, vol. 5, No. 179.
Pantel, K. et al., "Detection, clinical relevance and specific biological properties of disseminating tumour cells," Nat. Rev. Cancer, May 2008, pp. 329-340, vol. 8, Nature Publishing Group.
Pelan-Mattocks, L. et al., "Flow cytometric analysis of intracellular complexity and CD45 expression for use in rapid differentiation of leukocytes in bovine blood samples," Am. J. Vet Res., Nov. 2001, pp. 1740-1744, vol. 62, No. 11.
Perez-Gutierrez, F. et al., "Plasma Membrane Integrity and Survival of Melanoma Cells After Nanosecond Laser Pulses," Ann. Biomed. Eng., Nov. 2010, pp. 3521-3531, vol. 38, No. 11.
Piyasena, M. et al., "Multinode acoustic focusing for parallel flow cytometry," NIH Public Access Author Manuscript, Feb. 21, 2013, pp. 1-18, published in final edited form as Anal. Chem., Feb. 21, 2012, pp. 1831-1839, vol. 84, No. 4.
Prahl, S., "Optical Absorption of Hemoglobin," available at http://omlc.ogi.edu/spectra/hemoglobin, Dec. 15, 1999, 4 pgs.
Proskurnin, M. et al., "In Vivo Multispectral Photoacoustic and Photothermal Flow Cytometry with Multicolor Dyes: A Potential for Real-Time Assessment of Circulation, Dye-Cell Interaction, and Blood Volume," Cytometry Part A, 2011, pp. 834-847, vol. 79A.
Rai, R. et al., "Nanoparticles and their potential application as antimicrobials," Formatex Microbiology Series No. 3, Dec. 31, 2011, pp. 197-209, vol. 1.
Rao, C. et al., "Circulating melanoma cells and survival in metastatic melanoma," Int. J. Oncol., 2011, pp. 755-760, vol. 38.
Reggiori, G. et al., "Early alterations of red blood cell rheology in critically ill patients," Crit. Care Med., 2009, pp. 3041-3046, vol. 37, No. 12.
Riethdorf, S. et al., "Detection of Circulating Tumor Cells in Peripheral Blood of Patients with Metastatic Breast Cancer: A Validation Study of the CellSearch System," Clin. Cancer Res., Feb. 1, 2007, pp. 920-928, vol. 13, No. 3.
Sarimollaoglu, M. et al., "In vivo photoacoustic time-of-flight velocity measurement of single cells and nanoparticles," NIH Public Access Author Manuscript, Oct. 15, 2012, pp. 1-8, published in final edited form as: Opt. Lett., Oct. 15, 2011, pp. 4086-4088, vol. 36, No. 20.
Sarimollaoglu, M. et al., "Nonlinear photoacoustic signal amplification from single targets in absorption background," Photoacoustics, Article in Press, 2013, pp. 1-11, vol. 12, Elsevier.
Schmid, T. et al., "Process analysis of biofilms by photoacoustic spectroscopy," Anal. Bioanal. Chem., 2003, pp. 1124-1129, vol. 375.
Schmid, T. et al., "Photoacoustic absorption spectra of biofilms," Review of Scientific Instruments, Jan. 2003, pp. 755-757, vol. 74, No. 1.
Schmidt-Kittler, O. et al., "From latent disseminated cells to overt metastasis: Genetic analysis of systemic cancer progression," PNAS, Jun. 24, 2003, pp. 7737-7742, vol. 100. No. 13.
Setia, N. et al., "Profiling of ABC transporters ABCB5, ABCF2, and nestin-positive stem cells in nevi, in situ and invasive melanoma," Mod. Pathol., 2012, pp. 1169-1175, vol. 25.
Shao, J. et al., "Photothermal nanodrugs: potential of TNF-gold nanospheres for cancer theranostics," Nature Scientific Reports, 2013, pp. 1-9, vol. 3, No. 1293, Nature Publishing Group.
Shashkov, E. et al., "Quantum dots as multimodal photoacoustic and photothermal contrast agents," NIH Public Access Author Manuscript, Nov. 1, 2009, pp. 1-13, published in final edited form as Nano Lett., Nov. 2008, pp. 3953-3958, vol. 8, No. 11.
Shashkov, E. et al., "Photothermal and photoacoustic Raman cytometry in vitro and in vivo," Opt. Exp., Mar. 29, 2010, pp. 6929-6944, vol. 18, No. 7.
Shibue, T. et al., "Metastatic colonization: Settlement, adaptation and propagation of tumor cells in a foreign tissue environment," Semin. Cancer Biol., 2011, pp. 99-106, vol. 21, Elsevier Ltd.
Sieuwerts, A. et al., "Anti-Epithelial Cell Adhesion Molecule Antibodies and the Detection of Circulating Normal-Like Breast Tumor Cells," J. Natl. Cancer Inst., Jan. 7, 2009, pp. 61-66, vol. 101, No. 1.
Sleeman, J. et al., "Do all roads lead to Rome? Routes to metastasis development," Int. J. Cancer, 2011, pp. 2511-2526, vol. 128.
Gutierrez-Juarez, G. et al., "Detection of Melanoma Cells In Vitro Using an Optical Detector of Photoacoustic Waves," Lasers Surg. Med., 2010, pp. 274-281, vol. 42.

(56) References Cited

OTHER PUBLICATIONS

Haruna, M. et al., "Blood Volume Measurement at the Bedside Using ICG Pulse Spectrophotometry," Anesthesiology, 1998, pp. 1322-1328, vol. 89.

Ida, J. et al., "Cell surface chondroitin sulfate glycosaminoglycan in melanoma: role in the activation of pro-MMP-2 (progelatinase A)," Biochem. J., May 1, 2007, pp. 553-563, vol. 403, No. 3, Biochemical Society, Great Britain.

International Search Report and Written Opinion dated Dec. 16, 2013 from related International Patent Application No. PCT/US2013/061673; 8 pgs.

International Search Report and Written Opinion dated Mar. 17, 2016 from related International Patent Application No. PCT/US2015/068341; 8 pgs.

International Search Report and Written Opinion dated Oct. 6, 2016 from related International Patent Application No. PCT/US2016/035512; 12 pgs.

Ion, R-M. et al., "The incorporation of various porphyrins into blood cells measured via flow cytometry, absorption and emission spectroscopy," Acta Biochim. Pol., 1998, pp. 833-845, vol. 45, No. 3.

Joosse, S. et al., "Biologic Challenges in the Detection of Circulating Tumor Cells," Cancer Res., Jan. 1, 2013, pp. 8-11, vol. 73, No. 1.

Karpiouk, A. et al., "Combined Ultrasound and Photoacoustic Imaging to Age Deep Vein Thrombosis: Preliminary Studies," IEEE Ultrasonics Symposium, 2005, pp. 399-402, vol. 1.

Karpiouk, A. et al., "Combined ultrasound and photoacoustic imaging to detect and stage deep vein thrombosis: phantom and ex vivo studies," J. Biomed. Opt., Sep./Oct. 2008, pp. 054061-1 to 054061-8, vol. 13, No. 5.

Kaiser, J., "Cancer's Circulation Problem," Sci., Feb. 26, 2010, pp. 1072-1074, vol. 327.

Khlebtsov, B. et al., "Optical amplification of photothermal therapy with gold nanoparticles and nanoclusters," Nanotechnol., 2006, pp. 5167-5179, vol. 17, Institute of Physics Publishing.

Khoja, L. et al., "Biomarker utility of circulating tumor cells in metastatic cutaneous melanoma," J. Invest. Dermatol., Jun. 2013, pp. 1582-1590, vol. 133, No. 6.

Kim, Y. et al., "Subtyping Lymphocytes in Peripheral Blood by Immunoperoxidase Labeling and Light Scatter/Absorption Flow Cytometry," Clin. Chem., 1985, pp. 1481-1486, vol. 31, No. 9.

Kim, J-W. et al., "In situ fluorescence microscopy visualization and characterization of nanometer-scale carbon nanotubes labeled with 1-pyrenebutanoic acid, succinimdyl ester," Appl. Phys. Lett., 2006, pp. 213110-1 to 213110-3, vol. 88.

Kim, M. et al., "Tumor Self-Seeding by Circulating Cancer Cells," Cell, Dec. 24, 2009, pp. 1315-1326, vol. 139, Elsevier Inc.

Kim, J-W. et al., "Golden carbon nanotubes as multimodal photoacoustic and photothermal high-contrast molecular agents," NIH Public Access Author Manuscript, May 24, 2013, pp. 1-15, published in final edited form as Nat. Nanotechnol., Oct. 2009, pp. 688-694, vol. 4, No. 10.

Kim, C. et al., "Deeply penetrating in vivo photoacoustic imaging using a clinical ultrasound array system," Biomed. Opt. Express, Aug. 2010, pp. 278-284, vol. 1, No. 1.

Kim, J-W. et al., "Nanotheranostics of Circulating Tumor Cells, Infections and Other Pathological Factors In Vivo," NIH Public Access Author Manuscript, Mar. 4, 2014, pp. 1-37, published in final edited form as Mol. Pharm., Mar. 4, 2013, pp. 813-830, vol. 10, No. 3.

Krishnamurthy, S., "The Emerging Role of Circulating Tumor Cells in Breast Cancer," Cancer Cytopathol., Jun. 25, 2012, pp. 161-166, vol. 120.

Lai, C. et al., "CD133+ Melanoma Subpopulations Contribute to Perivascular Niche Morphogenesis and Tumorigenicity Through Vasculogenic Mimicry," Cancer Res., 2012, pp. 5111-5118, vol. 72, No. 19.

Langley, R. et al., "Tumor Cell-Organ Microenvironment Interactions in the Pathogenesis of Cancer Metastasis," Endocr. Rev., 2007, pp. 297-321, vol. 28, No. 3.

Lapotko, D. et al., "Photothermal image cytometry of human neutrophils," Cytometry, 1996, pp. 198-203, vol. 24, Wiley-Liss, Inc.

Lapotko, D. et al., "Spectral Evaluation of Laser-Induced Cell Damage With Photothermal Microscopy," Lasers in Surgery and Medicine, 2005, pp. 22-30, vol. 36, No. 1, Wiley-Liss, Inc.

Lasne, D. et al., "Label-free optical imaging of mitochondria in live cells," Opt. Exp., Oct. 17, 2007, pp. 14184-14193, vol. 15, No. 21.

Letfullin, R. et al., "Laser-induced explosion of gold nanoparticles: potential role for nanophotothermolysis of cancer," Nanomed., 2006, pp. 473-480, vol. 1, No. 4, Future Medicine Ltd.

Leung, C. et al., "Tumor Self-Seeding: Bidirectional Flow of Tumor Cells," Cell, Dec. 24, 2009, pp. 1226-1228, vol. 139, Elsevier Inc.

Li, C. et al., "Preparation and characterization of flexible nanoliposomes loaded with daptomycin, a novel antibiotic, for topical skin therapy," International Journal of Nanomedicine, Mar. 24, 2013, pp. 1285-1292, vol. 8.

Lianidou, E., "Circulating Tumor Cells—New Challenges Ahead," Clin. Chem., 2012, pp. 805-807, vol. 58, No. 5.

Liao, H. et al., "Gold Nanorod Bioconjugates," Chem. Mater., 2005, pp. 4636-4641, vol. 17, No. 18, American Chemical Society.

Liu, Z. et al., "Negative enrichment by immunomagnetic nanobeads for unbiased characterization of circulating tumor cells from peripheral blood of cancer patients," J. Transl. Med., 2011, pp. 1-8, vol. 9, No. 70.

Ma, J. et al., "Isolation of tumorigenic circulating melanoma cells," Biochem. Biophys. Res. Commun., 2010, pp. 711-717, vol. 402, No. 4, Elsevier Inc.

Maheswaran, S. et al., "Circulating Tumor Cells: a window into cancer biology and metastasis," HHMI Author Manuscript, pp. 1-6, Published as: Curr. Opin. Genet. Dev., Feb. 2010, pp. 96-99, vol. 20, No. 1.

Mallidi, S. et al., "Photoacoustic imaging in cancer detection, diagnosis, and treatment guidance," Trends Biotechnol., May 2011, pp. 213-221, vol. 29, No. 5.

Menyaev, Y. et al., "Resolution of photoacoustic flow cytometry," Optical Society of America, 2013, 16 pgs.

Menyaev, Y. et al., "Preclinical photoacoustic models: application for ultrasensitive single cell malaria diagnosis in large vein and artery," Biomed. Opt. Express, Sep. 1, 2016, pp. 3643-3658, vol. 7, No. 9.

Molino, A. et al., "A Comparative Analysis of Three Different Techniques for the Detection of Cancer Cells in Bone Marrow," Cancer, Feb. 15, 1991, pp. 1033-1036, vol. 67.

Nagrath, S. et al., "Isolation of rare circulating tumour cells in cancer patients by microchip technology," NIH Public Access Author Manuscript, May 10, 2011, pp. 1-11, published in final edited form as Nat., Dec. 20, 2007, pp. 1235-1239, vol. 450, No. 7173.

Nedosekin, D. et al., "Photothermal Multispectral Image Cytometry for Quantitative Histology of Nanoparticles and Micrometastasis in Intact, Stained and Selectively Burned Tissue," Cytometry Part A, 2010, pp. 1049-1058, vol. 77A.

Nedosekin, D. et al., "Ultra-fast photoacoustic flow cytometry with a 0.5 MHz pulse repetition rate nanosecond laser," Opt. Exp., 2010, pp. 8605-8620, vol. 18.

Nedosekin, D. et al., "In Vivo Ultra-Fast Photoacoustic Flow Cytometry of Circulating Human Melanoma Cells Using Near-Infrared High-Pulse Rate Lasers," Cytometry Part A, 2011, pp. 825-833, vol. 79A.

Nedosekin, D. et al., "In Vivo Plant Flow Cytometry: A First Proof-of-Concept," Cytometry Part A, 2011, pp. 855-865, vol. 79A.

Nedosekin, D. et al., "Photothermal Confocal Spectromicroscopy of Multiple Cellular Chromophores and Fluorophores," Biophys. J., Feb. 2012, pp. 672-681, vol. 102.

Nedosekin, D. et al., "Synergy of photoacoustic and fluorescence flow cytometry of circulating cells with negative and positive contrasts," J. Biophotonics, 2013, pp. 425-434, vol. 6, No. 5, Wiley-VCH Verlag GmbH & Co. KGaA, Weinheim, Germany.

Nedosekin, D. et al., "Photoacoustic and photothermal detection of circulating tumor cells, bacteria and nanoparticles in cerebrospinal

(56) References Cited

OTHER PUBLICATIONS fluid in vivo and ex vivo," J. Biophotonics, 2013, pp. 523-533, vol. 6, No. 6-7, Wiley-VCH Verlag GmbH & Co. KGaA, Weinheim, Germany.

Nedosekin, D. et al., "Photoacoustic-fluorescence in vitro flow cytometry for quantification of absorption, scattering and fluorescence properties of the cells," Proc. SPIE, 2013, pp. 858141-1 to 858141-6, vol. 8581.

Neeves, K. et al., "Catch Me if You Can: Isolating Circulating Tumor Cells from Flowing Blood," Clin. Chem., 2012, pp. 803-804, vol. 58, No. 5.

Nguyen, D. et al., "Metastasis: from dissemination to organ-specific colonization," Nat. Rev. Cancer, Apr. 2009, pp. 274-284, vol. 9, Macmillan Publishers Limited.

Novak, J. et al., "In vivo flow cytometer for real-time detection and quantification of circulating cells," NIH Public Access Author Manuscript, Jan. 4, 2010, pp. 1-8, published in final edited form as Opt. Lett., Jan. 1, 2004, pp. 77-79, vol. 29, No. 1.

O'Brien, C. et al., "Detection and Isolation of Circulating Melanoma Cells using Photoacoustic Flowmetry," J. Vis. Exp., Nov. 2011, pp. 1-5, vol. 57, e3559.

\* cited by examiner

FIG. 3A.
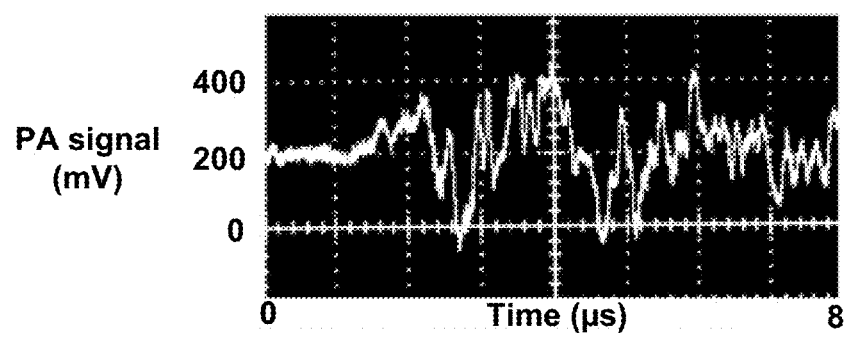
FIG. 3B.
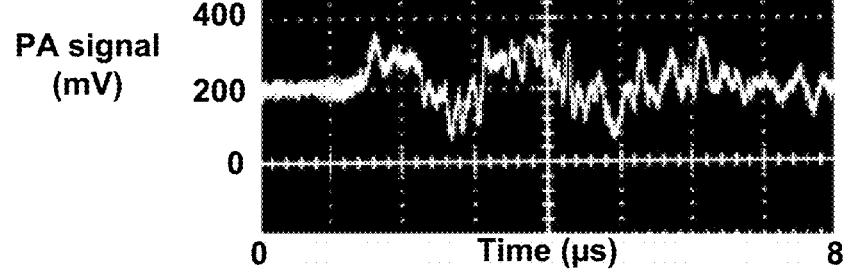
FIG. 3C.
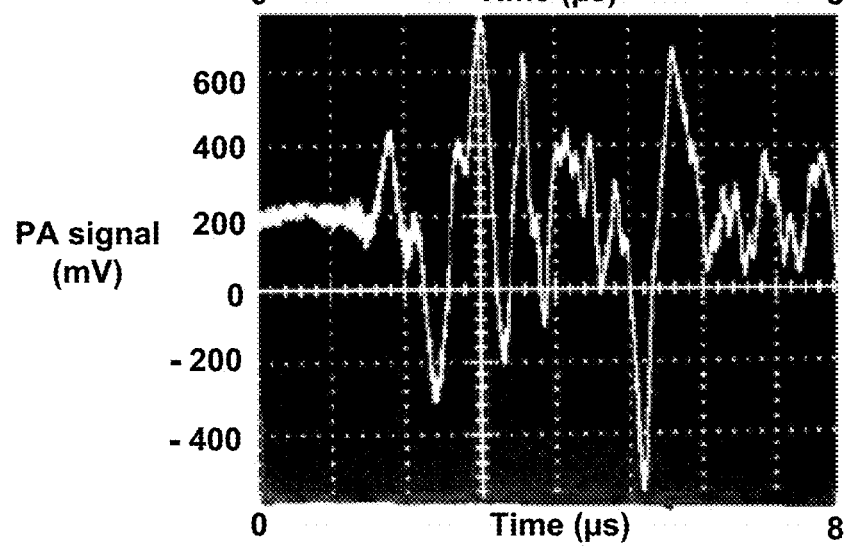
FIG. 3D.
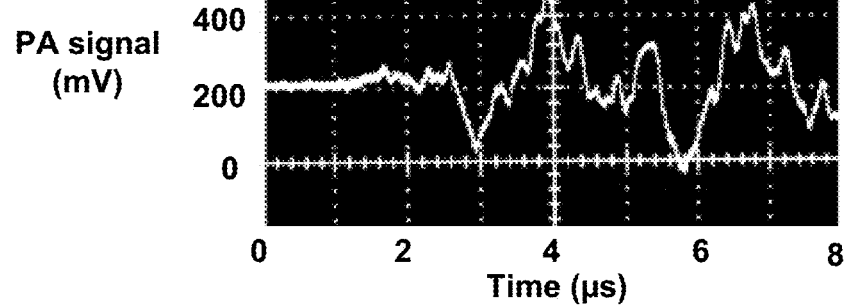
FIG. 3

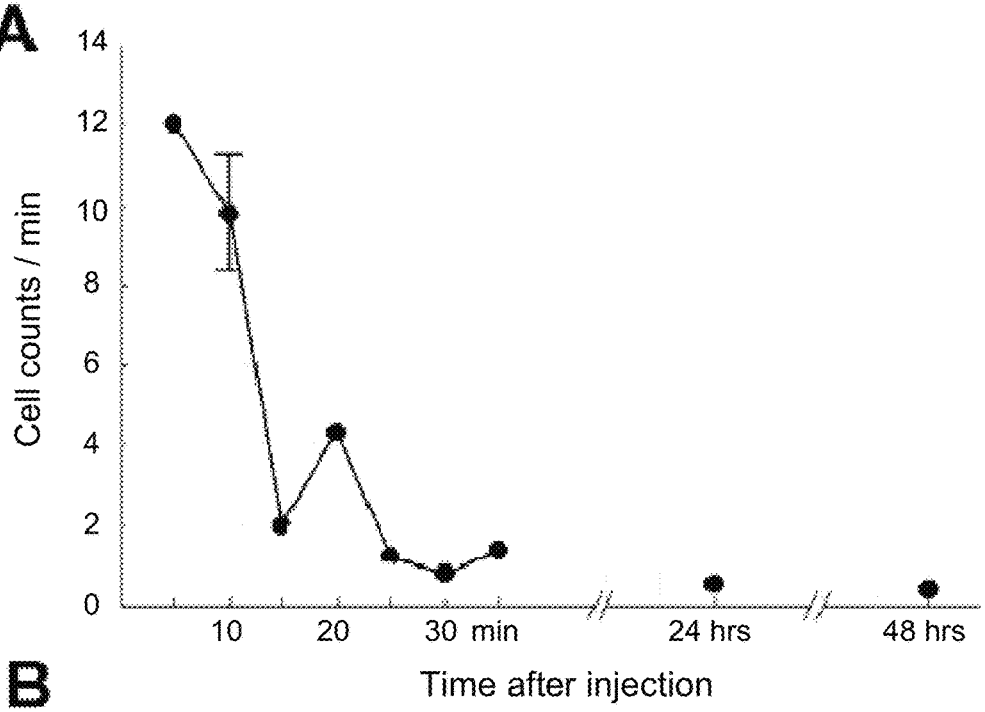
FIG. 10A
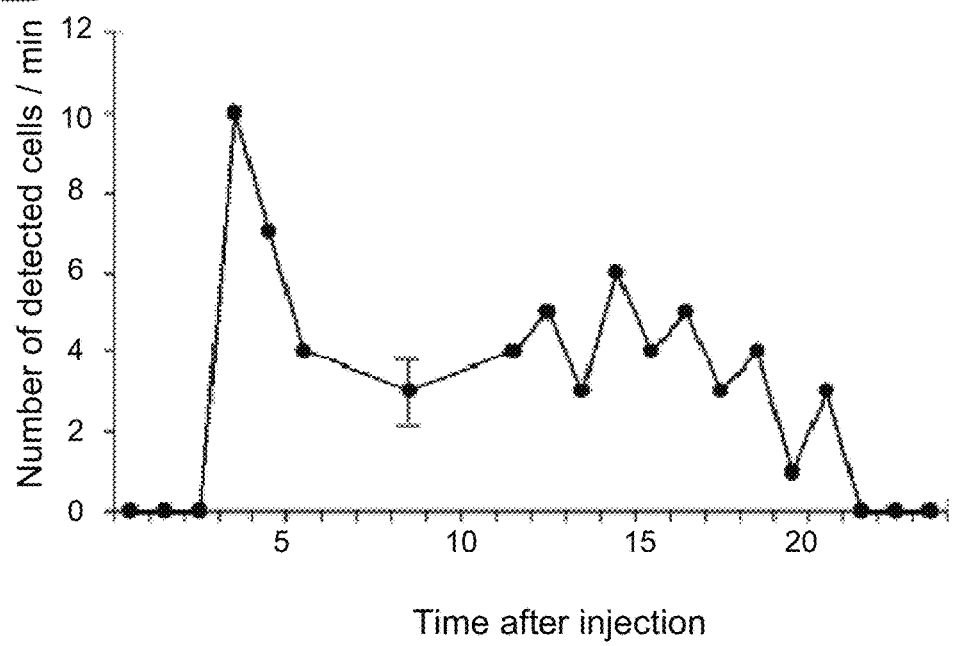
FIG. 10B
FIG. 10

FIG. 13 A.
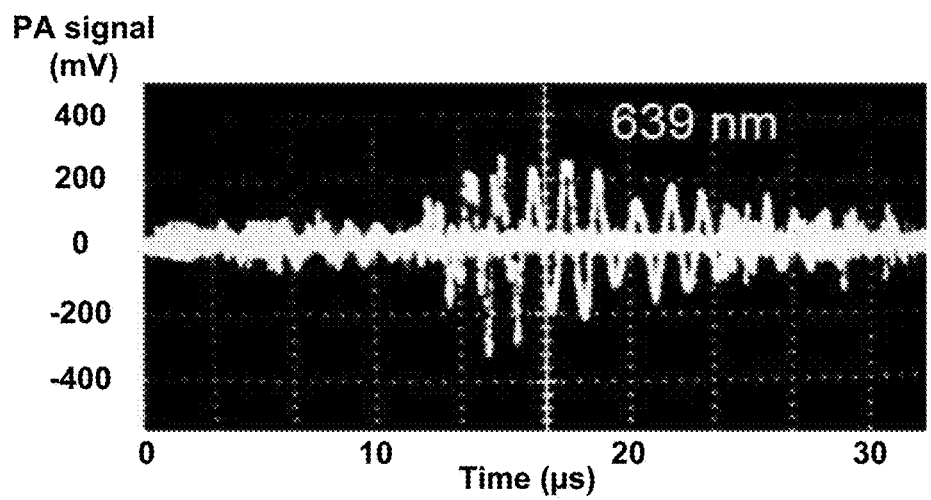
FIG. 13 B.
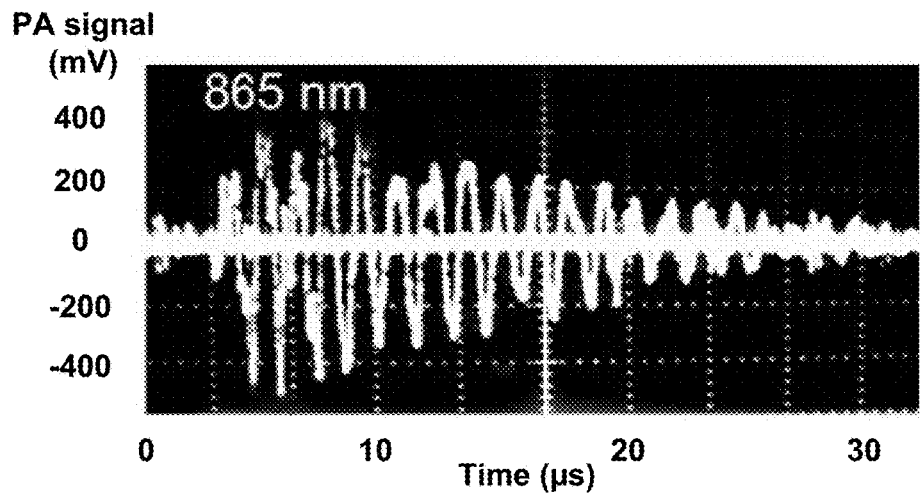
FIG. 13 C.
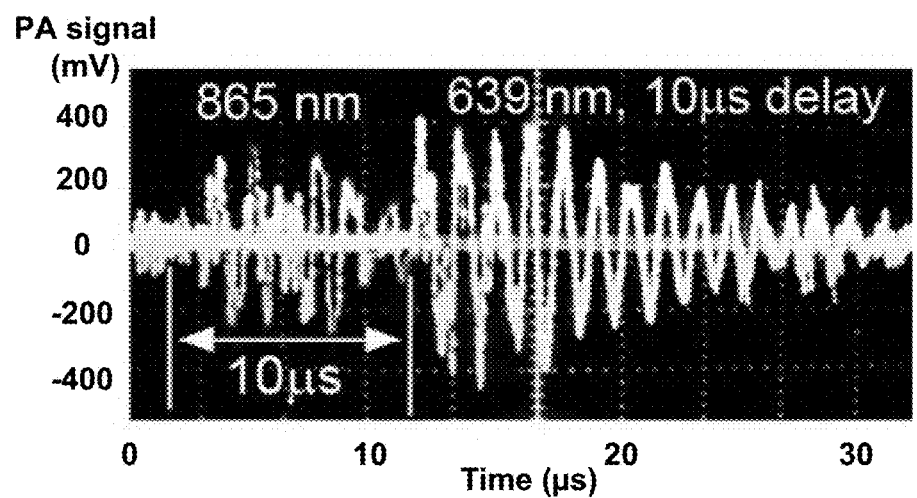
FIG. 13

FIG. 14 A.
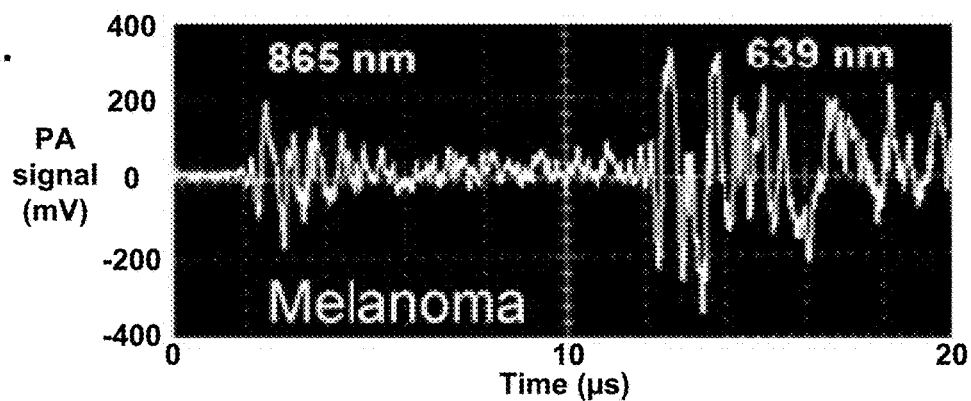
FIG. 14 B.
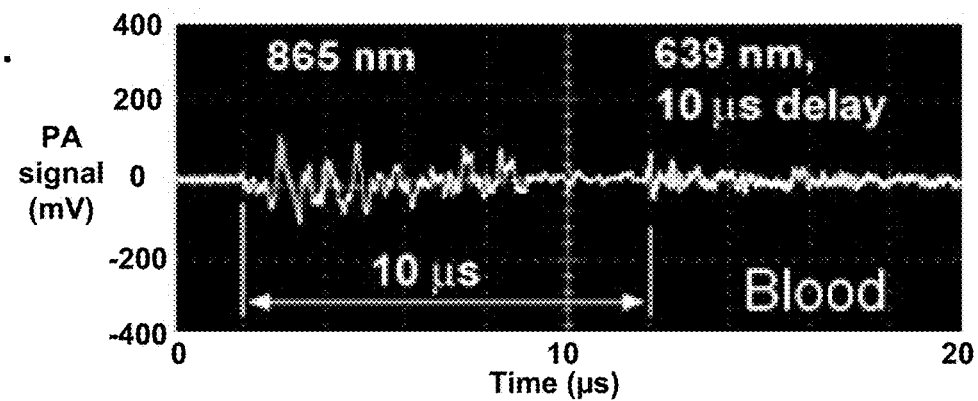
FIG. 14
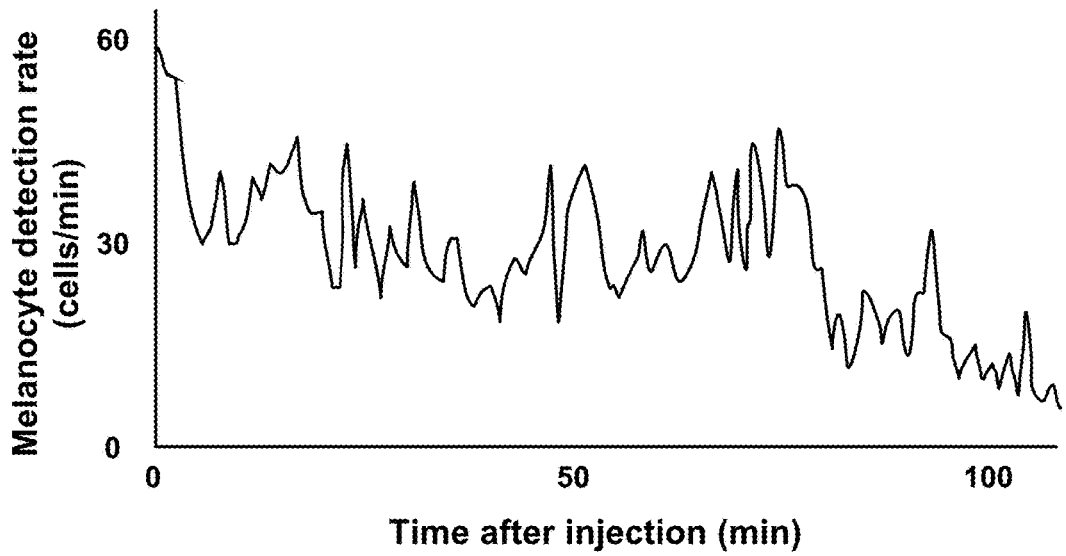
FIG. 15

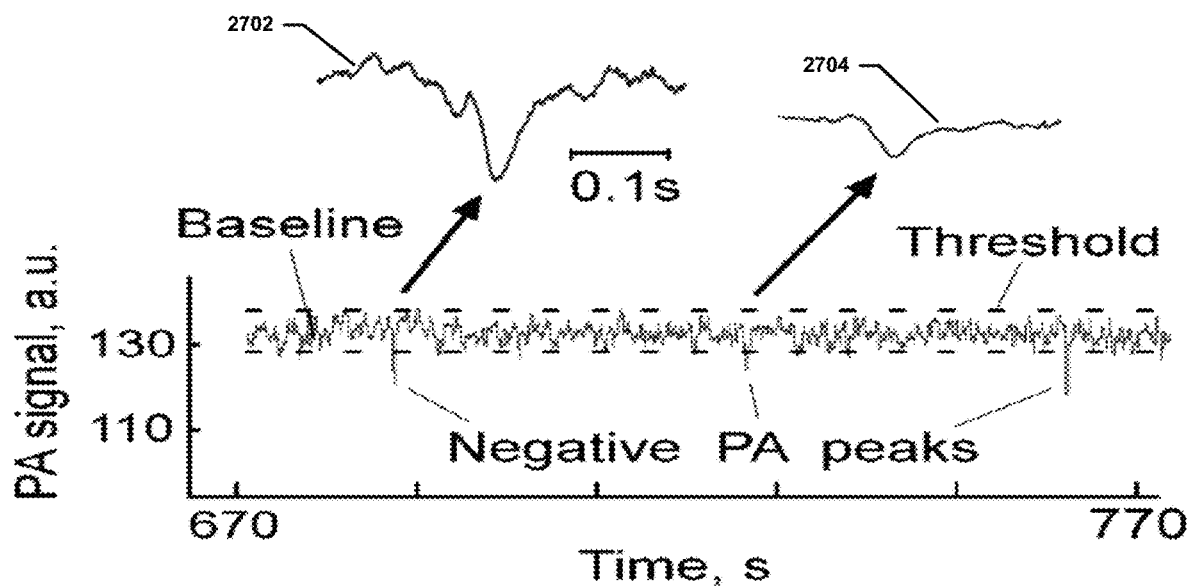
FIG. 27
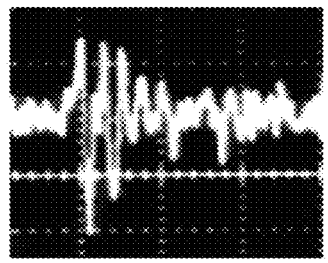
FIG. 28 A
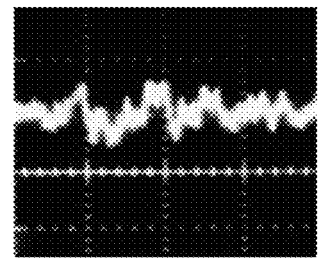
FIG. 28 B
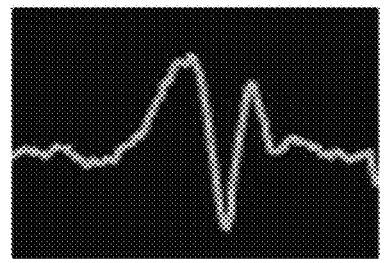
FIG. 28 C
FIG. 28

FIG. 30A
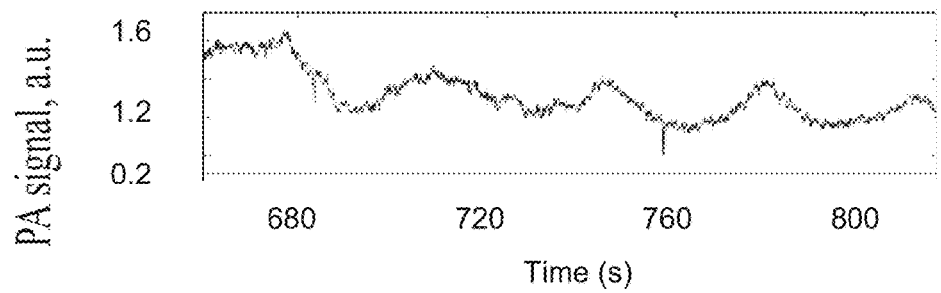
FIG. 30B
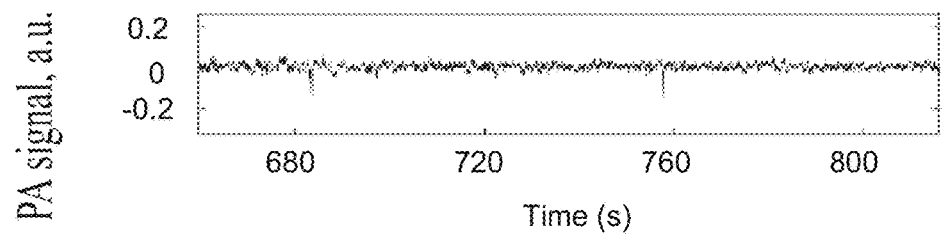
FIG. 30
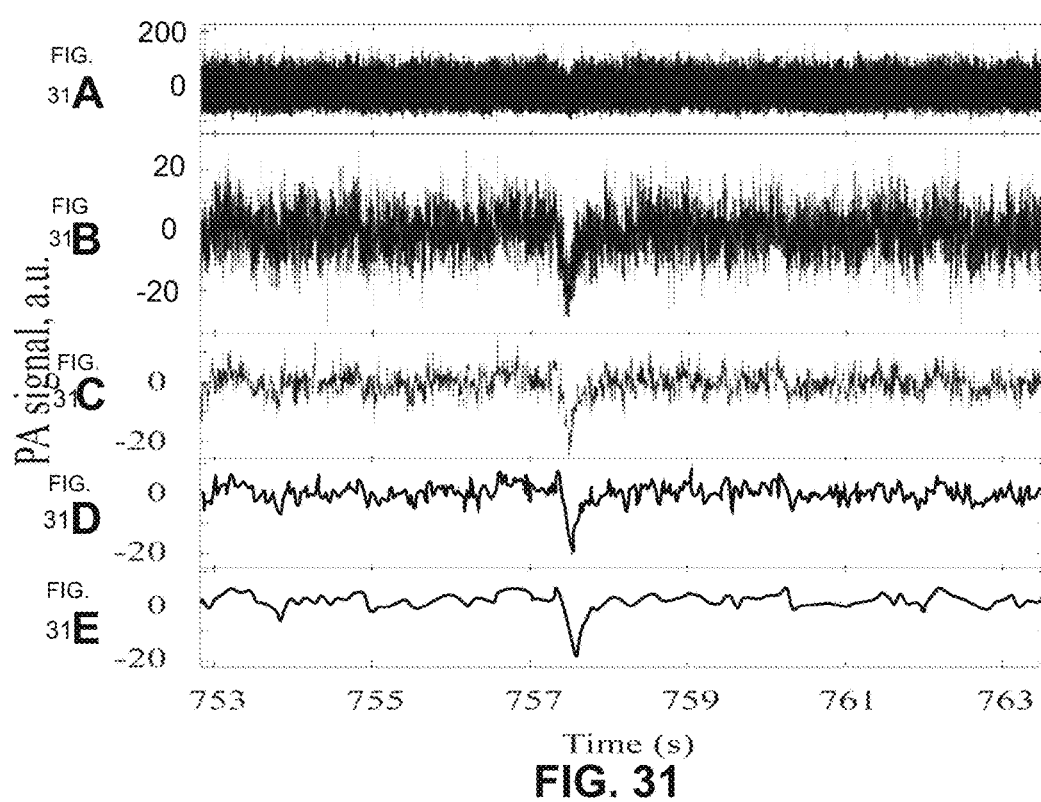
FIG. 31

DEVICE AND METHOD FOR IN VIVO DETECTION OF CLOTS WITHIN CIRCULATORY VESSELS

CROSS REFERENCE TO RELATED APPLICATIONS

This application is a continuation of U.S. patent application Ser. No. 15/240,712 filed Aug. 18, 2016 which is a divisional of U.S. patent application Ser. No. 13/253,767, entitled "Device and Method for In Vivo Detection of Clots Within Circulatory Vessels" filed on Oct. 5, 2011, which is a continuation-in-part of U.S. patent application Ser. No. 12/945,576, entitled "Device and Method for In Vivo Non-invasive Magnetic Manipulation of Circulating Objects in Bioflows" filed on Nov. 12, 2010, which is a continuation-in-part of U.S. patent application Ser. No. 12/334,217, entitled "Device and Method for In Vivo Flow Cytometry Using the Detection of Photoacoustic Waves" filed on Dec. 12, 2008, both of which are hereby incorporated by reference in their entireties. U.S. patent application Ser. No. 12/334,217 claims priority from U.S. provisional patent application Ser. No. 61/013,543, entitled "Device and Method for In Vivo Flow Cytometry Using the Detection of Photoacoustic Waves" filed on Dec. 13, 2007.

GOVERNMENTAL RIGHTS IN THE INVENTION

This invention was made with government support under grant numbers R01 EB000873, R21 EB005123, R01 CA131164, R21 CA139373, and R01 EB009230 awarded by the National Institutes of Health as well as grant number DBI-0852737 awarded by the National Science Foundation. The government has certain rights in the invention.

FIELD OF THE INVENTION

This application relates to a device and methods of using the device to detect the presence and composition of clots and other target objects in a circulatory vessel of a living subject. In particular, this application relates to devices and methods of detecting the presence and composition of clots and other target objects in a circulatory vessel of a living subject using in vivo photoacoustic flow cytometry techniques.

BACKGROUND

Despite progress in the diagnosis and treatment of cardiovascular diseases, heart attack and stroke remain among the leading causes of death. One common risk factor for cardiovascular diseases is the presence of circulating clots. These circulating clots (also known as thrombi) may unexpectedly block blood vessels, preventing delivery of oxygen-rich blood to vital organs, such as the heart and brain, and potentially causing unexpected acute events, including strokes and heart attacks. Although these acute events are typically caused by relatively large clots, victims of acute coronary thrombosis may harbor many microthrombi in vessels as small as 120 µm in diameter or less. At present, no clinically relevant method has been developed for the early detection of circulating clots, despite their clinical significance as prognostic markers for incipient strokes and heart attacks, as well as the potential for prevention of acute clot-related events through well-timed therapeutic clot elimination.

Existing ex vivo methods of detecting clots typically involve invasive extraction of blood samples and time-consuming analysis techniques. The temporal resolution of existing ex vivo methods is limited by the discrete time-point nature of drawing blood samples. As a result, the effectiveness of existing ex vivo methods is limited for monitoring the development of clots over time. Further, the sensitivity of existing ex vivo methods is relatively poor due to the difficulty of obtaining blood samples from clinically relevant sites, such as the carotid artery, limiting the analysis to relatively small-volume blood samples.

Many of the limitations of existing ex vivo methods may be overcome using the assessment of larger blood volumes in vivo. However, existing non-invasive diagnostic techniques suitable for in vivo assessments such as MRI, PET, ultrasound, and optical imaging are only capable of detecting fixed clots or slowly moving large clots in circulation. Existing fluorescent imaging techniques have been used to detect rolling clots in experimental models of colitis, and to assess the heterogeneity of adhered clots. However, the translation of existing fluorescent imaging methods from experimental models to in vivo use in humans may be problematic due to the toxicity of the fluorescent labels used in fluorescent imaging, as well as the challenge of detecting clots against a strong in vivo autofluorescent background. Other visualization techniques, such as pulse Doppler ultrasound, may be of limited use for clot screening due to the complexity of the technique, the difficulty of clot recognition within the surrounding blood and tissues, and measurement artifacts related to air bubbles.

Photoacoustic (PA) imaging is a technique based on the detection of laser-induced thermoelastic acoustic waves. PA imaging provides greater detection sensitivity and spatial resolution of target objects, such as cells and biomarker compounds, within tissues as deep as 3-5 cm compared to other optical visualization techniques, such as fluorescent imaging. As applied to vein thrombosis staging, PA imaging techniques have been used to detect stationary thrombus phantoms in vitro. However, PA detection of circulating clots in vivo using existing techniques is limited by the slow signal acquisition algorithms currently in use.

A need exists for a device and method for detecting circulating clots in vivo, continuously, and non-invasively with high detection sensitivity and spatial resolution. Such a device and method would make possible the detection of clots ranging in size from microclots to larger, slower-moving clots over extended periods. The increased resolution may further allow for the early detection of circulating microclots, facilitating the use of microclots as biomarkers for the early prediction of incipient acute events such as heart attacks or strokes. The early detection of microclots and the ability to monitor the development of clots over extended periods may better inform decisions such as the timing of therapeutic clot elimination treatments, as well as monitor the effectiveness of such treatments.

SUMMARY

Aspects of the present invention provide a method for detecting a clot property within a circulatory vessel of a living organism. The method includes pulsing a clot within the circulatory vessel with at least one pulse of laser energy at a first pulse wavelength. The first pulse wavelength induces a photoacoustic signal from the clot that is lower in magnitude than the photoacoustic signal induced from surrounding red blood cells. The method also includes obtaining a photoacoustic pattern emitted by the clot induced by at least one pulse of laser energy. The photoacoustic pattern may include at least one photoacoustic signal. The method further includes analyzing the photoacoustic pattern to calculate at least one characteristic of the photoacoustic pattern, and comparing the at least one characteristic of the photoacoustic pattern to a set of calibration patterns to determine one or more clot properties.

This method of detecting clots makes use of a negative photoacoustic contrast technique described herein. This technique exploits the significantly lower absorption of laser pulse energy by platelets compared to red blood cells at selected ranges of pulse wavelengths. It was surprisingly discovered that circulating clots produced photoacoustic signals that were significantly lower in magnitude than the background photoacoustic signals produced by the surrounding bloodstream. As a result, a sharp reduction in the magnitude of photoacoustic signals within a series of photoacoustic signals may be associated with the detection of a clot in this technique.

In another aspect, a device for the continuous monitoring of a circulatory vessel of a living organism is provided that includes an in vivo flow cytometer, a clot monitoring system, and an alarm system. The in vivo flow cytometer includes a pulsed laser for pulsing a clot within the circulatory vessel and an ultrasound transducer for receiving a photoacoustic signal emitted by a clot in response to the at least one pulse of laser energy. The clot may be pulsed at a pulse wavelength ranging between about 500 nm and about 600 nm. The clot monitoring system analyzes a photoacoustic pattern that includes at least one photoacoustic signal and produces a detection signal if the photoacoustic pattern indicates a clot. The alarm system provides an alarm signal to the living organism in response to a detection signal produced by the clot monitoring system.

In yet another aspect, a wearable device for the continuous monitoring of a circulatory vessel of a living organism is provided that includes an in vivo flow cytometer, a clot monitoring system, an alarm system, and a power source. The in vivo flow cytometer includes a pulsed laser for pulsing a clot within the circulatory vessel and an ultrasound transducer for receiving a photoacoustic signal emitted by a clot in response to the at least one pulse of laser energy. The clot may be pulsed at a pulse wavelength ranging between about 500 nm and about 600 nm. The clot monitoring system analyzes a photoacoustic pattern that includes at least one photoacoustic signal and produces a detection signal if the photoacoustic pattern indicates a clot. The alarm system provides an alarm signal to the living organism in response to a detection signal produced by the clot monitoring system. The power source provides power to the in vivo flow cytometer, the clot monitoring system, and the alarm system. The device is secured to an appendage of the living organism chosen from an arm, a leg, a finger, a toe, a neck, and a head.

The devices and methods provided in various aspects of the present invention overcome limitations of previous devices and methods for clot detection and treatment. Non-invasive photoacoustic flow cytometry devices may be used in conjunction with the method of detecting a clot property to continuously monitor the blood flow through a circulatory vessel of a living organism for extended periods. As a result, the entire blood volume may be assessed for clot properties such as the presence, concentration, composition, or size of circulating clots as the blood flow passes through a circulatory vessel. Further, the progression of a clot-related health condition, or the efficacy of an anti-clot treatment may also be assessed over extended periods without need for multiple invasive procedures such as repeated blood sampling.

Additional objectives, advantages and novel features will be set forth in the description which follows or will become apparent to those skilled in the art upon examination of the drawings and the detailed description which follows.

BRIEF DESCRIPTION OF THE DRAWINGS

The following figures illustrate various aspects of the invention.

FIGS. 3A-3D show the oscilloscope trace recordings of PA signals: (FIG. 3A) from blood flow in a rat ear vessel with diameter of 50 µm, (FIG. 3B) from skin surrounding a rat ear vessel before dye injection, (FIG. 3C) from blood flow in a rat ear vessel 5 min after the injection of Lymphazurin, and (FIG. 3D) from the skin surrounding a rat ear vessel measured 20 min after dye injection.

FIGS. 10A-10B are graphs showing the frequencies of circulating mouse melanoma cells (B16F10) detected with label-free PAFC in 50-µm mouse ear veins, with a flow velocity of 5 mm/s, in mice with low (FIG. 10A) and high (FIG. 10B) melanin pigmentation as a function of post-injection time.

FIGS. 13A-13C show oscilloscope traces of the two-wavelength, time-resolved detection of PA signals from: (FIG. 13A) necrotic lymphocytes labeled with gold nanorods absorbing 639 nm laser pulses, (FIG. 13B) apoptotic lymphocytes labeled with gold nanoshells absorbing 865 nm laser pulses, and (FIG. 13C) live neutrophils labeled with carbon nanotubes absorbing both the 639 nm and the 865 nm laser pulses.

FIGS. 14A-14B show oscilloscope traces of the two-wavelength, time-resolved detection of PA signals from: (FIG. 14A) melanoma cells absorbing 865 nm and 639 nm laser pulses, and (FIG. 14B) red blood cells absorbing 865 nm and 639 nm laser pulses.

FIG. 15 is a summary of the PA signal rates from melanin particles detected in a mouse ear lymph microvessel 2 hours after injection.

FIGS. 21E-21H are the photothermal signals obtained from the samples shown in FIGS. 21A-21D, respectively. FIGS. 21I-21L are the photoacoustic signals obtained from the samples shown in FIGS. 21A-21D, respectively.

FIG. 27 is a graph of the photoacoustic signals generated using laser pulses of 532 nm on a blood vessel in a mouse ear, showing several negative signal dips corresponding to the detection of circulating platelet aggregates. The insets are enlarged views of single negative signal dips.

FIG. 28 shows oscilloscope traces of the photoacoustic signals measured in a mouse carotid artery before the formation of clots (FIG. 28A), after occlusion by a clot (FIG. 28B), and photoacoustic signals from circulating heterogeneous clots in a mouse skin vessel (FIG. 28C).

FIG. 30 includes a graph of the photoacoustic signals measured from blood flow containing circulating clots in a mouse ear vessel before (FIG. 30A) and after (FIG. 30B) the application of a high-pass filter to the photoacoustic signal data.

FIGS. 31A-31E are graphs of the photoacoustic signals measured from blood flow containing circulating clots in a mouse ear vessel showing raw data (FIG. 31A), and after signal-averaging the signals from 16 consecutive laser pulses (FIG. 31B), from 64 consecutive laser pulses (FIG. 31C), from 256 consecutive laser pulses (FIG. 31D), and from 1024 consecutive laser pulses (FIG. 31E).

Corresponding reference characters indicate corresponding elements among the views of the drawings. The headings used in the figures should not be interpreted to limit the scope of the claims.

DETAILED DESCRIPTION

Figure 1:
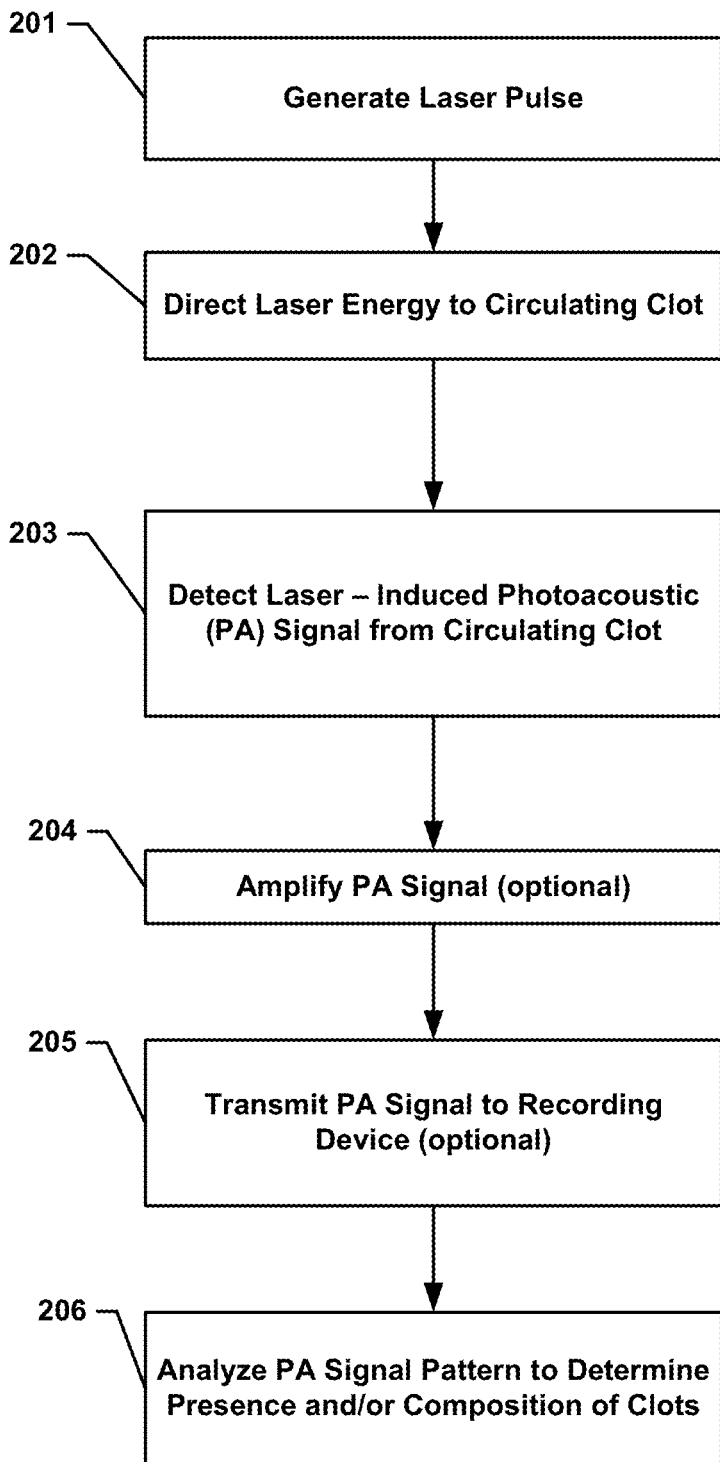
FIG. 1 is a flow chart of a photoacoustic in vivo flow cytometry method.

The present invention relates to methods and devices for the continuous detection of clots moving through a circulatory vessel of a living organism. The clots may be detected using devices and methods similar to the photoacoustic flow cytometers (PAFC) described in U.S. patent application Ser. No. 12/334,217, which is hereby incorporated by reference in its entirety, and as described herein.

It has been discovered unexpectedly that circulating clots could be detected using a negative photoacoustic contrast technique. In this technique, a circulating clot may be detected by pulsing the clot with a laser pulse having a wavelength that is absorbed by the platelets within the clot to a significantly lower degree relative to the absorption by surrounding red blood cells. As a consequence, the photoacoustic signal produced by a clot pulsed at this wavelength is significantly lower in magnitude than the photoacoustic signals produced by surrounding red blood cells. By comparing the photoacoustic signals produced by the clots to the average background photoacoustic signal produced by red blood cells and surrounding tissues, the clots may be detected as a negative dip in the photoacoustic signal magnitude received by the PAFC.

The pattern of photoacoustic signals detected from circulating clots may be analyzed to assess a clot property including, but not limited to, the size or composition of a clot. For example, the magnitude or duration of a negative dip in the photoacoustic signal may be analyzed to determine the size of a clot. A characteristic signal pattern such as positive spike in the photoacoustic signal preceding and/or following a negative dip may provide information regarding the composition of a clot.

This method of detecting clots in the circulatory vessel of a living organism may be used to determine the presence and extent of circulating clots in order to assess the organism's risk of adverse events such as strokes or heart attacks, to assess the efficacy of an anti-clot treatment, or to direct the application of an anti-clot treatment. For example, the detection of a clot may trigger the pulsing of the detected clot with a high-energy laser pulse in order to ablate the clot.

Further, a wearable device may be used to detect clots in the circulatory vessel of the living organism. The device may include a miniaturized PAFC system that detects clots and issues an alarm in the event of a detected clot. The alarm may provide a warning to the organism and/or may summon medical attention. In another embodiment, the device may be used to continuously monitor the flow through a blood vessel, and the detection of a clot may trigger a high-energy laser pulse at a wavelength and intensity sufficient to selectively eliminate the detected clot.

Further descriptions of the methods and devices for the detection of clots in the circulatory vessels of living organisms are provided herein.

I. Method of Detecting Clots

An in vivo device capable of detecting circulating clots in the circulatory vessel of a living organism, such as a photoacoustic flow cytometer (PAFC) may be used in conjunction with a negative photoacoustic contrast technique to detect the clots. A PAFC detects photoacoustic (PA) signals, typically in the form of ultrasound pulses, generated by circulating clots in response to the absorption of energy from a laser pulse directed at the clots. Subsequent analysis of the pattern of PA signals may be used to determine one or more clot properties, including but not limited to the size and composition of the clot.

FIG. 1 is a flowchart summarizing a method of detecting a clot in a circulatory vessel of a living organism using a PAFC as the detection device. A laser pulse is generated by the PAFC at step 201 and directed to the circulating clot at step 202. A PA signal is emitted by the clot in response to the absorption of the laser pulse. This PA signal is detected by the PAFC using a sensor such as an ultrasound transducer at step 203, and the detected PA signal may be optionally amplified and/or transmitted to a recording device at step 205. The patterns of PA signals are analyzed at step 206 to determine the presence or composition of the clots. For example, analysis of the PA signal pattern may identify a negative spike in the PA signal magnitude that may indicate the detection of a circulating clot.

a. Photoacoustic Flow Cytometry

Figure 2:
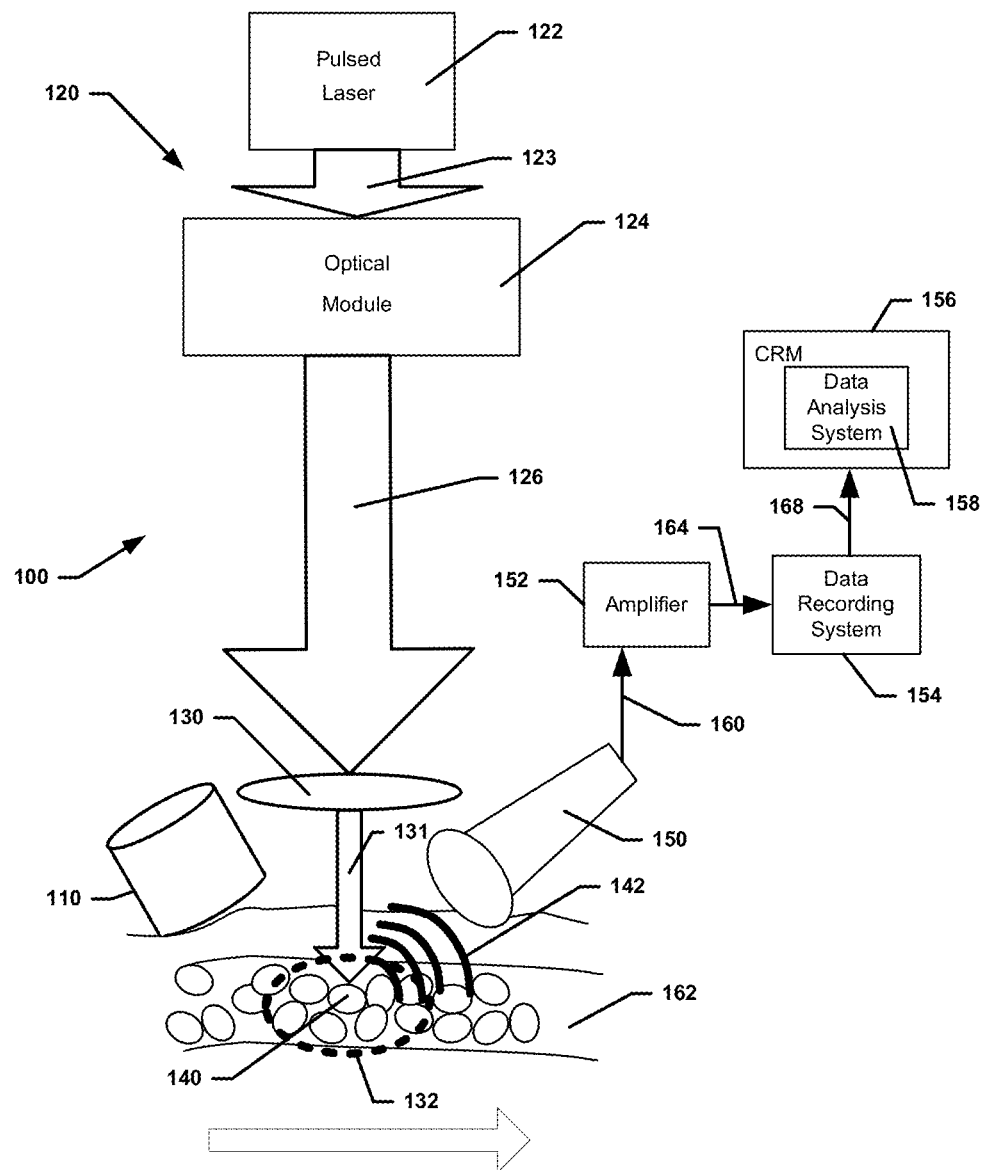
FIG. 2 is a schematic diagram illustrating an in vivo photoacoustic flow cytometry (PAFC) device.

A photoacoustic flow cytometry (PAFC) device may be used to perform non-invasive in vivo flow cytometry in order to detect circulating clots within the vessel of a living organism. Referring to FIG. 2, the PAFC device 100 is operated by illuminating a circulating clot 140 or other target object with one or more laser energy pulses 131, thereby inducing the clot 140 to emit a photoacoustic (PA) signal 142. The PA signal 142 typically falls within the ultrasound spectrum, with a range of frequencies between about 20 kHz and about 200 MHz. The PA signal 142 emitted by the clots 140 may result from the absorption of the one or more laser energy pulses 131 by a variety of mechanisms including, but not limited to: single photon absorption, two photon absorption, multi-photon absorption, Coherent Anti-Stokes Raman Scattering (CARS), and combinations thereof.

The ultrasound transducer 150 detects the PA signal 142 emitted by the clot 140, and the output 160 from the ultrasound transducer 150 may be analyzed using a data analysis system 158 residing on a computer-readable media 156 to identify one or more clot properties including but not limited to the size of the clot 140 and the composition of the clot 140. In an aspect, an amplifier 152 may amplify the output 160 of the ultrasound transducer 150 to produce an amplified signal 164 and this amplified signal 164 may be analyzed using the data analysis system 158. In another aspect, the amplified signal 164 may be stored in a data recording system 154, as illustrated in FIG. 2. In yet another aspect, the data analysis system 158 may be used to retrieve and analyze stored PA signal data 168.

Because the ultrasound waves of the PA signals travel freely through most biological tissues, the PAFC device 100 may be used to detect circulating clots 140 in circulatory vessels as deep as 15 cm below the external surface of the organism. Further, because the laser power used by the PAFC device 100 is relatively low, the PAFC device 100 may be operated for extended time periods with minimal damage to circulating cells and surrounding tissues. A PAFC device 100 using a negative photoacoustic contrast technique may be used for the continuous monitoring of clots for the early diagnosis and treatment of strokes, heart attacks, and other clot-related disorders.

b. Negative Photoacoustic Contrast Technique of Clot Detection

In an aspect, a negative photoacoustic contrast technique may be used to detect clots in a circulatory vessel of a living organism and to determine one or more clot properties based on an analysis of photoacoustic patterns associated with the clots. As described above, the in vivo photoacoustic flow cytometry (PAFC) device may be used to collect laser-excited photoacoustic (PA) signals emitted by at least one type of target object, which may be a clot, within a circulatory vessel. The photoacoustic patterns comprising PA signals collected over one or more consecutive laser pulses may be analyzed to determine at least one clot property. Non-limiting examples of clot properties that may be determined using the analysis of a photoacoustic pattern associated with the clot include: the size of the clot, the type or composition of the clot, the quantity of clots, the concentration of clots, the flow speed of the clots within the circulatory vessel, the age of the clot, the origin of the clot, and combinations thereof.

Figure 22:
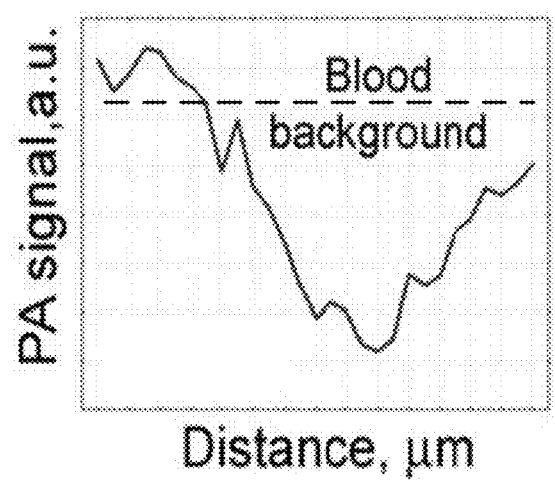
FIG. 22 is a graph showing the spatial distribution of photoacoustic signals obtained from the average of eight scans of a collagen-induced platelet aggregate in a blood sample.

It was unexpectedly discovered that platelets, which typically make up a significant portion of clots, emit a relatively weak PA signal compared to the stronger background PA signals emitted by other target objects such as red blood cells and other blood components in response to laser pulses at the same wavelength. For example, the photoacoustic pattern emitted by a clot suspended within a blood sample is shown in FIG. 22. The dashed line in this figure represents the average PA signal strength emitted by the surrounding blood sample, which predominantly includes PA signals emitted by red blood cells. However, the PA signals emitted by the clot are significantly lower in strength than the background blood PA signal strength. This negative spike in PA signal strength indicates the detection of a clot. "Negative spike", as used herein, refers to an abrupt reduction in PA signal strength within a photoacoustic pattern. For example, the photoacoustic pattern illustrated in FIG. 22 includes a negative spike 2202. The analysis of photoacoustic patterns associated with the clot, including but not limited to the shape of the negative PA signal spike, the duration of the negative PA signal spike, and the magnitude of the negative PA signal spike, may be used to identify various clot properties.

i. Photoacoustic Patterns

Photoacoustic (PA) patterns may be analyzed to determine a clot property such as clot size or composition. A PA pattern, as used herein, refers to a time series of one or more PA signals emitted by one or more target objects in response to the absorption of one or more consecutive laser pulses delivered at one or more pulse wavelengths. In general, PA patterns may be associated with a particular type of target object including, but not limited to, clots. Different types of target objects typically possess unique combinations of pigments and sub-cellular structures that absorb laser pulses and emit PA signals differently. Each type of target object may be uniquely identified by its distinctive PA pattern, as well the differences in PA patterns elicited by different wavelengths of laser pulses by the same target object.

The contrast of the PA patterns of the clots relative to surrounding cells and tissues typically result from PA signal amplitudes from the clots that are significantly lower than the PA signal amplitudes from surrounding cells and tissues. The PA contrast of a clot, as defined herein, refers to the difference between the PA signal amplitude from a clot and the PA signal amplitude from surrounding blood cells and tissues. Circulating clots may be detected through the time-resolved monitoring of dynamic decreases of the PA signal amplitude, due to the attenuated PA signal amplitude emitted by clots relative to the PA signal amplitude emitted by surrounding red blood cells. The decreased PA signal amplitude emitted by clots is due to the lower energy absorption of platelets (a component of blood clots) relative to the energy absorption of red blood cells (a common cell type in typical blood flows) for laser pulses in the visible and near-infrared spectral range, as discussed above.

Non-limiting examples of PA patterns suitable for identifying a clot property include pattern shape, frequency spectrum of the pattern, PA signal amplitude, as well as phase shift and/or time delay between one or more laser pulses and the received PA signal within a pattern. The PA signals within a PA pattern may be discriminated between PA signals detected from clots and background PA signals detected from surrounding cells and circulatory vessel walls and tissues. In an aspect, the PA pattern is the amplitude of the negative spike associated with a clot. In this aspect, the PA signal amplitude detected from the clot may be less than about 50% of the signal amplitude detected from the surrounding target objects and tissues. In another aspect, the PA signal amplitude detected from the clot is less than about 10% of the signal amplitude detected from the surrounding target objects and tissues. In yet another aspect, the PA signal amplitude detected from the clot is less than about 1% of the signal amplitude detected from the surrounding target objects and tissues. Photoabsorbant marker particles may be attached to the clots to enhance the degree of contrast of the PA signals of the clots relative to the PA signals of the surrounding target objects such as blood and tissues.

Figure 23:
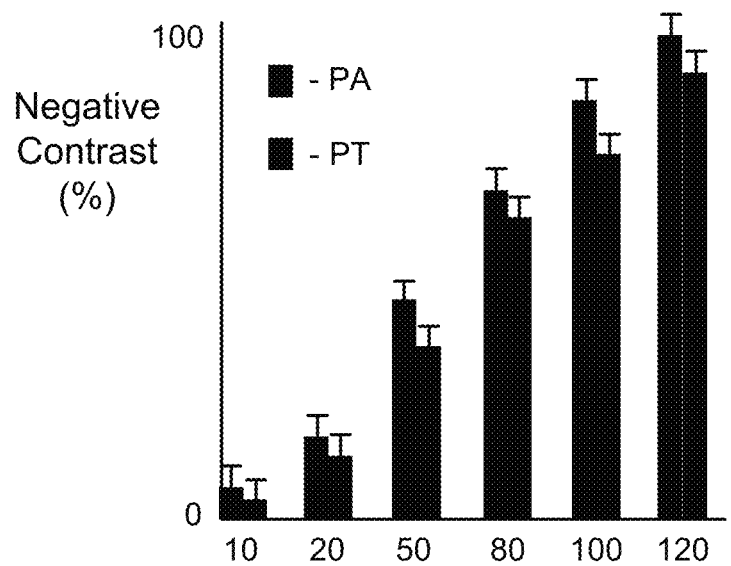
FIG. 23 is a graph of the negative contrast of collagen-induced platelet aggregates relative to surrounding blood cells in a blood sample as a function of aggregate size.

In another aspect, the contrast of the PA signal of a clot may be used to determine the size of a clot. For example, FIG. 23 is a summary of the negative contrast of a series of clots of different sizes. Based on these data, larger clots were associated with a higher degree of negative contrast. Other indications of the overall size of a clot may include, but are not limited to, the absolute magnitude of the PA signal of a clot and the duration of a negative PA spike.

Figure 24:
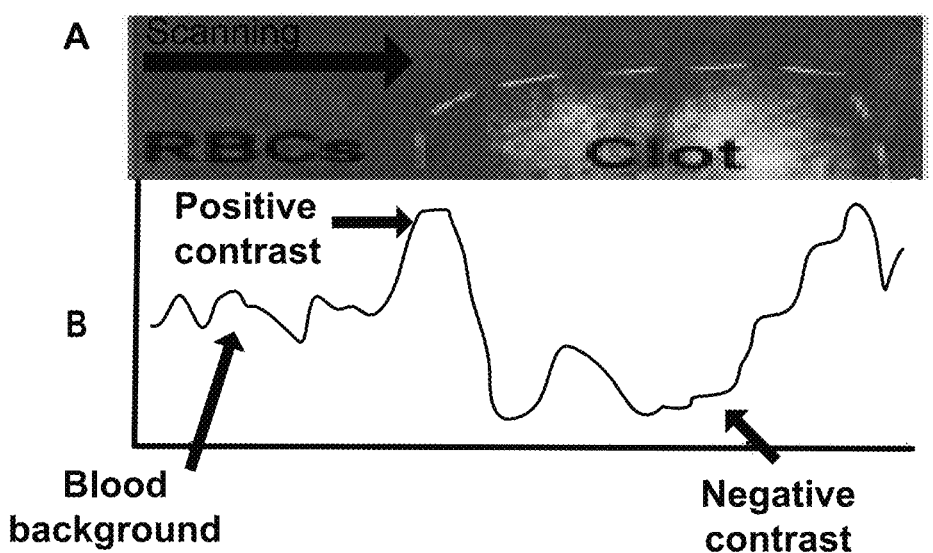
FIG. 24 includes an optical image (FIG. 24A) and a corresponding photoacoustic scan (FIG. 24B) of a heterogeneous blood clot suspended in a whole blood sample.

In yet another aspect, the shape of a PA pattern may be used to indicate the composition of a clot. The composition of a clot may depend on one or more factors including but not limited to the age of the clot, the size of the clot, and the presence or absence of surrounding cells such as red blood cells, white blood cells, and circulating tumor cells, which may be incorporated into the clot. The composition of a clot may include the proportion of platelets relative to other clot components, the spatial distribution of these other components within the clot, and any combination thereof. For example, FIG. 24 is a PA pattern resulting from a photoacoustic scan of a clot within a blood sample. The PA pattern in FIG. 24 is characterized by a positive PA spike followed by a negative PA signal dip followed by a second positive PA spike. In this figure, the positive PA spikes indicate a high concentration of red blood cells within the peripheral surface of the clot that emits strong PA signals. The negative PA signal dip indicates a platelet-rich center region of the clot. By contrast, the negative PA dips shown in FIG. 27 lack the prominent positive PA spikes preceding and following the negative PA dip, indicating that the detected clots in FIG. 27 are relatively rich in platelets.

Figure 29:
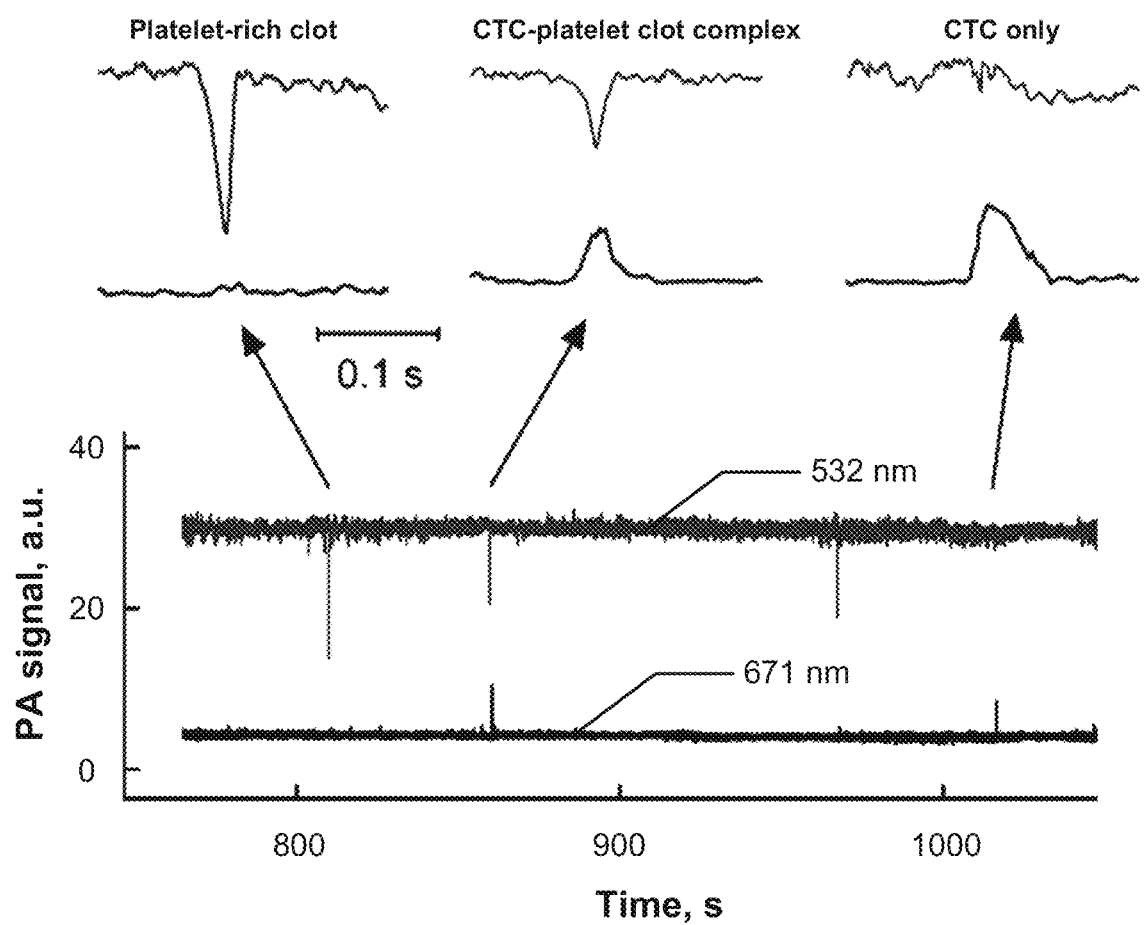
FIG. 29 is a graph of the photoacoustic signals generated by laser pulses having wavelengths of 532 nm and 671 nm measured from blood flowing through glass tubes that contained a mixture of target objects: circulating tumor cells (CTCs) labeled with gold nanorods, platelet-rich clots, and labeled CTC-platelet clot complexes. An enlargement of the photoacoustic signals associated with the detection of each type of circulating target object is shown in the inset graphs.

In another aspect, two or more photoacoustic patterns detected in response to laser pulses from two or more pulse wavelengths may be compared to determine the composition of a clot or other clot property. For example, FIG. 29 is a summary of the PA signals received in response to laser pulses of two different pulse wavelengths: 532 nm and 671 nm pulses. As illustrated in FIG. 29, red blood cells are responsive to 532 nm pulses, circulating tumor cells (CTCs) are responsive to 671 nm pulses, and platelets are relatively unresponsive to either pulse wavelength, resulting in negative spikes in PA patterns associated with platelets. By comparing the PA patterns resulting from different pulse wavelengths, it may be determined whether a clot contains mostly platelets, as indicated by the photoacoustic patterns in the left inset graph, or whether a clot further includes CTCs, as indicated by the photoacoustic patterns in the center inset graph of FIG. 29.

The velocity of the flow within a circulation vessel may be determined using PA patterns including but not limited to the PA signal duration, the PA frequency shift, or the time delay between two PA signals produced by a single target object pulsed by two distinct laser pulses applied at a known separation distance. The speed of movement of a clot within the circulation vessel may be determined by identifying the presence of a clot using the analysis of PA patterns as described above, and then determining the velocity of the identified clot using PA patterns including but not limited to the PA signal duration, the PA frequency shift, or the time delay between two PA signals produced by a single clot pulsed by two distinct laser pulses applied at a known separation distance.

In an aspect, the overall flow velocity and the speed of movement of a clot within a circulatory vessel may be determined and compared to assess clot properties. For example, a speed of movement of a clot that is comparable to the overall flow speed within the circulatory vessel may indicate a small, freely-moving clot, whereas a clot speed that is much slower than the surrounding flow speed may indicate a larger clot or a rolling clot. Other factors may be considered in conjunction with the clot speed to determine additional clot properties such as the age and origin of the clot. For example, if the organism has other factors such as a previous history of clots or known adhered clots elsewhere in the organism, the detection of small, fast moving clots may indicate that these fast-moving clots may have fractured from a larger, slower-moving clot or an adhered clot elsewhere within the organism.

The photoacoustic patterns may be analyzed by comparing the photoacoustic patterns to a set of calibration patterns obtained from clots having known clot characteristics including, but not limited to, clot size and clot composition. The set of calibration patterns may include patterns obtained at various PAFC conditions including, but not limited to, laser pulse wavelength, laser pulse duration, laser pulse fluence, frequency of laser pulses, and any combination thereof.

ii. Selection of Pulse Wavelength

A critical factor in the negative photoacoustic contrast technique is the selection of a laser pulse wavelength that results in PA signals emitted by clots that are significantly lower than the PA signals emitted by other blood components including but not limited to red blood cells and other target objects within the circulatory vessel of the living organism. In an aspect, the laser wavelength may be selected for the negative photoacoustic contrast technique based on the difference in absorption of the clots relative to other target objects within the circulatory vessel.

Figure 19:
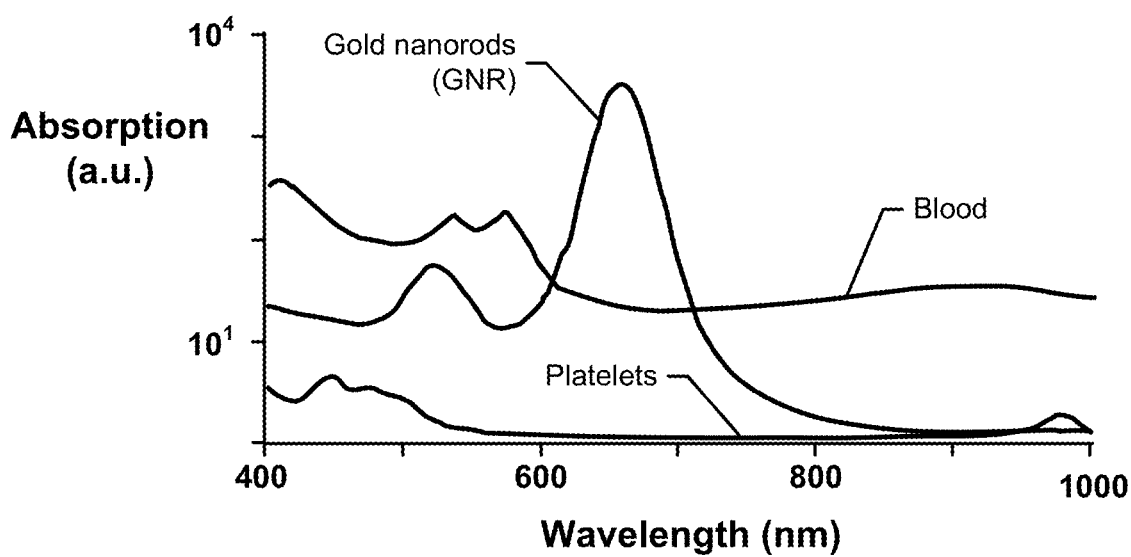
FIG. 19 is an absorption spectrum of platelets compared to the corresponding spectra of blood cells and gold nanotubes.

Clots typically include platelets as part of their composition along with other blood components including, but not limited to, red blood cells and circulating tumor cells. In an aspect, a laser wavelength that is not well absorbed by platelets, but is strongly absorbed by other blood components may be selected as the pulse wavelength for the detection of clots using a negative photoacoustic contrast technique. Without being limited to any particular theory, the higher absorbance of a laser pulse by a target object typically results in the emission of a stronger PA signal by that target object. Referring to FIG. 19, the absorption of laser energy for all wavelengths from about 400 nm to about 1000 nm by blood is significantly higher than the absorption by platelets. In particular, blood absorbs at least 10-100 times more laser energy at wavelengths ranging from about 500 nm to about 600 nm than platelets. In an aspect, the pulse wavelength used to detect a clot property may fall within a strong blood absorption band and may range between about 500 nm and about 600 nm or between about 530 nm and about 580 nm. In another aspect, the pulse wavelength may be selected to induce a photoacoustic signal from the clot that is at least 5 times lower in magnitude than the photoacoustic signal obtained from surrounding red blood cells induced by the pulse wavelength. In an additional aspect, the pulse wavelength used to detect a clot property in a circulatory vessel may be about 532 nm, the wavelength resulting in the maximum contrast between blood and platelets according to the data summarized in FIG. 19.

In yet another aspect, PA signals induced by two or more laser pulses in which each laser pulse has a unique pulse wavelength that differs from the pulse wavelength of the other pulses may be used to identify a clot property. In this aspect, at least one of the unique pulse wavelengths may be strongly absorbed by a non-platelet target object type, including but not limited to circulating tumor cells. PA patterns elicited by the two or more pulse wavelengths may be compared to detect a clot property as discussed herein above.

II. Clots and Other Target Objects

In various aspects, the negative photoacoustic contrast technique may be used to detect clots within the circulatory vessels of living organisms. The clots may be detected at a resolution of at least about 1 clot per mL of blood. Using this method to continuously monitor the blood as it flows through a circulatory vessel may detect clots at a concentration of about 5 clots or less within the entire blood volume of the organism. The individual clots detected using this method may be as small as about 20 μm.

In an aspect, the clots may be detected within circulatory vessels at a depth ranging from about 10 μm to about 15 cm below the surface of the skin. Non-limiting examples of circulatory vessels include capillaries, arterioles, venules, arteries, veins, and lymphatic vessels. The diameters of the circulatory vessels may range between about 10 μm and about 2 cm. The diameter of the circulatory vessel may be selected in order to enhance the negative contrast of the clots relative to the surrounding blood flow. Leukocytes and the plasma layer within the blood flow may also produce significantly lower photoacoustic signals compared to surrounding red blood cells, resulting in negative contrast signals that confound the analysis techniques used to detect clots. Within small circulatory vessels such as capillaries, the confounding negative contrast from leukocytes and plasma is more pronounced; this confounding negative contrast is attenuated in larger-diameter circulatory vessels. In an aspect, the circulatory vessels in which clots are detected using the negative photoacoustic contrast technique may have a mean diameter of at least about 25 μm.

The circulatory vessels may be located in various organs and tissues, including, but not limited to skin, lips, eyelid, interdigital membrane, retina, ear, nail pad, scrotum, brain, breast, prostate, lung, colon, spleen, liver, kidney, pancreas, heart, testicles, ovaries, lungs, uterus, skeletal muscle, smooth muscle, and bladder. Clot properties may be detected in the circulatory vessels of any organism that possesses cells circulating in vessels or sinuses chosen from the group of organisms including mammals, reptiles, birds, amphibians, fish, mollusks, insects, arachnids, annelids, arthropods, roundworms, and flatworms.

The clots and other target objects detected in various aspects may include but are not limited to unlabeled biological cells, biological cell products, unbound contrast agents, biological cells labeled using contrast agents, aggregations of cells, platelet-rich white clots, red blood cell-rich clots, heterogeneous clots comprising platelets and one or more other target object types, and any combination thereof. The target objects may be unlabeled endogenous or exogenous biological cells or cell products including but not limited to normal, apoptotic and necrotic red blood cells and white blood cells; aggregated red blood cells or clots; infected cells; inflamed cells; stem cells; dendritic cells; platelets; metastatic cancer cells resulting from melanoma, leukemia, breast cancer, prostate cancer, ovarian cancer, and testicular cancer; bacteria; viruses; fungal cells; protozoa; microorganisms; pathogens; animal cells; plant cells; and leukocytes activated by various antigens during an inflammatory reaction and combinations thereof.

The target objects may also be biological cell products, including but not limited to products resulting from cell metabolism or apoptosis, cytokines or chemokines associated with the response of immune system cells to infection, exotoxins and endotoxins produced during infections, specific gene markers of cells such as tyrosinase mRNA and p97 associated with cancer cells, MelanA/Mart1 produced by melanoma cells, PSA produced by prostate cancer, and cytokeratins produced by breast carcinoma.

The target objects may also be contrast agents chosen from the group including indocyanine green dye, melanin, fluorescein isothiocyanate (FITC) dye, Evans blue dye, Lymphazurin dye, trypan blue dye, methylene blue dye, propidium iodide, Annexin, Oregon Green, C3, Cy5, Cy7, Neutral Red dye, phenol red dye, AlexaFluor dye, Texas red dye, gold nanospheres, gold nanoshells, gold nanorods, gold cages, carbon nanoparticles, prefluorocarbon nanoparticles, carbon nanotubes, carbon nanohorns, magnetic nanoparticles, quantum dots, binary gold-carbon nanotube nanoparticles, multilayer nanoparticles, clustered nanoparticles, liposomes, liposomes loaded with contrast dyes, liposomes loaded with nanoparticles, micelles, micelles loaded with contrast dyes, micelles loaded with nanoparticles, microbubbles, microbubbles loaded with contrast dyes, microbubbles loaded with nanoparticles, dendrimers, aquasomes, lipopolyplexes, nanoemulsions, polymeric nanoparticles, and combinations thereof.

The target objects may also be labeled cells, clots, platelets, or other target objects listed herein above, marked with molecular markers and tags comprised of contrast agents listed herein above. The molecular markers or tags may be attached to the cells without modification, or the contrast agents may be functionalized for binding to the cells using molecules including, but not limited to: antibodies, proteins, folates, ligands for specific cell receptors, receptors, peptides, viramines, wheat germ agglutinin, and combinations thereof. Non-limiting examples of suitable ligands include: ligands specific to folate, epithelial cell adhesion molecule (Ep-CAM), Hep-2, PAR, CD44, epidermal growth factor receptor (EGFR), as well as receptors of cancer cells, stem cells receptors, protein A receptors of *Staphylococcus aureus*, chitin receptors of yeasts, ligands specific to blood or lymphatic cell endothelial markers, as well as polysaccharide and siderophore receptors of bacteria.

Exogenous target objects such as unbound contrast agents and exogenous unlabeled biological cells may be introduced into the circulatory vessels of the organism parenterally, orally, intradermally, subcutaneously, or by intravenous or intraperitoneal administration.

III. Photoacoustic Flow Cytometry Device

A photoacoustic flow cytometry (PAFC) device may be used to detect the clots within the circulatory vessel of a living organism using the negative photoacoustic contrast technique described herein.

a. Overview of PAFC Device

FIG. 2 is a schematic illustration of a PAFC device 100 used in an aspect to detect clots within a circulatory vessel. The PAFC device 100 may include a tunable wavelength pulsed laser 120 capable of emitting light energy 126 ranging between wavelengths of about 400 nm and about 2500 nm. The tunable wavelength pulsed laser source 120 includes a pulsed laser 122, and may further include an optical module 124 to convert the wavelength, pulse rate, or both wavelength and pulse rate of the laser pulse 123 emitted by the pulsed laser 122 to desired values. In addition, the PAFC device 100 includes optical elements 130 such as lenses or optic fibers to direct the laser light 131 to the clots 140 within the area of interest 132. The PAFC device 100 also includes at least one ultrasound transducer 150 to detect photoacoustic signals 142 emitted by the clots 140. A magnet 110 may also be included in order to locally enrich the concentration of clots or other target objects within the area of interest 132 detected by the PAFC device 100. The PAFC device 100 may optionally include an amplifier 152, a data recording system 154, and computer readable media 156 with stored data analysis software 158.

The PAFC device 100 may further include additional elements including, but not limited to photodetectors, additional lasers and optics, and additional analysis software associated with other in vivo flow cytometry methods that detect the clots or other target objects using alternative detection methods. Non-limiting examples of alternative detection methods include methods that make use of the conventional and Raman scattering of the laser pulses by the clots or other target objects, photothermal effects induced by laser pulses on the clots or other target objects, and the fluorescence of the clots or other target objects induced by absorbed laser pulses. In an aspect, the PAFC device 100 may be configured to simultaneously detect cells using photoacoustic methods, photothermal methods, light scattered by target objects, induced fluorescence of target objects, and any combination thereof.

b. Data Processing

Data analysis software 158 may process data stored on the data recording system 154, the signal output from the ultrasonic transducer 150, the amplified signal output from the amplifier 152, or combinations thereof. The data analysis software 158 may also function as an amplifier, a data storage device, and combinations thereof. Any data analysis software capable of processing data obtained at signal acquisition frequencies ranging between about 20 Hz and 200 MHz may be used, including but not limited to user-written software and commercially available analysis software. Non-limiting examples of commercially available analysis software include Matlab (The MathWorks, Inc., USA), Mathematica (Wolfram Research, Inc., USA), Labview (National Instrument, USA), Avisoft (Avisoft Bioacoustics, Germany), and TomoView (Olympus NDT Inc., USA).

Any known method of processing the fluctuating PA signal data may be used in various aspects. For example, if a relatively high laser pulse rate is used to generate the PA signals using the PAFC device 100, data processing methods including signal filtering and signal averaging may be used to eliminate signal fluctuations or signal noise resulting from confounding factors including but not limited to movements of the living organism due to breathing, blood pulse, or other movements, as well as variation due to multiple PA signals received from the same clot or other target objects.

In one aspect, a series of multiple PA signals may be signal averaged to reduce fluctuations in the data series. Signal averaging is defined herein as the replacement of each PA signal value at a particular time with an average of a group of two or more PA signals, in which the averaged group of signals includes the original signal as well as one or more PA signals immediately preceding and/or following the original PA signal. The number of adjacent signals used in the signal averaging process may depend on at least one factor including, but not limited to: the frequency of fluctuations within the signal data, the number of signals per second acquired by the data analysis software, the laser pulse rate used to generate the PA signals, and any combination thereof. In this aspect, the number of adjacent PA signals that may be averaged in the signal averaging process may range from 2 PA signals to about 2,500 PA signals. If the laser pulse rate used by the PAFC is in excess of 10 KHz, even larger groups of PA signals may be averaged.

In another aspect, the PA signal data may be subjected to signal filtration using any known signal filter, including but not limited to a high-pass filter, a low-pass filter, and combinations thereof. A high-pass filter is defined herein as a signal processing technique that eliminates PA signal data fluctuating below a specified cutoff frequency. A low-pass filter is defined herein as a signal processing technique that eliminates PA signal data fluctuating above a specified cutoff frequency. The cutoff frequency may be specified by the user, or the cutoff frequency may be dynamically determined by the data analysis software. For example, the PA signal data may be subjected to a high-pass filter with a threshold frequency of about 100 Hz to eliminate low-frequency data fluctuations due to confounding factors such as movements of the organism due to breathing and blood pulse.

IV. Method for Eliminating Circulating Clots In Vivo

In an aspect, a method for the elimination of circulating clots in a circulation vessel of a living organism is provided that includes detecting the clots in the circulation vessel, and then pulsing the detected clot with at least one high-intensity pulse of laser energy to eliminate the detected clot. The high-intensity pulse may be delivered at significantly higher laser fluence than the laser fluence used for the detection of the clot, and may be delivered at a wavelength at which the clot has higher absorbance efficiency. In this method, the detection of a clot triggers a pulse of laser energy that is delivered to the detected clot at a wavelength and fluence sufficient to cause the destruction of the detected clot. The method may further include monitoring the frequency of detection of clots circulating through the circulatory vessels, and terminating the method when the frequency of detection of the clots falls below a threshold level. In an aspect, this method of eliminating clots may be terminated when the frequency of detection of clots falls below a rate ranging between about $10^{-3}$ clots/min and about $10^2$ clots/min.

V. Device for Continuous Monitoring of a Circulatory Vessel

In an aspect, a device for the continuous monitoring of a circulatory vessel of a living organism is provided. This device 300, shown as a block diagram in FIG. 20, includes an in vivo flow cytometer 302, a clot monitoring system 304, and an alarm system 306. This device 300 monitors the blood flow through a circulatory vessel and detects clots using the negative photoacoustic contrast techniques described previously herein. Upon the detection of a clot in the circulatory vessel, the alarm system 306 of the device 302 issues an alarm signal to notify the wearer or operator of the device 300, or to notify medical personnel.

The in vivo flow cytometer 302 is similar to the PAFC devices described previously herein. In this aspect, the in vivo flow cytometer 302 includes a pulsed laser for pulsing the clot within the circulatory vessel. In order to enhance the effectiveness of the negative photoacoustic contrast technique of clot detection, the pulsed laser may deliver at least one pulse of laser energy at a pulse wavelength ranging from about 500 nm to about 600 nm, as described herein. The in vivo flow cytometer 302 further includes an ultrasound transducer similar to the ultrasonic transducers described herein and as described in U.S. patent application Ser. No. 12/945,576. The ultrasonic transducer receives a photoacoustic (PA) signal emitted by the clot in response to the at least one pulse of laser energy.

The clot monitoring system 304 processes the PA signals detected by in vivo flow cytometer 302 to determine whether the pattern of PA signals indicates the detection of a clot. The photoacoustic pattern comprising at least one photoacoustic signal is analyzed using processes and methods similar to those described herein above. If a clot is detected by the clot monitoring system 304, a detection signal is produced.

The alarm system 306 receives detection signals from the clot monitoring system 304. Upon receiving a detection signal, the alarm system 306 may issue an alarm signal to the living organism. The alarm signal may be issued in response to a single detection signal, or after processing the detection signal using known methods. For example, the alarm signal may be issued after receiving a detection signal of sufficient magnitude to indicate an alarm condition, or after receiving two or more detection signals at a sufficiently high frequency.

The alarm signal may comprise an indication to the device's wearer of the detection of a clot and may be continuous or intermittent in nature. Any known indication may be used, including but not limited to a visual display, an audible sound, a vibration, a signal to summon medical assistance, and any combination thereof. In an aspect, the device 300 may further include a communication link to a hospital, medical center, or any other known location of medical assistance personnel in order to transmit the alarm signal to summon medical assistance. Any known communication link may be used to transmit the alarm signal, including but not limited to wireless communication technologies such as Bluetooth signals, cellular signals, wireless Internet signals, and any combination thereof.

Figure 20:
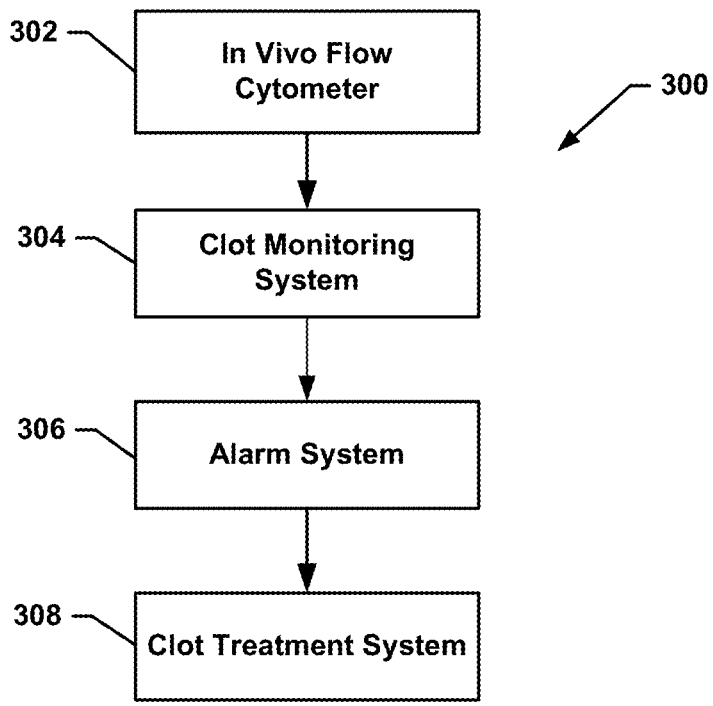
FIG. 20 is a schematic illustration of the subsystems of a device for the continuous monitoring of a circulatory vessel of a living organism.

In another aspect, the device 300 may further comprise a clot treatment system 308 for initiating a clot treatment in response to a detection signal and/or alarm signal. In this aspect, the clot treatment system 308 may receive a detection signal from the clot monitoring system 304 and/or an alarm signal from the alarm system 306, as illustrated in FIG. 20, and initiate a clot treatment in response. The clot treatment may be any known clot treatment including, but not limited to, the administration of an anti-clotting medication, or the pulsing of the clot with a high-intensity laser pulse at a laser fluence sufficient to eliminate the clot, as described previously herein.

The anti-clotting medication may be administered upon the receipt of a single signal, or the clot treatment system 308 may locally process the alarm and/or detection signals and administer anti-clotting medication based on a processed signal quantity including but not limited to the signal magnitude, the frequency of signals, the elapsed time since the previous signal, and any combination thereof. The anti-clotting medication may be administered in any known manner, including but not limited to the administration of discrete dosages, continuous administration, and any combination thereof. The discrete dosage amount and continuous rate of administration may be constant, may vary in accordance with a predetermined schedule, may be specified by the wearer or operator of the device 300, may be dynamically controlled by device feedback such as the frequency of alarm or detection signals, or any combination thereof.

The device 300 may be a laboratory-based or hospital-based device, or the device 300 may be a portable and self-contained device. In one aspect, the device 300 may be a self-contained wearable device to be worn by a living organism to continuously monitor a circulatory vessel for clots. In this aspect the self-contained wearable device may further include a power source including, but not limited to a battery. The device 300 may be removably attached to a fixed location on the living organism using known methods including but not limited to straps, adhesive patches and adhesive strips. The device 300 may be removably attached at any external location on a living organism that is situated within a suitable distance of a circulatory vessel for continuous monitoring using the methods described previously herein. Non-limiting examples of suitable external locations include the neck, wrist, forearm, upper arm, hand, foot, ankle, lip, ear, chest, abdomen, eye, scalp, and leg.

EXAMPLES

The following examples illustrate aspects of the invention.

Example 1. Determination of Laser-Induced Cell Damage to Blood Cells and Subsequent Cell Viability Associated with In Vitro Photothermal (PT) Imaging To determine whether the laser pulses associated with in vivo flow cytometry caused any significant damage to cells or tissues of the organism, the following experiment was conducted. The laser-induced damage threshold of single cells was evaluated as a function of the pumped-laser energy levels at a range of wavelengths using established methods (Zharov and Lapotko 2005, Lapotko and Zharov 2005). In vitro measurements of specific changes in photothermal (PT) images and PT responses from individual cells were used to determine cell damage. During the PT imaging, individual cells were illuminated with a pulse of laser light at a specified energy level and wavelength. After absorbing the energy of the laser pulse, the short-term temperature of the cell increased by as much as 5° C. The laser-induced temperature-dependent refractive heterogeneity in the vicinity of cells caused defocusing of a collinear He—Ne laser probe beam (model 117A; Spectra-Physics, Inc.; 633 nm, 1.4 mW) that illuminated the cell immediately after the initial laser pulse. This defocusing caused a subsequent reduction in the beam's intensity at its center, which was detected with a photodiode (C5658; Hamamatsu Corp.) through a 0.5-mm-diameter pinhole.

PT measurements were performed in vitro using mouse blood cells in suspension on conventional microscope slides. To simulate blood flow conditions, a flow module fitted with a syringe pump-driven system (KD Scientific, Inc.) was used with glass microtubes of different diameters in the range of 30 μm to 4 mm that provided flow velocities of 1-10 cm/sec, which were representative of the diameters and flow rates of animal microvessels.

Individual cells flowing through the glass microtubes were exposed to an 8 ns burst of laser light in a 20-μm circular or elongated beam at a variety of wavelengths ranging between 420 nm and 2300 nm. At each wavelength of the initial laser pulse, the laser fluence, defined as the energy contained in the laser beam, was varied between 0.1 mJ/cm$^2$ and 1000 J/cm$^2$. Damage to the cells was determined by assessing the changes in the PT imaging response of cells to laser pulses of increasing fluence. In addition, cell viability after exposure to laser energy was assessed using a conventional trypan blue exclusion assay. Cellular damage was quantified as ED50, the level of laser fluence at which 50% of the measured cells sustained photodamage in vitro. The ED50 values measured for rat red blood cells (RBC), white blood cells (WBC) and K562 blast cells using laser pulses in the visible light spectrum are summarized in Table 1. The ED50 values measured for rat red blood cells (RBC) and white blood cells (WBC) using laser pulses in the near-infrared (NIR) light spectrum are summarized in Table 2.

TABLE 1

Photodamage thresholds for single rat blood cells in the visible light spectrum.

| Wavelength of laser pulse (nm) | Photodamage threshold ED50 (J/cm$^2$) | | |
|---|---|---|---|
| | Rat RBC | Rat WBC | Rat K562 blast cell |
| 417 | 1.5 | 12 | 36 |
| 555 | 5 | 42 | 90 |

TABLE 2

Photodamage thresholds for single rat blood cells in near-IR spectral range.

| Wavelength of laser pulse (nm) | Photodamage threshold ED50 (J/cm$^2$) | |
|---|---|---|
| | Rat RBCs | Rat WBCs |
| 740 | 6.9 | 21.7 |
| 760 | 6.8 | — |
| 780 | 17.7 | 152 |
| 800 | 17.5 | 219 |
| 820 | 28.0 | 251 |
| 840 | 43.5 | — |
| 860 | 43.8 | 730 |
| 880 | 76.5 | — |
| 900 | 69.4 | — |
| 920 | 77.7 | 357 |
| 960 | 33.5 | 48.8 |

In the visible spectral range, the relatively strong light-absorbing RBCs sustained cell damage at much lower intensities of laser energy, resulting in ED50 values that were about an order of magnitude lower than the ED50 values measured for WBC or K562 blast cells. In the NIR spectral range (wavelengths above about 800 nm), most cells including RBC have minimal absorption. As a result, neither the RBCs nor WBCs sustained damage in the NIR range until much higher laser energy levels compared to the energy levels at which cellular damage occurred to cells exposed to laser energy in the visible spectrum. The damage thresholds (ED50) for RBCs and WBCs in the spectral range of 860-920 nm were more than one order magnitude higher compared to those in the visible spectrum as shown in Tables 1 and 2.

The results of this experiment established the levels of laser energy at which laser-induced cellular damage may occur. In the NIR spectrum, in which cells exhibited the strongest photoacoustic effects, the damage thresholds are several orders of magnitude above the maximum safety level of approximately 20-100 mJ/cm$^2$ set by ANSI safety standards. Thus, photoacoustic flow cytometry may be performed in vivo with little risk of cell or tissue damage.

Example 2. Detection of Contrast Dye Circulating in Mice by Prototype In Vivo Photoacoustic Flow Cytometry System The following experiment was conducted to demonstrate the feasibility of in vivo photoacoustic flow cytometry (PAFC) for real-time, quantitative monitoring in the blood circulation of a conventional contrast agent, Lymphazurin. In this experiment, a prototype PAFC system was used to detect Lymphazurin circulating in the blood vessels of a mouse ear.

The prototype PAFC system was built on the platform of an Olympus BX51 microscope (Olympus America, Inc.) and a tunable optical parametric oscillator (OPO) pumped by a Nd:YAG laser (Lotis Ltd., Minsk, Belarus). The general layout of the PAFC system is shown schematically in FIG. 2. Laser pulses were produced at an 8 ns pulse width, a regular repetition rate of 10 Hz with the ability to provide short-term pulses at 50 Hz, and a wavelength in the range of 420-2,300 nm. Laser energy was directed to the blood vessels using a conventional lens and/or an optical fiber. PA signals emitted by the cells were detected by ultrasound transducers (unfocused Panametrics model XMS-310, 10 MHz; focused cylindrical Panametrics model V312-SM, 10 MHz, focused lengths of 6 mm, 12 mm, and 55 mm; and customized resonance transducers), and the ultrasound transducer outputs were conditioned by an amplifier (Panametrics model 5662, bandwidth 50 kHz-5 MHz; Panametrics model 5678, bandwidth 50 kHz-40 MHz; customized amplifiers with adjustable high and low frequency boundaries in the range to 50-200 KHz and 1-20 MHz, respectively; resonance bandwidth of 0.3-1.0 MHz). The amplifier output signals were recorded with a Boxcar data acquisition system (Stanford Research Systems, Inc.) and a Tektronix TDS 3032B oscilloscope, and were analyzed using standard and customized software. The Boxcar data acquisition technique provided averaging of the PA pulses emitted by cells in the blood vessels, and discriminated the PA waves from background signals originating from surrounding tissue on the basis of the difference in time delays between the two signals. The signals from the oscilloscope screen were recorded with a digital camera (Sony, Inc.) and video camera (JVC, Inc.).

A high-speed computer (Dell Precision 690 workstation with a quadcore processor, 4 GB of RAM, and a Windows Vista 64 bit operating system) and digitizer (National Instruments PCI-5124 high speed digitizer) were used to acquire the PA signal data from the PAFC device. National Instruments software (Labview Version 8.5 and NI Scope Version 3.4) was used to control the digitizer and to create a data logging user interface. The hardware and supporting program were capable of collecting data at a rate of 200 megasamples per second, corresponding to a time resolution of 5 ns.

A laser beam with a circular cross section and a diameter of approximately 50 µm, a wavelength of 650 nm, and a fluence of 35 mJ/cm$^2$ was used to illuminate the flow in the blood vessels. The 650 nm wavelength used was near the wavelength of maximum absorption of Lymphazurin, the contrast dye used in this experiment, and was well-separated from the wavelengths of maximum absorption of other blood components. Navigation of the laser beams was controlled with transmission digital microscopy (TDM) at a resolution of approximately 300 nm using a Cascade 650 CCD camera (Photometrics).

The in vivo experiments described below were performed using a nude mouse ear model. PAFC detection was performed using relatively transparent, 270 µm thick mouse ears with well-distinguished blood microvessels. The ear blood microvessels examined were located at a depth of 30-100 µm, had diameters in the range of 30-50 µm, and blood velocities of 1-5 mm/sec. After undergoing anesthesia using ketamine/xylazine at a dosage of 50/10 mg/kg, each mouse was placed on a customized heated microscope stage, together with a topical application of warm water, which provided acoustic matching between the transducer and mouse ear.

After anaesthetizing each mouse and placing the mouse on the microscope stage as described above, 200 µL of a 1% aqueous solution of Lymphazurin contrast agent (Ben Venue Labs Inc., USA) was injected into the tail vein of the mouse. PAFC measurements of the circulating dye were performed at a laser pulse wavelength of 650 nm. FIG. 3 shows oscilloscope traces of PAFC signals from the blood vessels and surrounding tissues in the rat ear before and after injection with Lymphazurin. Prior to injection, the maximum 240 mV PA signals from blood vessels, shown in FIG. 3A, were approximately 1.5 times higher than the 160 mV PA background signals from surrounding tissue, shown in FIG. 3B. Maximum PA signals from the blood vessel after dye administration, shown in FIG. 3C, increased approximately three-fold over pre-injection levels. The PA signals from tissue around vessels after dye injections, shown in FIG. 3D, gradually increased approximately 2.5-fold over pre-injection levels during the first 15-20 minutes, and then remained relatively constant for the next 1-1.5 hours, probably due to the passage of the Lymphazurin out of the blood vessels and into nearby lymphatic vessels.

Figure 4:
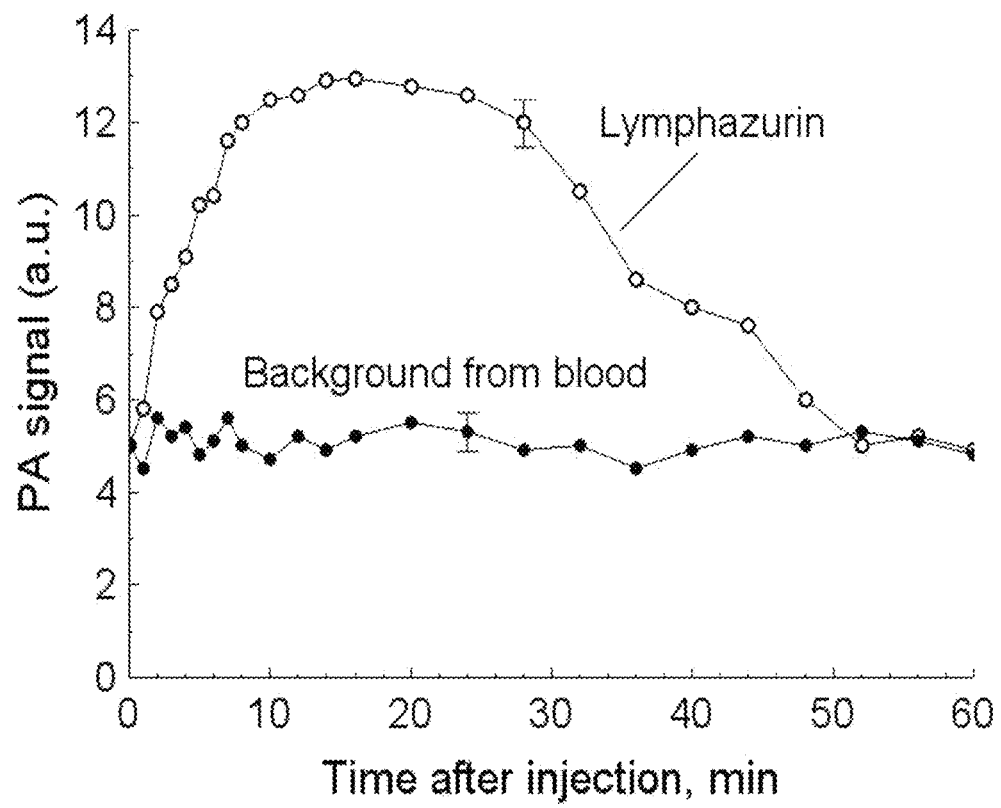
FIG. 4 shows the PA signal detected from the monitoring of the blood flow in a 50-µm rat ear microvessel after intravenous injection of Lymphazurin dye in the tail vein.

FIG. 4 summarizes the maximum PAFC signals from Lymphazurin compared to background PAFC signals from untreated blood vessels, observed for one hour after the injection of Lymphazurin. As shown in FIG. 4, continuous monitoring of PA signals from the ear blood microvessels revealed a rapid appearance of Lymphazurin in the blood flow within a few minutes after injection, followed by clearance of Lymphazurin from the blood over the next 50 minutes.

The results of this experiment demonstrated that the prototype PAFC system exhibited sufficient sensitivity to detect the presence of ultrasonic contrast dyes in circulation.

Example 3. Detection of Nanoparticles Circulating in Rats by Prototype In Vivo Photoacoustic Flow Cytometry System To demonstrate the sensitivity of the prototype in vivo photoacoustic flow cytometry (PAFC) system described in Example 2, the following experiment was conducted. The prototype PAFC system was used to detect nanoparticles intravenously injected into the tail veins of rats.

The in vivo measurements in this experiment were performed using a rat mesentery model. The rat (White Fisher, F344) was anesthetized using ketamine/xylazine at a dosage of 60/15 mg/kg, and the mesentery was exposed and placed on a heated microscope stage, and bathed in Ringer's solution at a temperature of 37° C. and a pH of 7.4. The mesentery consisted of transparent connective tissue of 7-15 µm thickness, and a single layer of blood and lymph microvessels.

The nanoparticles used in this experiment were gold nanorods (GNRs), obtained from the Laboratory of Nanoscale Biosensors at the Institute of Biochemistry and Physiology of Plants and Microorganisms in Saratov, Russia. On the basis of TEM and dynamic light scattering analyses, the GNR were estimated to be approximately 15 nm in diameter and approximately 45 nm in length on average. The GNRs were used either uncoated, or the GNRs were functionalized using thiol-modified polyethylene glycol (PEG) (Liao and Hafner 2005).

A 250-µL suspension of GNRs with a concentration of $10^{10}$ particles/ml was injected into the tail veins of three rats, followed by the continuous monitoring of PA signals measured from 50-µm diameter blood vessels in the rat mesentery using the PAFC system described in Example 2. PAFC measurements were taken using a laser fluence of 100 mJ/cm$^2$, a laser beam diameter of approximately 50 µm, and a laser wavelength of 830 nm, near the maximum absorption of the GNR.

Figure 5:
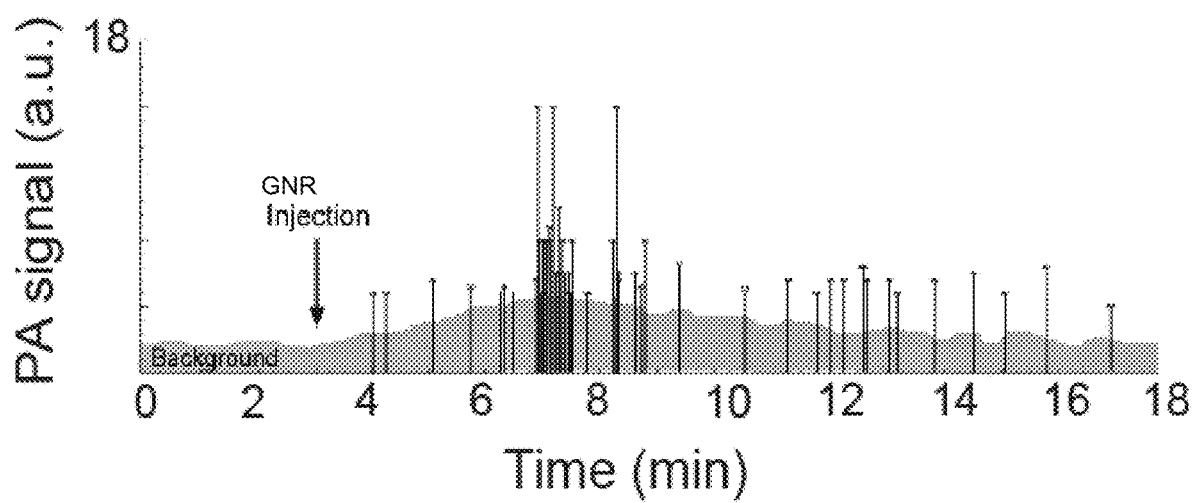
FIG. 5 shows the PA signal from circulating GNR in 50-µm rat mesentery microvessels as a function of post-injection time.

Uncoated GNR were rapidly cleared from the blood circulation within 1-3 minutes preferentially by the reticuloendothelial system (data not shown). After injection of the rats with PEGylated GNRs, strong fluctuating PA signals appeared with amplitudes significantly exceeding the PA background signals from blood vessels within the first minute and continued for 14-25 minutes, depending on the individual animal. In addition, the PA background signal from the blood vessel increased approximately 1.5-2 times above the pre-injection background levels, reaching a maximum level between four and nine minutes after injection, as shown in FIG. 5.

Figure 6:
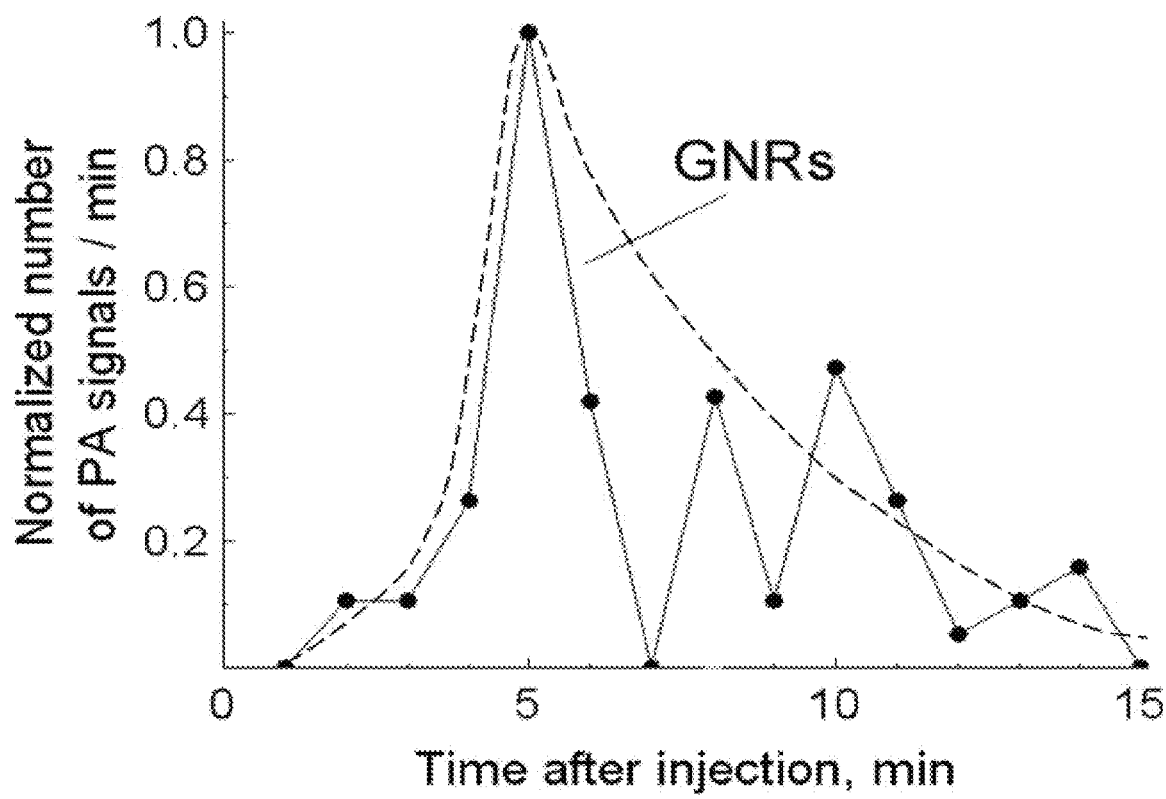
FIG. 6 is a graph of the normalized number of circulating GNR in blood microvessels of the rat mesentery as a function of post-injection time and a dashed curve showing averaged data (N=3).

The averaged PA signals from the three rats, measured for 15 minutes after injection with GNR suspensions, are summarized in FIG. 6. The maximum rate of individual PA signals per minute, indicative of the number of GNRs in circulation, was observed approximately 5 minutes after injection, with a gradual decrease in the PA signal rate over the next 10 minutes.

The results of this experiment demonstrated that the prototype PAFC system possessed sufficient spatial and temporal resolution to continuously monitor the circulation of nanoparticles as small as 15 nm in diameter. In addition, the prototype PAFC system was sufficiently sensitive to track fluctuations in the concentration of circulating particles from the time that they were injected to the time that the particles were cleared from circulation.

Example 4. Detection of *S. aureus* Bacteria Circulating in Mice Using Prototype In Vivo Photoacoustic Flow Cytometry System To demonstrate the ability of the prototype photoacoustic flow cytometry (PAFC) system to detect bacteria cells in vivo under biological conditions, the following experiment was conducted. The prototype PAFC system, previously described in Example 2, was used to measure *S. aureus* bacteria circulating in nude mice.

The mouse ear model described in Example 2 was used the measurements of circulating bacteria in this experiment. Because the endogenous light absorption of *S. aureus* bacteria was relatively weak compared to the absorption of other blood components in the NIR spectral range, the bacteria were labeled with the NIR-absorbing contrast substances indocyanine green dye (ICG) and carbon nanotubes (CNT), due to their relatively high labeling efficiency and low toxicity (data not shown).

A *S. aureus* bacterium strain designated UAMS-1 was isolated from a patient with osteomyelitis at the McClellan Veterans Hospital in Little Rock, Ark., USA. The strain was deposited with the American Type Culture Collection and is available as strain ATCC 49230. UAMS-1 was cultured in tryptic soy broth and grown aerobically for 16 h at 37° C. Cells were harvested by centrifugation, resuspended in sterile PBS and incubated with Indocyanine Green (ICG) dye (Akorn Inc., USA) or carbon nanotubes (CNT) as described below.

Before incubation, ICG dye was filtered through a 0.22 µm pore size filter. A 150-µl aliquot of bacteria in suspension was incubated with 375 µg of ICG in 150 µL of solution for 30 min at room temperature and then for 2 h at 37° C. Labeled bacteria were centrifuged at 5,000 rpm for 3 min and the resulting pellet was resuspended in PBS.

Single-walled carbon nanotubes (Carbon Nanotechnologies Inc., Houston, Tex., USA) and multi-walled carbon nanotubes (Nano-lab Inc., Newton, Mass., USA) used in this experiment were processed using known methods (Kim et al. 2006). The average length and diameter of the single-walled carbon nanotubes were 186 nm and 1.7 nm respectively, and the average length and diameter of the multi-walled carbon nanotubes were 376 nm and 19.0 nm respectively.

The carbon nanotube solutions were treated with five cycles of 1.5 min of ultrasound at a power of 3 W followed by 0.5 min of rest, for a total of 10 minutes of interrupted ultrasound. A 150-µl aliquot of bacteria in suspension was incubated with 150 µL of CNT solution for 30 minutes at room temperature followed by 2 additional hours of incubation at room temperature. Labeled bacteria were centrifuged at 10,000 rpm for 5 min and the resulting pellet was resuspended in PBS.

Labeled 100-µl suspensions of *S. aureus* bacteria at a concentration of $5\times10^5$ cells/ml were injected into each mouse's tail vein, and the clearance of the labeled bacteria was monitored using PAFC measurements taken from 50-µm diameter microvessels in the ears of mice. Laser energy was delivered at a wavelength of 805 nm for the *S. aureus* that was labeled with ICG, and at a wavelength of 850 nm for the *S. aureus* that was labeled with CNTs. For both label types, the laser energy was delivered at a beam diameter of approximately 50 µm and at a fluence ranging between 20 and 50 mJ/cm$^2$.

Figure 7:
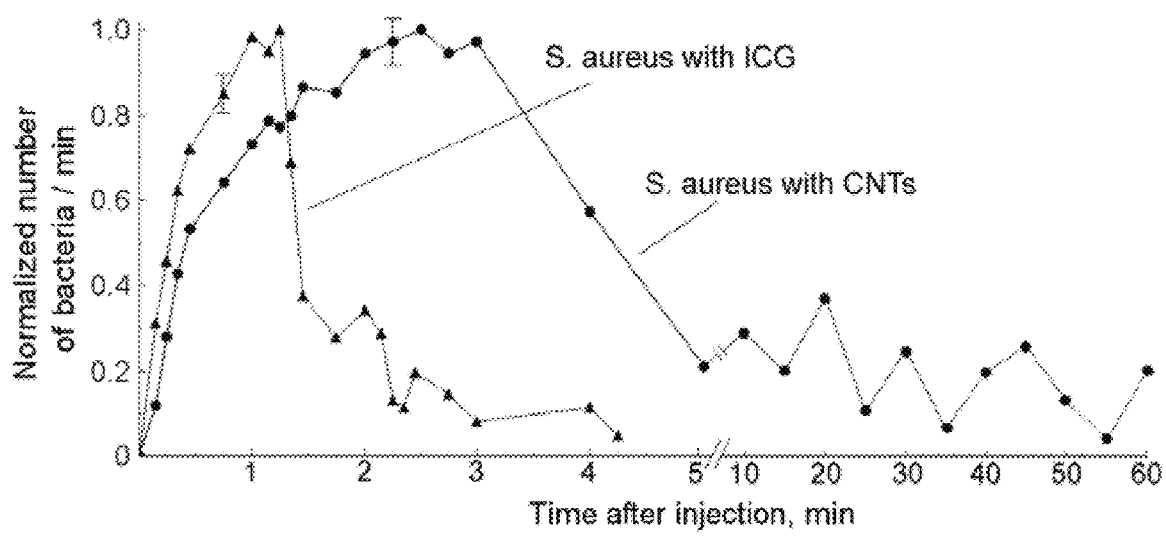
FIG. 7 is a graph of the normalized number of circulating *S. aureus* bacteria in blood microvessels of the mouse ear as a function of post-injection time, for bacteria labeled using two different contrast substances, ICG dye and carbon nanotubes (CNTs).

*S. aureus* bacteria labeled with ICG and CNT contrast substances yielded comparable results as summarized in FIG. 7. After injection of labeled *S. aureus*, the prototype PAFC device detected a rapid appearance of bacteria in the ear blood microvessels within the first minute, followed by a steady elimination of the bacteria from the blood circulation over the next 3-5 minutes. Periodic PAFC monitoring of mice blood vessels over the next few days revealed that very rare bacteria labeled with CNT or possibly unattached CNT continued to appear at an average rate of one PA signal every three minutes, and the labeled bacteria or CNT was not completely cleared from circulation until about 60 hrs after the initial injection (data not shown).

The results of this experiment established the feasibility of PAFC for the in vivo monitoring of individual cells in the circulatory systems of living organisms. Using appropriate contrast enhancement substances, the laser fluence required for effective detection of cells in circulation was well below the threshold levels for laser-induced cell damage.

Example 5. Detection of *E. coli* Bacteria Circulating in Mice Using Prototype In Vivo Photoacoustic Flow Cytometry System To demonstrate the ability of the prototype photoacoustic flow cytometry (PAFC) system to detect bacteria cells in vivo under biological conditions, the following experiment was conducted. The prototype PAFC system, previously described in Example 2, was used to detect the *E. coli* bacteria strain K12 in the circulation of nude mice.

The mouse ear model described in Example 2 was used for all measurements of circulating bacteria in the experiments described below. Because the endogenous light absorption of *E. coli* bacteria was relatively weak compared to the absorption of other blood components in the NIR spectral range, the bacteria were labeled with NIR-absorbing carbon nanotube (CNT) markers.

The *E. coli* K12 strain was obtained from the American Type Culture Collection (Rockville, Md.) and maintained in Luria-Bertani (LB) medium consisting of 1% tryptone, 0.5% yeast extract, and 0.5% NaCl in aqueous solution at a pH of 7. A 100-µl aliquot of *E. coli* in PBS was incubated with 100 µL of the CNT solution as described in Example 4 for 60 min at room temperature.

Figure 8:
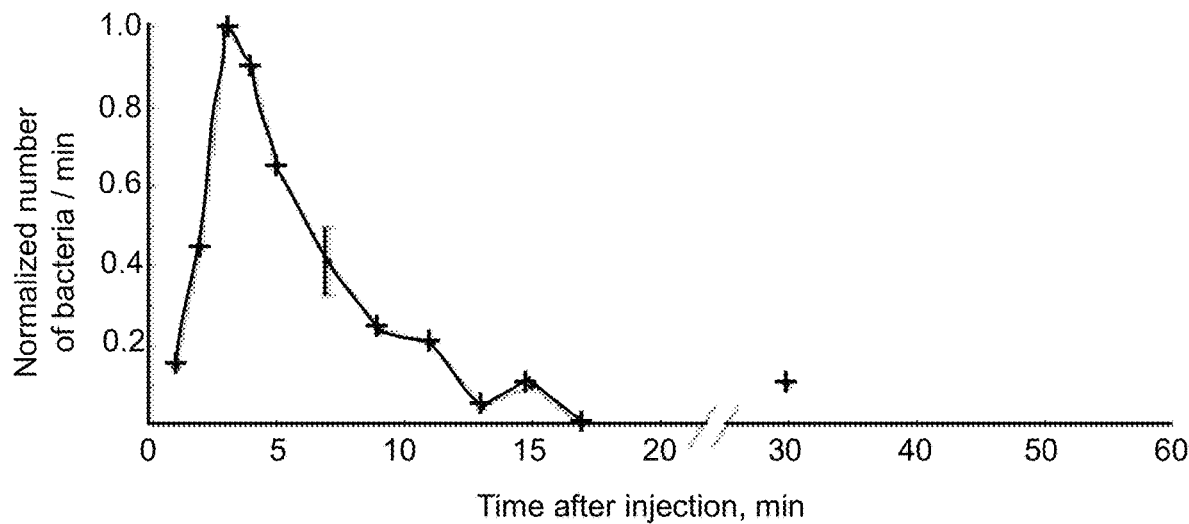
FIG. 8 is a graph of the normalized number of circulating *E. coli* bacteria in blood microvessels of the mouse ear as a function of post-injection time.

100-µl suspensions of CNT-labeled *E. coli* bacteria at a concentration of $5\times10^5$ cells/ml were injected into each mouse's tail vein, and the clearance of the labeled bacteria was monitored using PAFC measurements taken from 50-µm diameter microvessels in the ears of the mice. Laser energy was delivered at a wavelength of 850 nm, a beam diameter of approximately 50 µm and at a laser fluence of 100 mJ/cm$^2$. PAFC measurements, summarized in FIG. 8, detected a rapid appearance of the bacteria in circulation after injection, and the bacterial concentrations in the blood decreased exponentially over the next 15-17 minutes.

The results of this experiment confirmed the feasibility of PAFC for the in vivo monitoring of individual cells in the circulatory systems of living organisms. The laser fluence required for effective detection of *E. coli* cells in circulation was well below threshold levels for laser-induced cell damage.

Example 6. Detection of Circulating Exogenous Melanoma Cells Using Prototype In Vivo Photoacoustic Flow Cytometry System To demonstrate the ability to use the prototype in vivo PAFC device to detect unlabeled melanoma cells in circulation with extremely high sensitivity through skin cells with varying levels of melanin pigmentation, the following experiment was conducted.

B16F10 cultured mouse melanoma cells (ATCC, Rockville, Md.) were maintained using standard procedures (Ara et al. 1990, Weight et al. 2006, Zharov et al. 2006), including serial passage in phenol-free RPMI 1640 medium (Invitrogen, Carlsbad, Calif.) supplemented with 10% fetal bovine serum (FBS, Invitrogen). For comparison to the detection of unlabeled melanoma cells, the endogenous NIR cell absorption was increased by staining with ICG (Akorn Inc., USA), a strongly absorbent dye in the NIR range, for 30 min at 37° C. and in the presence of 5% $CO_2$. No toxicity was observed after labeling as assessed using the trypan blue exclusion assay (data not shown).

Figure 9:
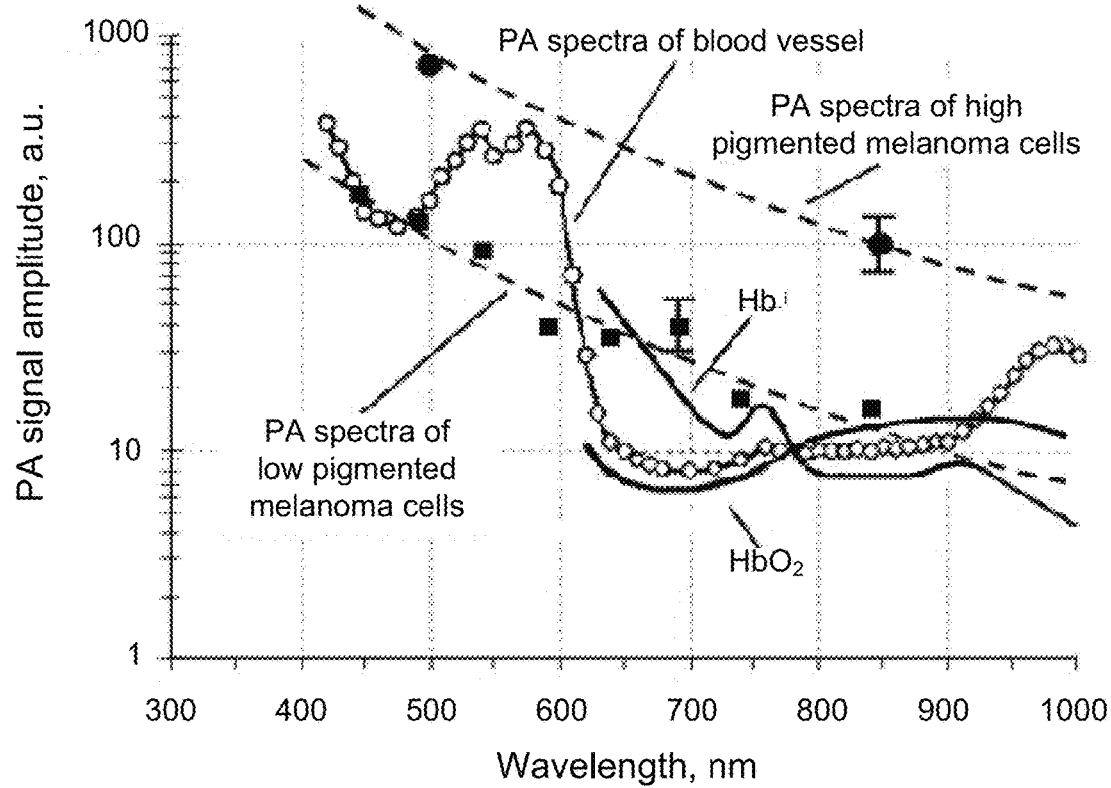
FIG. 9 shows the PA spectra of 50-µm mouse ear veins (empty circles), conventional absorption spectra of the B16F10 mouse melanoma cells with strong pigmentation (upper dashed curve) and weak pigmentation (lower dashed curve), spectra normalized using PA signals for the single mouse melanoma cells with strong pigmentation (black circles) and weak pigmentation (black squares), and absorption spectra for pure Hb and $HbO_2$ (fragments of solid curves in the spectral range 630-850 nm).

In vivo measurements of melanoma cells used the PAFC system previously described in Example 2 with a laser wavelength of 850 nm and a laser fluence of 80 mJ/cm$^2$. This wavelength was within a region in which the absorbance of melanoma cells is relatively high compared to the absorbance of hemoglobin, a major component of blood, as determined by in vitro measurements summarized in FIG. 9.

To estimate the influence of endogenous skin melanin on PAFC detection limits, Harlan Sprague mice, strain NIH-BG-NU-XID were used in this experiment. Female mice of this strain possess high levels of skin pigmentation between 8 and 10 weeks of age. The mice were anaesthetized and placed on a heated microscope stage as previously described in Example 2.

A 200-μl volume of saline solution containing approximately $10^5$ mouse melanoma cells was injected into the mouse circulatory system through a tail vein and then monitored using the PAFC system. The number of melanoma cells per minute detected using PAFC for melanoma cells after injection are summarized in FIG. 10 for melanoma cells in mice with low melanin content (FIG. 10A) and for melanoma cells in mice with high melanin content (FIG. 10B). In the first 5 minutes of PA detection following intravenous injection of cultured mouse melanoma cells, 600±120 PA signals (representing melanoma cells) per hour were observed, and the rate of detection of melanoma cells steadily decreased over the subsequent 20-30 min. Approximately 20 cells/hour and 4 cells/hour were detected after 24 h and 48 h of monitoring, respectively. The initial PA signal rate after the injection of melanoma cells stained with ICG contrast enhancement substances was 720±105 cells/hour (data not shown). Assuming that all stained melanoma cells were detected by in vivo PAFC, 82.4% of the unlabeled melanoma cells in circulation were detected by in vivo PAFC measurements.

The results of this experiment demonstrated the ability of the prototype in vivo PAFC device to detect and monitor the appearance and progression of metastatic melanoma cells in circulation non-invasively.

Example 7. Detection of Circulating Spontaneous Metastatic Cells During Tumor Progression Using the Prototype In Vivo PAFC Device An experiment was conducted to determine the ability of the prototype in vivo PAFC device to detect relatively scarce endogenous metastatic melanoma cells circulating in lymph vessels. The PAFC system described in Example 2 was used to monitor endogenous metastatic melanoma cells in mice. The laser characteristics used in this experiment are identical to those described in Example 6.

Nude mice were anaesthetized and placed on the heated microscope stage as previously described in Example 2. The ear blood vessels under examination were located 50-100 μm deep and had diameters of 35-50 μm with blood velocities of 3-7 mm/sec. To increase the probability of detection of rare metastatic cells, blood vessels with relatively large diameters of 150-300 μm and flow velocities up to 10-30 mm/s in the skin of the abdominal wall were examined using a customized skin fold chamber.

50-μl suspensions containing $10^6$ B16F10 cultured mouse melanoma cells (ATCC, Rockville, Md.) were subcutaneously injected into nude mice. Melanoma tumors subsequently formed in the ears of the mice and in the skin on the backs of the mice. PAFC was performed on ear and abdominal blood vessels to monitor the circulatory system for the appearance of metastatic cells. PA mapping was used to monitor the growth of tumors.

During ear tumor development, individual or groups of melanoma cells were first detected in the skin area close to the tumor site on the sixth day following tumor inoculation using PA mapping measurements. PA mapping measurements utilized PA signals derived by scanning a focused laser beam with diameter of 10 μm across each mouse's ear. Metastatic cells first appeared in ear microvessels near the tumor on the twentieth day after inoculation at a rate of 12±5 cells/hour (data not shown). Surprisingly, during the same time period, no melanoma cells were detected in the abdominal skin blood vessels. 25 days after inoculation, the average count of melanoma cells detected in the ear veins increased to 55±15 cells/hour. At this same time, melanoma cells were detected in abdominal wall skin vessels at a rate of 120±32 cells/hour. Thirty days after inoculation, the detection rate decreased to 30±10 cells/hour in the abdominal vessel, which may be attributed to inhibition of metastatic cell production in the primary tumor. PA mapping of selected tissue and organs revealed multiple micrometastases in cervical and mesenteric lymph nodes, as well as in lung and liver tissues.

PAFC measurements of the nude mouse back tumor model revealed the appearance of metastatic melanoma cells in abdominal skin blood vessels close to the tumor site on day 5, much earlier than in the tumor ear model. This indicates a much greater likelihood of detecting the initial metastatic process in the vicinity of the primary tumor.

Thirty days after tumor inoculation, the average concentration of melanoma cells was 150±39 cells/ml, corresponding to a circulating rate of approximately 4-10 cells/min in a 50-mm blood vessel and a flow velocity of 5 mm/s. The ultimate PAFC threshold sensitivity of the nude mouse back tumor model was estimated as 1 cell/ml. This circulating rate corresponded to an incidence of approximately one melanoma cell among 100 million normal blood cells.

The results of this experiment indicated that in vivo PAFC and PA mapping were sensitive methods with which to monitor the development of metastasized melanoma cells non-invasively, with high sensitivity and accuracy.

Example 8. Detection of Spontaneous Metastatic Cells in Lymphatic Vessels During Tumor Progression Using the Prototype In Vivo PAFC Device To determine the feasibility of detecting individual metastatic cells in lymph flow, the following experiment was conducted. A photoacoustic flow cytometer (PAFC) was used to monitor lymph flow for the presence of WBC, RBC, and metastatic melanoma cells.

The animal models used in this experiment were nu/nu nude mice, weighing 20-25 g (Harlan Sprague-Dawley). PAFC measurements were obtained using the lymphatic vessels in the ears using a heated platform as describe\d in Example 2. Melanoma tumors in the ear and back skin of the mice were induced by the subcutaneous injection of B16F10 mouse melanoma cells as described in Example 6.

To locate the lymphatic vessels in the mouse ear, a PA mapping process using a PA contrast agent was used. Ethylene blue (EB) dye, commonly used for lymphatic research, was injected into the lymphatic vessel walls. A 639 nm laser beam was then used to illuminate the lymphatic vessel, corresponding to the maximum absorption wavelength of EB dye, and the resulting PA signal emitted by the EB dye was monitored. The position of the laser beam on a lymph vessel was fixed when the PA signal amplitude reached its maximum at the laser wavelength of 639 nm.

Figure 11:
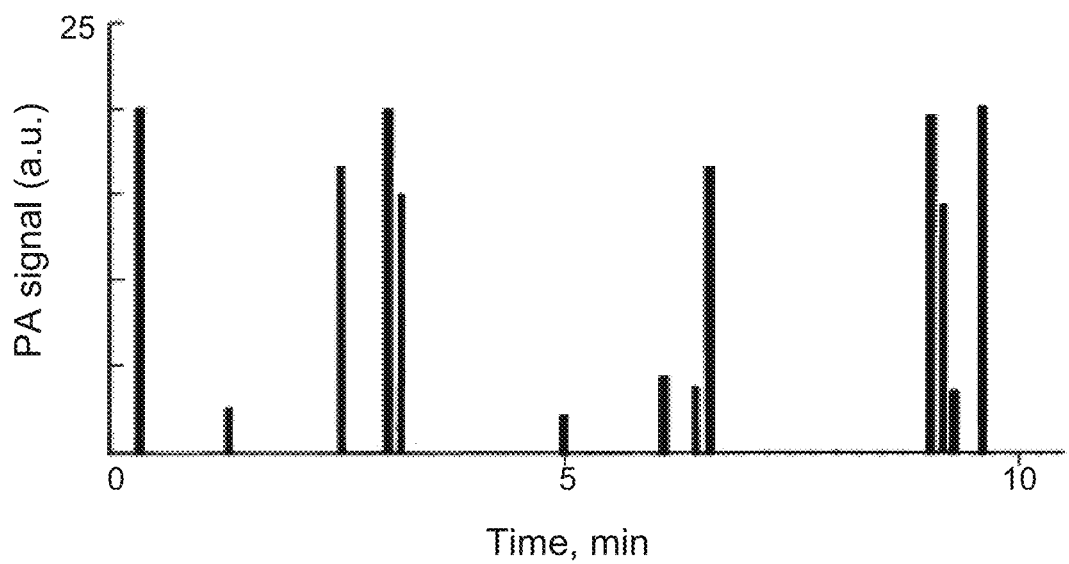
FIG. 11 is a summary of the PA signal rates from single melanoma cells detected in a mouse ear lymph microvessel 5 days after tumor inoculation.

In vivo PAFC detection of unlabeled melanoma cells relied on melanin as an intrinsic cell marker, as in Example 7. Melanoma cells were detected using a laser wavelength of 850 nm, a laser fluence of 35 mJ/cm$^2$, and a laser beam diameter of approximately 50 μm. In mice with induced skin melanomas, metastatic cells were observed to appear in a lymphatic vessel of the mouse's ear on the fifth day after inoculation at a rate of 1.2±0.5 cells/min, which steadily increased over the course of 2 weeks (data not shown). In mice with a melanoma tumor in the ear, melanoma cells appeared in skin lymphatics 20 days after inoculation. 30 days after inoculation strong PA signals detected the presence of metastatic melanoma cells in the sentinel lymph nodes, which was later confirmed by histology (data not shown). FIG. 11 shows the PA signals detected from single metastatic melanocytes circulating in the lymphatic vessel in the mouse ear five days after tumor inoculation.

The results of this experiment demonstrated the feasibility of detecting relatively scarce metastatic melanoma cells circulating in the lymphatic system using in vivo PAFC techniques, with high sensitivity and accuracy.

Example 9. Detection of Red Blood Cells and Lymphocytes Simultaneously Circulating in Lymph Vessels Using Prototype In Vivo PAFC Device To determine the feasibility of detecting unlabeled individual cells of different types circulating in lymph flow, the following experiment was conducted. A photoacoustic flow cytometer (PAFC) was used to monitor lymph flow for the presence of red blood cells and lymphocytes.

The animal models used in this experiment were 150-200 g rats (Harlan Sprague-Dawley). PAFC measurements were taken using lymphatic vessels in the mesentery of the rat, using the method described in Example 3. Lymphatic vessels were located, and the laser was focused on the lymphatic vessel using the methods described in Example 8.

Spectroscopic studies in vitro revealed that PA signals from lymphocytes reached maximal amplitude in the visible-spectral range near 550 nm, associated with cytochrome c acting as an intrinsic absorption marker (data not shown). Background PA signals from vessels and surrounding tissues were approximately 4-6-fold less than from single lymphocytes at this wavelength due to the low level of background absorption and laser focusing effects.

Figure 12:
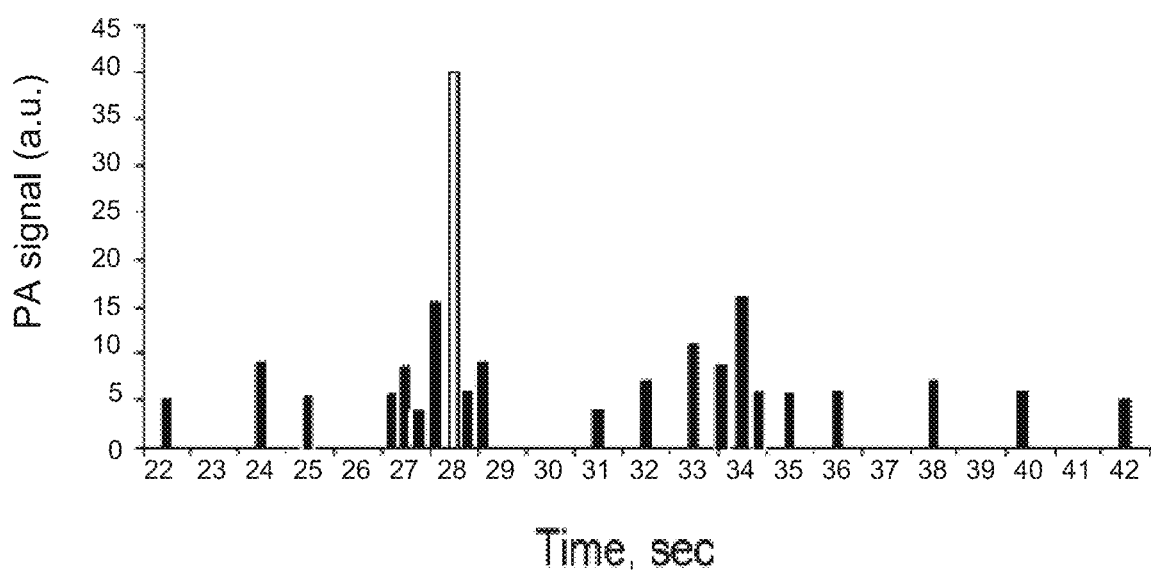
FIG. 12 is a summary of the PA signal rates from a single RBC (white bar) and lymphocytes (black bars) detected by PAFC in the lymph flow of rat mesentery.

The prototype in vitro PAFC system described in Example 2 was used to detect circulating cells in the lymphatic vessels of the rat mesentery. The laser used in the PAFC system had a wavelength of 550 nm and a fluence of 100 mJ/cm$^2$, and a circular beam diameter of approximately 50 μm. The cell detection rate obtained in lymphatic vessels was 60±12 cells/min. A graph showing the PA signals detected by the PAFC system in a rat mesentery lymphatic vessel is shown in FIG. 12. Lymphocyte heterogeneity resulted in 2-2.5-fold fluctuations in PA signal amplitude from cell to cell. A small fraction of the detected cells had strong PA signal amplitudes exceeding those of the lymphocyte signals by a factor of 10 to 20-fold. One such strong PA signal is shown as a white bar in FIG. 12 at 28 seconds. Subsequent spectral and imaging analysis identified rare single red blood cells (RBCs) as the sources of these excessively strong PA signals.

The results of this experiment demonstrated that the in vivo PAFC system possessed sufficient sensitivity and accuracy for the simultaneous detection of red blood cells and lymphocytes circulating in the lymphatic vesicles.

Example 10. Detection and Identification of 3 Different Exogenously Labeled Cell Types in Circulation within Lymph Vessels Using a Prototype In Vivo Two-Wavelength PAFC Device To demonstrate the ability of the photoacoustic flow cytometry (PAFC) system to detect cells using more than one wavelength of laser pulse, the following experiment was conducted. In this experiment, a PAFC system was used to detect exogenous blood cells that were labeled with three different nanoparticles, while circulating in lymphatic vessels. The PAFC system detected the cells by illuminating the cells with laser pulses of two different wavelengths in the near-infrared (NIR) spectrum.

A PAFC system similar to that described in Example 2 was used to detect the circulating cells. However, in the PAFC system used in this experiment, the laser of the PAFC system pulsed light at two different wavelengths, corresponding to the wavelengths of maximum absorption for two of the nanoparticles used to label the cells. The first laser pulse was at a wavelength of 865 nm, a laser fluence of 35 mJ/cm$^2$, and pulse duration of 8 ns. 10 μs after the end of the first laser pulse, a second laser pulse was delivered at a wavelength of 639 nm, a laser fluence of 25 mJ/cm$^2$, and pulse duration of 12 ns. The paired laser pulses were repeated at a frequency of 10 Hz.

The animal models used in this experiment were nu/nu nude mice, weighing 20-25 g (Harlan Sprague-Dawley). PAFC measurements were taken using lymphatic vessels in the mesentery of the mouse, using the methods described in Example 3. Lymphatic vessels were located, and the laser was focused on the lymphatic vessel using the methods described in Example 8.

Normal fresh blood cells were obtained from heparinized whole-blood samples of donor mice after terminal blood collection. Red blood cells were isolated by simple centrifugation, and lymphocytes were isolated by Histopaque (Sigma-Aldrich) density gradient centrifugation as recommended by the supplier.

The nanoparticles used to label the various blood cells used in this experiment were gold nanorods (GNRs) and gold nanoshells (GNSs), provided by The Laboratory of Nanoscale Biosensors at the Institute of Biochemistry and Physiology of Plants and Microorganisms in Saratov, Russia. The GNRs had an average diameter of 16 nm, an average length of 40 nm, and a relatively narrow absorption wavelength band of 660±50 nm. The GNSs had an average diameter of 100 nm, and a maximum absorption of wavelengths near 860 nm. Both the GNRs and GNSs were coated with polyethylene glycol using the process described in Example 3. Single-walled carbon nanotubes (CNTs; Carbon Nanotechnologies Inc.) with an average length of 186 nm and an average diameter of 1.7 nm were also used as markers; the CNTs absorbed laser energy over a wide range of wavelengths with an efficiency that monotonically decreases as wavelength increases (data not shown). All particles were in suspension at a concentration of about $10^{10}$ nanoparticles/ml.

Live neutrophils were labeled with the GNSs, live necrotic lymphocytes were labeled with the GNRs and apoptotic lymphocytes were labeled with the CNTs. The cells were labeled by incubating 100-μl aliquots of each cell type in phosphate-buffered saline with 100 μL of CNTs, GNRs, or GNSs for 15 min at room temperature.

The labeled cells, mixed in approximately equal proportions, were intravenously injected into the tail vein of the mouse. About six hours after injection, mesenteric lymphatics were illuminated with two laser pulses at wavelengths of 865 nm and 639 nm as described above and using a preparation similar to that described in Example 3. PA signals were detected at a rate of 1-3 signals/min at this time.

The detected PA signals had one of three distinctive temporal shapes associated with the response of the three different labels to the paired laser pulses, as shown in FIG. 13. PA signals from necrotic lymphocytes marked with GNR were generated in response to the 639 nm laser pulse only, after a 10-μs delay, as shown in FIG. 13A. The apoptotic lymphocytes marked with GNS generated PA signals in response to laser pulse at a wavelength of 865 nm with no delay, as shown in FIG. 13B. Live neutrophils marked with CNT generated two PA signals after a 10-μs delay, as shown in FIG. 13C; one PA signal was generated in response to the 639 nm laser pulse, and the second PA signal was generated in response to the 850-nm laser pulse, due to comparable absorption by the CNT markers attached to the neutrophils at both wavelengths.

The results of this experiment demonstrated that labeling cells using a variety of contrast substances having different wavelength absorption characteristics and illuminating the cells using two laser pulse wavelengths enabled the prototype in vivo PAFC device to detect and discriminate between live neutrophils, necrotic lymphocytes, and apoptotic lymphocytes circulating in the lymphatic vessels. This method may potentially be extended to unlabeled cells circulating in the lymphatic or circulatory systems, using two or more unique laser pulse wavelengths selected to generate a unique PA signal shape for each cell type to be detected.

Example 11. Spatial Resolution and Maximum Detectible Vessel Depth of the Prototype in Vivo PAFC System To determine the maximum spatial resolution and maximum detectible vessel depth of the prototype PAFC system, the following experiment was conducted. The prototype PAFC system described in Experiment 2 and the mouse ear model described in Example 7 were used to detect mouse melanoma cells injected into the tail veins of nude mice as described in Example 7.

The prototype PAFC system achieved a lateral resolution of 5-15 μm when detecting melanoma cells circulating in mouse ear blood vessels with vessel diameters of 10-70 μm at depths of 50-150 μm below the surface of the skin. However, when melanoma cells circulating in mouse ear blood vessels at a depth of 0.5 mm were measured, the lateral resolution decreased to 30-50 μm due to the scattering of the 850 nm laser pulses by the additional tissue between the PAFC laser and the targeted blood vessels.

The maximum depth at which the PAFC system was capable of detecting cells circulating in deep vessels was estimated by overlaying layers of mouse skin of varying thickness over intact mouse skin containing peripheral blood vessels at a depth of approximately 0.3 mm below the surface of the intact skin. Using the PAFC system with an unfocused ultrasound transducer (Panametrics model XMS-310, 10-MHz), PA signals were detected at total skin thicknesses up to approximately 4 mm, with a 27-fold signal attenuation due to light scattering. When a focused ultrasound transducer was used (Panametrics model V316-SM, 20 MHz, focal length 12.5 mm), PA signals were detected from melanoma cells circulating in the mouse aorta at a depth of approximately 2.5 mm; a laser pulse wavelength of 850 nm was used to illuminate the melanoma cells. At a total tissue depth as high as 11 mm, the PA signals emitted by circulating metastatic melanoma cells illuminated by 532 nm laser pulses remained discernible from the background PA signals emitted by surrounding tissues. The lateral resolution at this vessel depth, measured by varying the angle of the ultrasonic transducer, was estimated to be approximately 250 μm (data not shown).

The results of this experiment demonstrated that the PAFC system was capable of detecting circulating melanoma cells at a vessel depth of up to 11 mm with a resolution of approximately 250 μm. This resolution may be improved significantly through the use of higher frequency ultrasound transducers such as 50 MHz transducers.

Example 12. Assessment of the Spatial Resolution of a Prototype In Vivo PAFC Device at Varying Skin Pigmentation Levels To determine the sensitivity of the prototype PAFC system to the level of skin pigmentation, the following experiment was conducted. The PAFC device described in Example 2 was used to measure PA signals from blood vessels in nude mice skin with low and high levels of pigmentation using methods similar to those described in Example 7.

In the low-pigmented nude mouse model, the background PA signal from skin cells was relatively weak. PA signals measured by a high frequency ultrasound transducer (Panametrics model V-316-SM, 20 MHz) resulting from the simultaneous irradiation of two circulatory vessels at depths of approximately of 0.3 mm and 2.4 mm, were determined to have a time separation of approximately 1.4 ms. This delay is consistent with signals emitted by cells with a separation distance of 2.1 mm, assuming a velocity of sound in soft tissue of approximately 1.5 mm/ms. Similar results were obtained for measurements of circulatory vessels in the highly pigmented nude mouse model (data not shown).

The results of this experiment demonstrated that the level of skin pigmentation did not significantly impact the spatial resolution of the PAFC device. For strongly pigmented skin, the assessment of deeper vessels may be enhanced because the skin pigmentation may facilitate the discrimination between PA signals from circulating individual cells and PA signals from the skin.

Example 13. Enrichment of Circulating Metastatic Cells in the Mouse Ear Model

To determine the feasibility of novel methods for increasing the concentrations of circulating metastatic cells detected by the in vivo PAFC device, the following experiment was conducted. Using the mouse ear model to measure the incidence of circulating metastatic melanoma cells, as described in Example 7, the effect of gentle mechanical squeezing of blood microvessels was assessed. This method of enriching the local incidence of rare circulating cancer cells in vivo exploited the size differences between melanoma cells (16-20 mm), WBC (7-8 mm), and RBC (5-6 mm) and the high deformability of RBC compared to cancer cells. The lumen size of the microvessel was decreased to 10-15 μm through gentle mechanical squeezing of blood microvessels in 50-μm microvessels of mouse ear. After squeezing a 50-μm mouse ear blood vessel for 10 min, then quickly releasing the vessel, the rate of metastatic melanoma cells measured by PAFC immediately after vessel release increased approximately 8-fold, relative to the rate measured before squeezing. The degree of blood vessel squeezing could be controlled by monitoring increases and decreases in PA signal amplitudes.

The results of this experiment demonstrated that local enrichment of circulating metastatic melanoma cells was achieved through the mechanical restriction of circulatory vessels.

Example 14. Manipulation of the Background Absorption by Surrounding Blood Cells Using Variations in Blood Oxygenation, Hematocrit, and Blood Osmolarity To determine the effects of changes in blood oxygenation, hematocrit, and osmolarity on the background absorption of blood cells during in vivo PAFC, the following experiment was conducted. The absorption of laser energy by hemoglobin in its oxygenated ($HbO_2$) and deoxygenated (Hb) forms differs, depending on the oxygen saturation state of the hemoglobin and the wavelength of the laser pulse. The total absorption of red blood cells decreases as oxygenation increases for laser pulse wavelengths 810-900 nm, and the absorption of red blood cells decreases with increasing blood oxygenation at laser pulse wavelengths of 650-780 nm (data not shown). Thus, the oxygenation of the red blood cells may be manipulated to reduce the background PA signals produced by red blood cells.

Pure oxygen was delivered to a mouse using a mask around the mouse's head, and the background PA signal obtained before and after the increased blood oxygenation was measured using the in vivo PAFC system described in Example 2. The increased blood oxygenation resulting from the exposure of the mouse to pure oxygen for 15 minutes caused the background PA signal from veins to decrease by a factor of 1.36±0.14, using a laser pulse wavelength of 750 nm. Replacing the delivery of pure oxygen with the delivery of pure nitrogen led to a 35% decrease in background PA signal in an arteriole at a laser pulse wavelength of 900 nm.

Another experiment was conducted to assess the effects of decreasing the density of the circulating RBC as measured by the hemotocrit on the background signal from circulating red blood cells. The hemotocrit of a mouse's blood was temporarily reduced by the intravenous injection of 0.5 ml of standard saline solution into the vein tail. After the saline injection, PA signals from a 50-μm ear mouse vein dropped by a factor of 2.3±0.3, and returned to near-initial levels within about 1.5 minutes.

Changes in blood osmolarity induced an increase in the RBC volume (swelling) that resulted in a decrease in the average intracellular Hb concentration. Injection of 100-mL of hypertonic NaCl solution into the mouse tail vein led to an approximately 2-fold decrease in the PA signal in the ear vein.

The results of these experiments demonstrated that the background PA signals resulting from the emission of PA signals by red blood cells may be reduced by manipulation of the chemical environment of the blood, including blood oxygenation, hemotocrit, and blood osmolarity. These approaches may be readily applicable to human subjects because the procedures used in this experiment are routinely performed in clinical practice.

Example 15. Assessment of Microbubbles Conjugated with Nanoparticles as PAFC Contrast Agents To assess the effectiveness of microbubbles conjugated with nanoparticles as a contrast agent in PAFC, the following experiment was conducted. Microbubbles (Definity Inc.) with average diameters of 2-4 μm were incubated with PEG-coated gold nanoshells (GNS), previously described in Example 10, for 1 hr at room temperature. The measurement of PA signals in vitro, as described in Example 1, was conducted for microbubbles only, for unconjugated GNSs, and for microbubbles conjugated with GNSs. The microbubbles conjugated with GNSs emitted the strongest PA signals, the unconjugated GNSs emitted somewhat weaker PA signals, and the microbubbles alone emitted negligible PA signals (data not shown).

Increasing the energy of the laser pulses illuminating the GNS-conjugated microspheres led to a dramatic increase of the emitted PA signals, followed by the disappearance of the microbubbles after a single laser pulse. This observation was attributed to the laser-induced overheating of the GNSs leading to a dramatic temperature increase of the gas trapped inside of the microbubbles that ultimately ruptured the microbubbles.

The results of this experiment demonstrated that microbubbles conjugated with GNS were an effective contrast agent, but that the energy of the laser pulses may be constrained to avoid bursting the microbubbles. Because the microbubbles may be selectively attached to blood clots or taken up by activated white blood cells, this contrast agent may expand the potential applications of in vivo PAFC to include the detection of blood clots and certain activated white blood cells.

Example 16. Detection of Circulating Exogenous Melanoma Cells Using the Prototype Two-Wavelength In Vivo PAFC Device To demonstrate the ability to use two-wavelength in vivo PAFC to detect injected unlabeled melanoma cells in circulation with extremely high sensitivity, the following experiment was conducted. B16F10 cultured mouse melanoma cells (ATCC, Rockville, Md.) were obtained and maintained as described in Example 6. The experiments were performed using a nude mouse ear model similar, described in Example 2 (n=25). To mimic metastatic cells, approximately $10^5$ tumor-derived B16F10 cells in a 100-μl volume of saline solution were injected into the mouse circulatory system through a tail vein and then monitored in an ear vein using an apparatus and methods similar to those described in Example 10. An ear blood vessel was illuminated by two laser pulses at wavelengths of 865 nm and 639 nm with a 10-ms delay between the pulses.

The melanoma cells were distinguished from surrounding blood cells, based upon the distinctive absorption spectra of the melanoma cells, as described previously in Example 6 and summarized in FIG. 9. Melanoma cells emitted two PA signals with a 10-ms delay in response to each pair of laser pulses. The first PA signal, induced by the 639 nm laser pulse, had a higher amplitude than the PA signal induced by the 865 nm pulse, as shown in FIG. 14A. Red blood cells, the most numerous blood cells in circulation, generated two PA signals with lower amplitudes than the corresponding PA signals generated by the melanoma cells. In addition, for the red blood cells, the amplitude of the PA signal induced by the 865 nm pulse was slightly higher than the PA signal induced by the 639 nm laser pulse, as shown in FIG. 14B.

The PA signals corresponding to the melanoma cells were cleared over a two-hour period following the injection, as shown in FIG. 15.

Based on comparisons to similar data measured for melanoma cells labeled with markers that emitted strong PA signals, it was estimated that approximately 89% of the unlabeled melanoma cells were detected (data not shown). This percentage was lower than that found in previous in vitro studies (96%) and indicated a false-negative-signal rate of 1.5 cells/min related to the background signals of RBCs (data not shown). Longer-term monitoring of PA signals from ear blood vessels without prior melanoma cell injection detected no false-positive signals using a signal-to-noise ratio in excess of 2 as a false-positive criterion, where the signal noise was associated with fluctuations of laser energy produced by the PAFC device and the density of red blood cells in the detected volume.

The results of this experiment demonstrated that two-color in vivo PAFC was an effective method for detecting metastatic melanoma cells in circulation. It was estimated that the method described above detected approximately 89% of the melanoma cells in circulation, with slightly lower detection rates due to skin pigmentation.

Example 17. Detection of Circulating Spontaneous Metastatic Cells During Tumor Progression Using Two-Wavelength In Vivo PAFC An experiment was conducted to determine the ability of two-wavelength in vivo PAFC to detect relatively scarce endogenous metastatic melanoma cells circulating in lymph vessels. The PAFC system described in Example 10 was used to monitor endogenous metastatic melanoma cells in mice. Tumors were induced in nude mice by subcutaneous injections of melanoma cells using methods similar to those described in Example 7. Tumors formed and proliferated in the skin of the ears and the backs of the nude mice over a period of 4 weeks, as previously described in Example 7.

Figure 16:
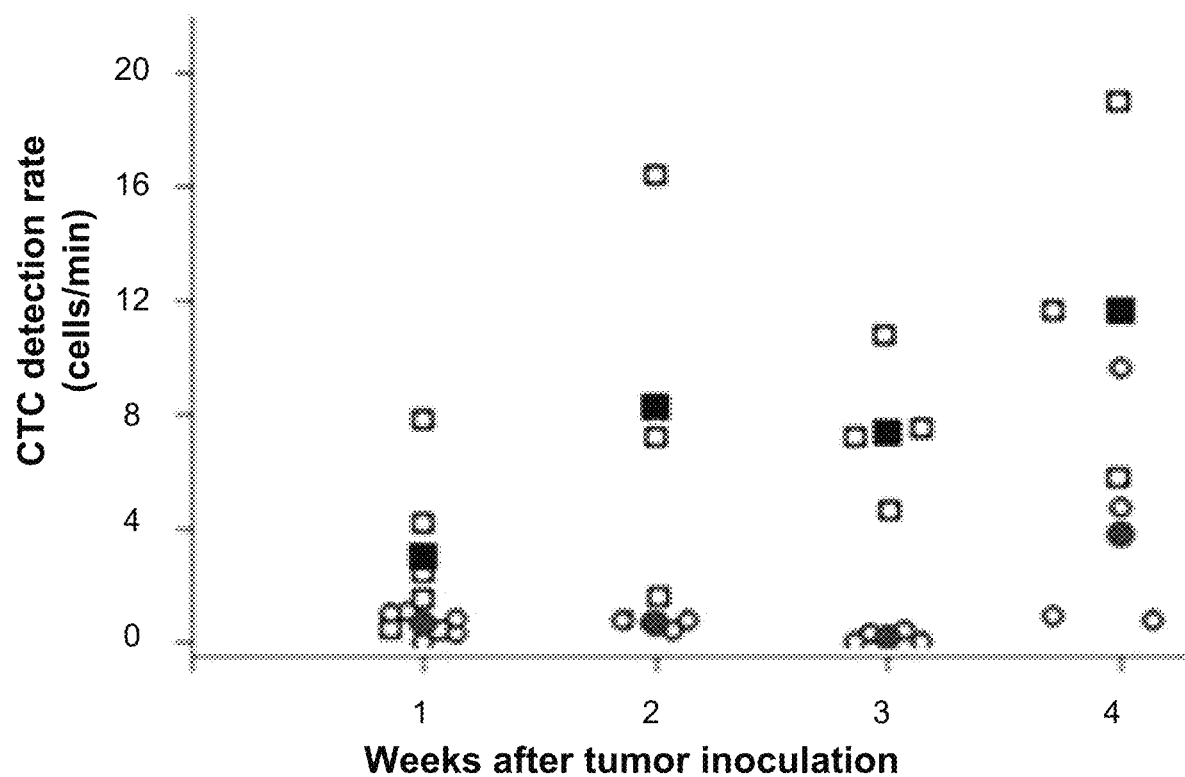
FIG. 16 is a summary of the PA signal rates from single melanoma cells detected in a mouse ear lymph microvessel 4 weeks after tumor inoculation.

PAFC was used to count spontaneous metastatic melanoma cells in an approximately 50 μm-diameter ear blood vessel and in a 100-200 μm-diameter skin blood vessel during tumor progression in the ear and skin of each mouse, as summarized in FIG. 16. As previously described in Example 7, the skin tumor growth rate was faster than that of the ear tumors, and metastatic melanoma cells appeared more quickly in the circulation, as indicated by the mean cell detection rate measured in the skin capillaries, shown as solid square symbols in FIG. 16. In particular, within the first week after the induction of the tumors, about 1-4 melanoma cells/min were detected in the skin vasculature, and as the tumor size increased, the rate of detection of metastatic melanoma cells gradually increased to about 7 cells/min and about 12 cells/min after 3 weeks and 4 weeks, respectively.

The results of this experiment indicated that two-wavelength in vivo PAFC was a sensitive method with which to monitor the development of metastasized melanoma cells non-invasively, with high sensitivity and accuracy.

Example 18. In Vitro Photoacoustic Response of Quantum Dot Markers Using Two-Wavelength PAFC Device An experiment was conducted to determine the ability of the two-wavelength PAFC device to detect quantum dot cell markers in vitro. The PAFC system described in Example 2 was used to measure photoacoustic pulses emitted by quantum dots in response to laser pulses with wavelengths of 625 nm, pulse widths of 8 ns, and laser fluences ranging 0.001-10 J/m$^2$. The laser beam used to pulse the quantum dots had a diameter of about 20-30 μm in the sample plane. Quantum dots were obtained commercially with a polymer coating as well as with a streptavidin protein coating (Qdot 655 nanocrystals, Invitrogen, Carlsbad Calif.). The quantum dots had diameters of about 15-20 nm and an emission wavelength of about 655 nm. Either single quantum dots or aggregations of quantum dots were diluted with a buffer of 2% BSA/PBS and mounted on a microscope slide within a fluid layer of less than 1 μm depth.

Figure 17:
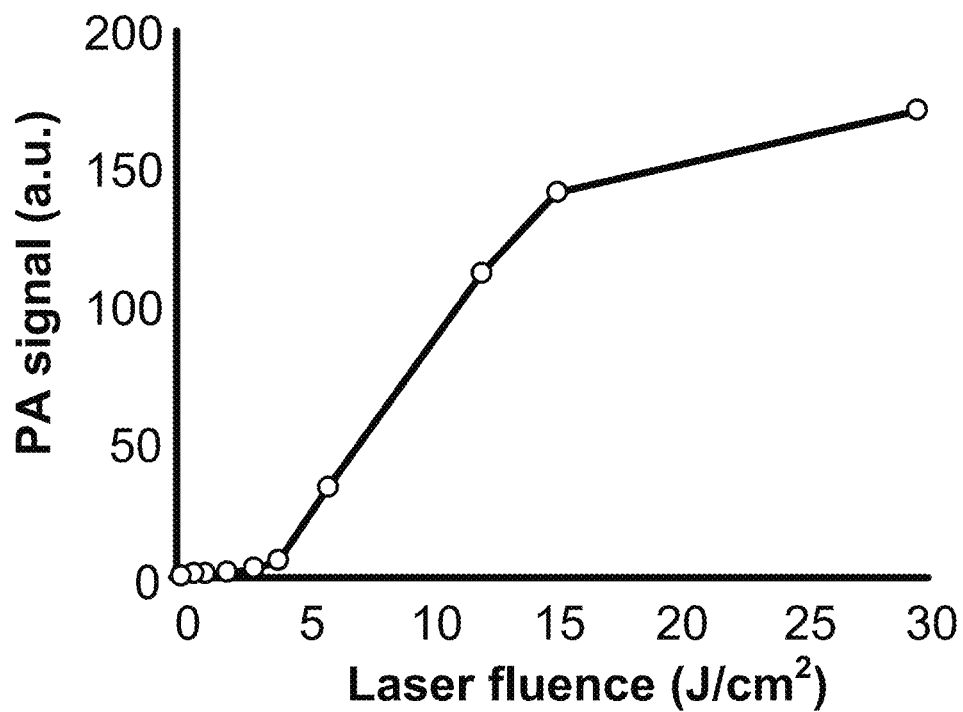
FIG. 17 is a summary of the PA signal amplitude generated by quantum dot markers as a function of laser fluence.

The two-wavelength PAFC system was used to pulse the quantum dot preparation with laser fluences ranging from 0.001-30 J/m$^2$. The magnitudes of the PA signals emitted by the quantum dots are summarized in FIG. 17. The quantum dot preparations had a non-linear PA signal response to the variations in laser fluences. PA signal amplitude gradually increased in the laser fluence range from 0.1-1 J/cm$^2$. Through the laser fluence range between 1.5-7 J/cm$^2$, the response increased dramatically in a non-linear manner, and continued to increase in magnitude up to a laser fluence of 15 J/cm$^2$. At laser fluences above 15 J/m$^2$, the responses of the quantum dot preparations were saturated.

Figure 18:
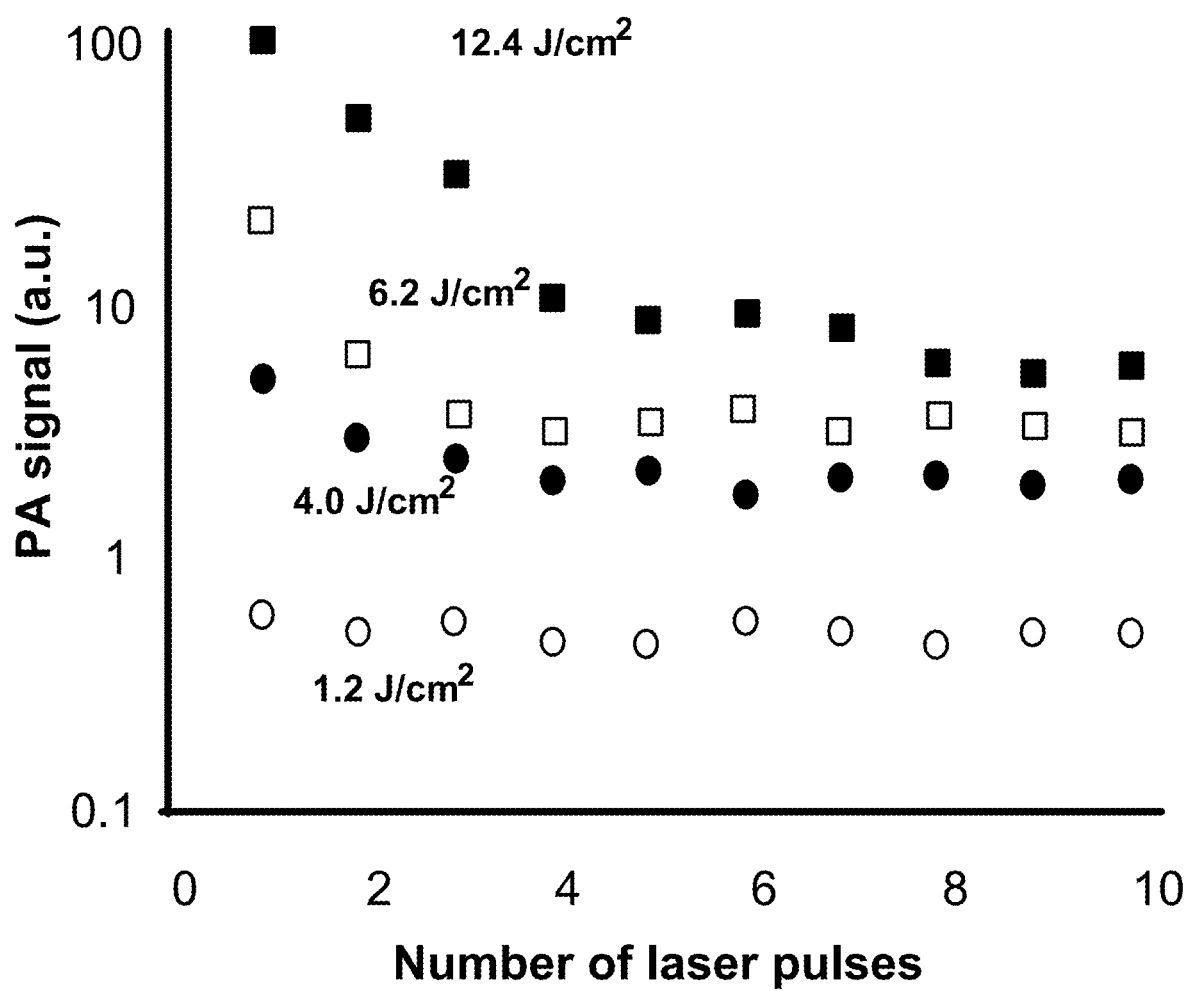
FIG. 18 is a summary of the PA signal amplitude generated by quantum dot markers as a function of the number of laser pulses.

The PA signal response was assessed as a function of the number of laser pulses for laser fluences of 1.2, 4.0, 6.2, and 12.4 J/cm$^2$, as summarized in FIG. 18. There PA signal was not significantly influenced by the number of laser pulses at laser fluences below about 3 J/cm$^2$, indicating no blinking behavior, unlike the stereotypical fluorescent blinking behavior observed in quantum dots. At higher laser fluences, significant decreases in the PA signal amplitude were observed due to an increase in the number of pulses, possibly due to laser induced melting or thermal-based explosion of the quantum dots.

The results of this experiment indicated the quantum dots generated strong PA signals in response to laser pulses.

Example 19. Detection of Blood Clots In Vitro Using a Negative Photoacoustic Contrast Detection Technique To demonstrate the ability of the prototype PAFC system to detect clots using a negative photoacoustic contrast technique, the following experiments were conducted.

Whole blood samples were obtained from healthy human donors in heparinized tubes. Platelet-rich plasma was prepared via centrifugation of the whole blood at an acceleration of 200 g for 6 min to remove red blood cells (RBCs). Washed platelets were prepared via centrifugation of platelet-rich plasma an acceleration of 1,000 g in the presence of prostacyclin (0.1 g/ml) for 10 min. The resulting pellet was re-suspended in PBS to the desired concentration. The aggregations of platelets were initiated with collagen introduced into a 0.5 mL aliquot of platelet-rich plasma.

To determine the wavelength of maximum contrast between the platelet aggregations and surrounding blood cells, a conventional absorption spectrum was obtained using a fiber spectrophotometer (USB4000, Ocean Optics Inc, USA). Light transmitted at different wavelengths through a platelet aggregation sample was collected through an ocular modified with a custom-made fiber connector. The resulting absorption spectrum is summarized in FIG. 19. The platelet absorption spectrum is shown compared with spectra obtained in a similar manner using a whole blood sample and using a suspension of gold nanorods. The maximum contrast of the platelets and the gold nanorods, defined in this experiment as the maximum difference between the PA signals generated by the platelets and the gold nanorods, occurred between pulse wavelengths between about 600 nm and about 750 nm.

The general layout of the PAFC system used for the detection of the platelet aggregations in these experiments was assembled on the technical platform of an inverted microscope (IX81, Olympus America, Inc.). This platform incorporated photothermal (PT), photoacoustic (PA), fluorescent, and transmission digital microscope (TDM) modules, as well as a tunable optical parametric oscillator (OPO, model Opolette HR 355 LD, OPOTEK, Inc., Carlsbad, Calif.). The optical parametric oscillator had a spectral range of 410-2500 nm, a pulse width of 8 ns, a pulse energy of up to 5 mJ, a pulse energy stability of 3-5%, a pulse repetition rate of 100 Hz, and a line width of about 0.5 nm. The pump laser energy was controlled with a power meter (PE10-SH, OPHIR, Israel). The PAFC system was further equipped with two high pulse repetition rate lasers: a) a sapphire (Ti:S) laser (model LUCE 820-10 kHz, Bright Solutions, Inc., Italy) with a wavelength of 820 nm, a maximum pulse energy of 78 µJ, a pulse width of 8 ns, and a pulse repetition rate of 10 kHz, and b) a solid laser (model QL671-500, Crystal Laser, Reno, Nev., USA) with a wavelength of 671 nm, a maximum pulse energy of 40 µJ, a pulse width of 24 ns, and a pulse repetition rate of up to 50 kHz.

To conduct photothermal detection, a collinear probe beam from a continuous wave stabilized He—Ne laser (Spectra model 117A; Physics Inc., USA; wavelength=633 nm, power=1.4 mW) was used to induce temperature-dependent variations of the refractive index around absorbing targets, causing defocusing of the laser energy via the thermo-lens effect. The resulting PT signal from the irradiated volume (a reduction in the beam's intensity at its center) was detected by a photodiode with a preamplifier (model PDA36A, ThorLabs Inc.) situated behind a pinhole. Photothermal imaging (PTI) in a scanning mode was provided by repositioning the samples to be imaged using a 3-dimensional (X-Y-Z) translation stage (model H117 ProScan II, Prior Scientific, Inc., USA) to an accuracy of 50 nm.

In addition, a customized photoacoustic (PA) module was included in the PAFC system that included an unfocused ultrasound transducer (model 6528101, Imasonic Inc., Besancon, France) with a detection frequency of up to 3.5 MHz and an amplifier (model 5660B, Panametrics-NDT, Olympus) with a maximum detection frequency of 5 MHz and a gain of 60 dB. Further, the PAFC system included a fluorescent imaging module (Olympus America, Inc.).

The processing and storage of the recorded PT and PA data was performed using a PC (model Precision 690 with a quadcore processor, 4 GB of RAM and Windows Vista 64-bit operating system, Dell Inc., Round Rock, Tex.) with a 200 MHz analog-to-digital converter digitizer board (model PCI-5124, 12-bit, 128 MB memory, National Instruments, Inc., Austin, Tex.). Synchronization of the OPO operation and signal acquisition, as well as control of the translation stage during scanning was implemented using a proprietary software module (LabView 8.5, National Instruments, Inc., USA). Data signals were also recorded using a Tektronix TDS 3032B oscilloscope.

Figure 21:
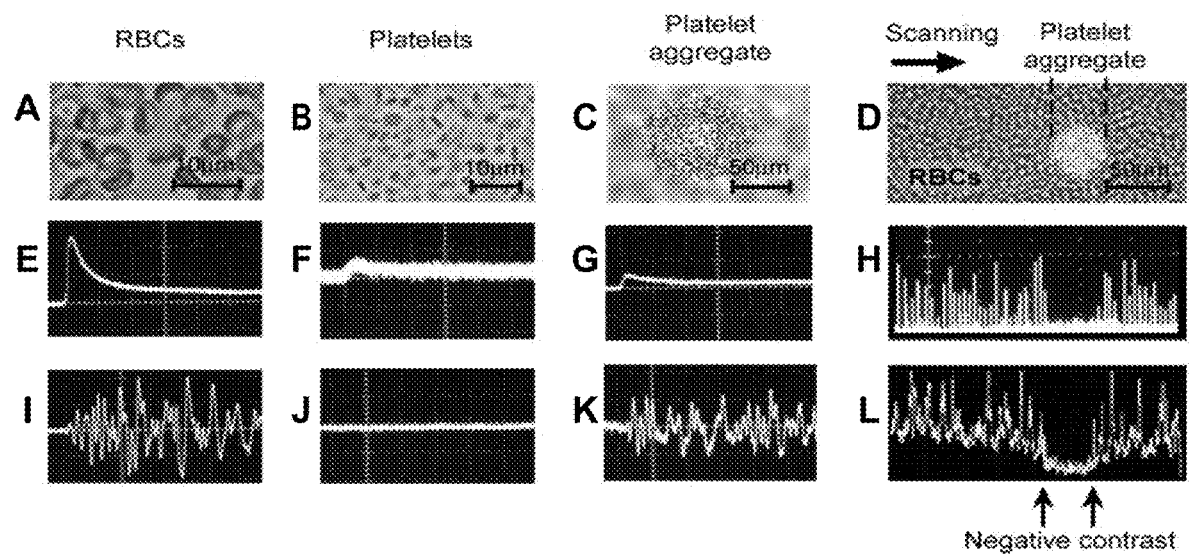
FIG. 21 includes a series of optical images of slides containing samples of red blood cells (FIG. 21A), non-aggregated platelets (FIG. 21B), a platelet aggregate (FIG. 21C), and a platelet aggregate among red blood cells (FIG. 21D).

To determine whether sufficient contrast existed between the platelet aggregates and the surrounding blood cells, slides containing samples of red blood cells, non-aggregated platelets, collagen-induced platelet aggregates in PBS, and collagen-induced platelet aggregates in whole blood were visualized using optical imaging (FIGS. 21A-21D, respectively), photothermal detection (FIGS. 21E-21H, respectively), and photoacoustic detection (FIGS. 21I-21L, respectively). For the photothermal and photoacoustic detection, the samples were scanned using a laser wavelength of 580 nm. Three different laser fluences were used depending on the sample: 10 mJ/cm$^2$ for the RBC sample, 9.5 J/cm$^2$ for the platelets in PBS, and 0.3 J/cm$^2$ for the platelet aggregation in the blood sample. The diameter of the laser spot used to illuminate the samples was 7±2 µm. Referring to FIG. 21L, the photoacoustic detection of a platelet aggregate surrounded by red blood cells was characterized by negative contrast, in which the amplitude of the photoacoustic (PA) signal produced by the platelet aggregate decreased to levels significantly less than the PA signal amplitudes produced by the surrounding red blood cells. Based on the distinct negative contrast of the PA signal produced by the platelet aggregation relative to the PA signal amplitude produced by the surrounding red blood cells, the platelet aggregates were identifiable based on PA imaging.

To determine if PA imaging could be used to determine the spatial extent of a platelet aggregate, a collagen-induced platelet aggregate with a size of about 20 µm was placed in a blood sample with a sample thickness of about 120 µm on a glass slide. The sample was scanned using PA scanning at a laser wavelength of 532 nm, a pulse repetition frequency of 100 Hz, and a pulse energy of 1.0 µJ. The diameter of the laser spot was about 5 µm and the scan was performed using translation intervals of 10 µm per step. The scan was repeated eight times and the results were averaged. The results of the photoacoustic scanning are summarized in FIG. 22. The PA signal obtained from the scan of a platelet aggregate with the size of about 20 µm exhibited a significant negative contrast relative to the background PA signals from the surrounding blood cells.

To assess the variation of the magnitude of the negative contrast of platelet aggregates as a function of the size of the aggregate, collagen-induced platelet aggregates with sizes ranging from about 10 µm to about 120 µm were placed in blood samples with a sample thickness of about 120 µm on glass slides and subjected to PT and PA imaging. FIG. 23 is a summary of the negative contrast of the collagen-induced aggregates, expressed as a percent reduction of the PA signal relative to the baseline signal levels from the surrounding blood cells. As summarized in FIG. 23, the PA and PT signal amplitudes were dependent on the size of the aggregates. The negative contrast resulted in signal levels that were discernable from the background signal from the surrounding red blood cells for aggregates as small as 20 µm.

The results of this experiment demonstrated that platelet aggregates were detectable within the background signal produced by surrounding blood cells using the negative contrast of the PA and PT signals produced by the platelets relative to the corresponding signals produced by the surrounding blood cells. Further, the magnitude of the negative contrast was related to the size of the platelet aggregate.

Example 20. Detection of the Structure of Heterogeneous Blood Clots In Vitro Using the PAFC System To demonstrate the ability of the PAFC system to detect the structure of heterogeneous blood clots, the following experiments were conducted.

Blood samples were obtained, and collagen was added to the blood samples to induce the formation of a heterogeneous clot, as described in Example 19. Optical images and PT/PA scans of the clot were obtained using the equipment and methods described in Example 19.

FIG. 24A is an optical image of the heterogeneous blood clot formed in a whole blood sample, and FIG. 24B is the corresponding photoacoustic signal pattern from the PA scan of the sample. As shown in FIG. 24B, the relatively high density of red blood cells in the outer layer of the clot was characterized by a distinct increase in the magnitude of the PA signal above background levels (positive contrast), and the relatively high density of platelets in the center of the clot is characterized by a distinct decrease in the magnitude of the PA signal below background levels (negative contrast).

The results of this experiment demonstrated the feasibility of identifying the structure of aggregations of red blood cells and platelets using the PAFC system.

Example 21. In Vivo Detection of Circulating Platelet-Rich Clots in Rat Mesentery Model Using PAFC To assess the feasibility of detecting circulating clots in vivo using the PAFC system, the following experiments were conducted. Photoacoustic and photothermal measurements were conducted in vivo using circulatory vessels in the mesentery of the rat, using a method similar to Example 3 and the PAFC system described in Example 19. The formation of clots in the rats was induced using an intravenous injection of collagen (No. 385 Collagen, Chrono-Log) at a dosage of about 100 µg/kg of body mass.

Figure 25:
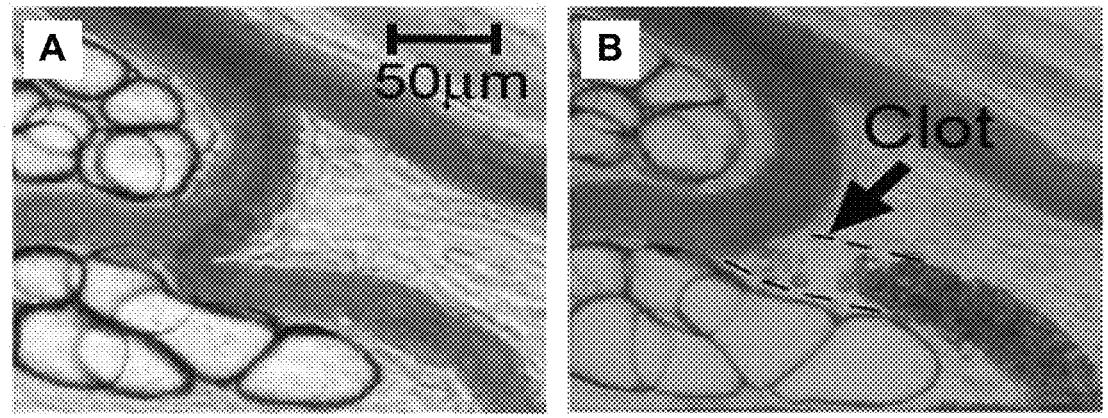
FIG. 25 includes optical images of a rat mesenteric vein before intravenous injection of collagen (FIG. 25A) and after the formation of a collagen-induced clot (FIG. 25B).
Figure 26:
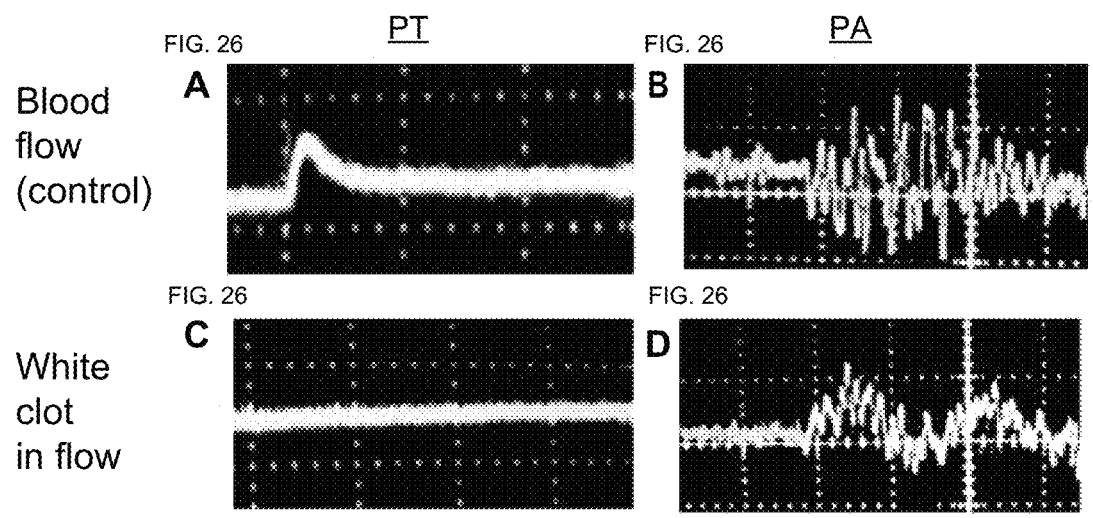
FIG. 26 shows oscilloscope traces of the photothermal signals (FIG. 26A) and photoacoustic signals (FIG. 26B) measured from circulating blood alone, and the photothermal signals (FIG. 26C) and photoacoustic signals (FIG. 26D) measured from circulating blood containing clots. All signals were generated after exposure to 605 nm laser pulses.

Intravenous injection of collagen into the rats (N=3) led to the formation of circulating platelet-rich clots within a few minutes as shown in FIG. 25. FIG. 25A is an optical image of normal blood flow before the formation of a clot (control), and FIG. 25B is an optical image of a clot adhered to the epithelial wall of a mesentery blood vessel. The platelet-rich clots were identified using PAFC; the results are summarized in FIG. 26. FIG. 26A and FIG. 26B are representative photothermal and photoacoustic signal patterns, respectively, detected from blood flow prior to the formation of clots. FIG. 26C and FIG. 26D are representative photothermal and photoacoustic signal patterns, respectively, detected from a circulating clot. The detection of the circulating clot was further verified by comparison to high-speed imaging taken concurrently with the PAFC measurements.

The PA signals from circulating clots were characterized by negative dips in signal magnitude corresponding to a negative contrast. The magnitude of the negative contrast, the duration of the negative dips, and the rate of clot signal detection varied within large ranges of 20%-100%, 10-100 ms and 0.5-3.0 clot/min, respectively, which indicated considerable heterogeneity in clot size, velocity, and concentration (N=6). Some clots were observed to be adhered to the vascular wall about 10-15 min after the collagen injection, as shown in FIG. 25B.

Initially, the adhered clots appeared to be almost transparent structures with no sign of incorporated RBCs. After about 5 minutes of adhesion, single RBCs were incorporated into the clots. The number of RBCs incorporated into the clots then gradually increased over the next 15 minutes of adhesion.

These observations suggested that newly-formed clots circulated as platelet-rich white clots at similar velocities as surrounding RBCs, resulting in minimal collisions and minimal incorporation of RBCs into the circulating white clots. By contrast, the rate of collisions of moving RBCs with static adhered clots increased dramatically, leading to RBCs being stuck in the heterogeneous meshes formed by platelets and fibrin fibers. Although the transformation of white clots into partly red clots led to a decrease of negative contrast in PAFC measurements, the contrast remained sufficiently high for clot detection.

The results of this experiment demonstrated that clots of various compositions were detectable using PAFC visualization methods.

Example 22. In Vivo Detection of Circulating Platelet-Rich Clots in the Mouse Ear Model Using PAFC To assess the efficacy of in vivo detection of collagen-induced clots in a mouse ear model, the following experiments were conducted. PAFC measurements were conducted in vivo to detect clots circulating through capillaries in the ear of a mouse, using methods similar to those described in Example 2 and the PAFC system described in Example 19. The formation of clots in the mice was induced using an intravenous injection of collagen (No. 385 Collagen, Chrono-Log) at a dosage of about 100 µg/kg of body mass.

After collagen injection, real-time monitoring of the collagen-induced circulating clots was performed in each mouse ear (N=3) using PAFC. Because transmission imaging had low resolution due to strong light scattering in the mouse ear tissue, the presence of circulating clots detected by PAFC was verified by labeling the circulating clots with conventional fluorescent dye (CFSE) and performing fluorescent microscopic visualization. Ultra-fast PAFC performed using a high pulse-repetition rate (10 kHz) laser at an pulse wavelength of 532 nm detected circulating clots associated with negative PA signal dips at a detection rate of 1-2 clots/min and negative contrast levels ranging from 12% to 59% of the mean background PA signal levels, as shown in FIG. 27. A thromboembolism was later found in the lungs of the mice, consistent with previously published studies of collagen-induced clots.

The results of this experiment demonstrated that blood clots circulating through capillaries beneath pigmented mouse skin were detectable in vivo using the PAFC system.

Example 23. In Vivo Detection of Circulating Clots in a Mouse Carotid Artery Using PAFC To assess the efficacy of in vivo detection of clots circulating in a mouse carotid artery, the following experiments were conducted. PAFC measurements were conducted in vivo to detect clots circulating through the carotid arteries of nude mice similar to those described in Example 2 and using the PAFC system described in Example 19. The formation of clots in the mice (N=3) was induced using an intravenous injection of ferric chloride, which caused collagen release and platelet activation followed by the formation of initially platelet-rich white clots that transformed over time into heterogeneous red thrombi. A gradual decrease in PA signal variation from the carotid arteries was detected over the first 5 minutes following the injection of the ferric chloride. This decrease was associated with clot formation and accompanied by changes in the shape and the width of PA signals. FIG. 28A shows a representative PA signal taken from normal blood flow through the carotid artery prior to injection, and FIG. 28B shows a representative PA signal taken from the carotid artery after total occlusion of blood flow by a clot. Over time rare transient PA signals with a specific set of positive and negative contrasts were found in circulation, that were likely related to detached fragments of the carotid thrombus circulating as moving clots. FIG. 28C shows a PA signal from a circulating clot detected in a skin circulatory vessel of the mouse.

The results of this experiment demonstrated that blood clots forming within a carotid artery were detectable in vivo using the PAFC system.

Example 24. In Vivo Detection of Circulating Clots in Presence of Circulating Tumor Cells Using Two-Color PAFC To assess the in vivo detection of collagen-induced clots in the presence of circulating tumor cells (CTCs) in a simulated flow, the following experiments were conducted. PAFC measurements were conducted to monitor the blood circulating through a mouse ear vessel using PAFC methods similar to those described in Example 22.

Breast tumor cells (MDA-MD-231) were labeled by gold nanorods having a maximum absorption near 670 nm, using methods similar to those described in Example 10. The labeled breast tumor cells were intravenously injected into the mice. The formation of clots in the blood flow of the mice was induced by intravenous injection of collagen into the mice (N=6).

Previous in vitro observation of the formation of clots in mouse or human blood spiked with tumor cells in an artificial flow device (not shown) exhibited the rapid formation of clots within a short time (5±1.5 min) after collagen injection. The clots were observed to be aggregates of platelets, microparticles, tumor cells and leukocytes that varied in composition and size. Unexpectedly, about 20-30% of the clots contained CD44 markers associated with the most aggressive population of cancer stem cells (data not shown). Approximately 10% of these clots included CD45 marker associated with leukocytes (data not shown).

After the injection of collagen, two-color PAFC conducted using laser pulses at 532 nm and 671 nm was used to monitor the blood flow through a mouse ear vessel, using a two-color PAFC method similar to the method described previously in Example 10. A representative sample of the photoacoustic signals detected by the PAFC system induced by 532 nm and 671 nm excitatory pulses is presented in FIG. 29. The PA signals generated by the 532 nm excitatory pulse exhibited several sharp drops in signal magnitude that were associated with the detection of clots containing platelets. However, several unique patterns of PA signals were detected during PA monitoring that were associated with particular circulating structures.

Examples of these PA signal patterns are highlighted as inset graphs in FIG. 29. A negative contrast in the PA signal produced by the 532 nm pulse accompanied by no change in the PA signal produced by the 671 nm pulse indicated the detection of a clot that included mostly platelets (left inset). Negative contrast at 532 nm detected simultaneously with a positive contrast in the PA signal produced by the 671 nm pulse indicated the detection of a CTC-platelet clot complex (center inset). The detection of positive contrast at 671 nm without a simultaneous negative contrast at 532 nm was associated with the detection of circulating tumor cells not associated with clots (right inset).

The results of these experiments indicated that high resolution multicolor PAFC may be used to distinguish the composition, size, and concentration of clots in vivo by analyzing PA signal shapes, widths, and rates of signal detection, respectively.

Example 25. Signal Processing of PA Signals from Clots Detected Using PAFC

To assess the effect of signal processing techniques such as frequency filtering and data averaging on the PA signal patterns used to detect clots in circulation, the following experiments were conducted.

PA signals were obtained in vivo from circulating mouse blood containing moving clots, using methods similar to those described in Example 22. The PA signal was processed through a high pass filter with a cutoff frequency of 100 Hz. The effect of frequency filtering the PA signal data through the 100 Hz high pass filter is illustrated in FIG. 30. FIG. 30A is a graph showing a representative sample of the pre-filtered PA signals recorded over a three-minute period. The pre-filtered signals exhibit oscillations having a variety of characteristic frequencies. Superimposed on this oscillating signal are two pronounced negative PA signal dips produced by clots at recording times of about 680 seconds and 760 seconds. Much of the lower-frequency oscillations observed within this recorded PA signal are likely artifacts introduced by movements of the animal's blood vessel due to the animal's pulse or breathing. FIG. 30B is a graph showing the same series of PA signals after processing through the 100 Hz high pass filter. The high pass filter eliminated the lower frequency oscillations below 100 Hz within the data, but retained the pronounced negative dips associated with the detection of clots at both recording times. The PA negative contrast dips consisted predominantly of high frequency signal components in the range of 100 kHz to about 5 MHz.

To assess the effect of data averaging, recorded PA signal data were subjected to a 100 Hz high pass filter to minimize the lower frequency oscillations as described above. The filtered PA signals produced from consecutive pulses of the 10 kHz laser of the PAFC were averaged in increasingly large groups ranging from no averaging (N=0) to averaging the PA signals of 1024 consecutive laser pulses (N=1024).

FIG. 31 summarizes the effect of signal averaging on a PA signal pattern that included a negative contrast dip resulting from the detection of a blood clot. Because a high laser pulse rate of 10 MHz was used to obtain these data, the signal-to-noise ratio of the PA signals was much higher due to the detection of multiple PA signals from the same blood components induced by multiple consecutive laser pulses. As shown in FIG. 31A, signal noise overwhelms the negative contrast dip detected at about 757.5 seconds. Signal averaging over 16 PA signals (FIG. 31B), 64 PA signals (FIG. 31C), 256 PA signals (FIG. 31D), and 1024 PA signals (FIG. 31E) reduced the signal-to-noise ratio, and enhanced the detection of the negative contrast dip at 757.5 seconds.

The results of this experiment demonstrated that signal processing of PA signal data using methods such as high pass filtering and data averaging resulted in enhanced detection of negative contrast dips and enhanced the sensitivity of the PAFC system for the detection of circulating blood clots.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

REFERENCES

1. Ara, G. Anderson, R. R., Mandel K. G., Ottesen, M, Oseroff, A. R., (1990), "Irradiation of pigmented melanoma cells with high intensity pulsed radiation generates acoustic waves and kills cells." *Lasers Surg Med* 10:52-59.
2. Kim, J. W., Kotagiri, N., Kim, J. H., and Deaton, R, (2006), "In situ fluorescence microscopy visualization and characterization of nanometer-scale carbon nanotubules labeled with 1-pyrenebutanoic acid, succinimdylester." *Appl. Phys. Lett.* 88: 213110.
3. D. O. Lapotko and V. P. Zharov (2005). "Spectral evaluation of laser-induced cell damage with photothermal microscopy," *Laser Surg. Med.* 36:22-33.
4. H. Liao and J. H. Hafner (2005). "Gold nanorod bioconjugates," *Chem. Mater.* 17:4636-4641.
5. Weight, R. M., Viator, J. A., Dale, P. S., Caldwell, C. W., Lisle, A. E. (2006), "Photoacoustic detection of metastatic melanoma cells in the human circulatory system." *Opt Lett.* 31: 2998-3000.
6. V. P. Zharov and D. O. Lapotko (2005). "Photothermal imaging of nanoparticles and cells (review)," *IEEE J. Sel. Topics Quant. Electron.* 11:733-751
7. Zharov, V. P., Galanzha, E. I., Tuchin, V. V. (2006), "In vivo photothermal flow cytometry: imaging and detection of individual cells in blood and lymph flow." *J Cell Biochem.* 97:916-932.

What is claimed is:

1. A method for continuous monitoring of a circulatory vessel of a living organism, the method comprising:
    pulsing circulating target objects comprising red blood cells and at least one clot within the circulatory vessel with at least one pulse of laser energy at a first pulse wavelength ranging between 400 nm and 2500 nm, wherein the first pulse wavelength induces a photoacoustic signal from the circulating target objects, wherein the at least one clot is a red blood cell-rich red clot, a platelet-rich white clot, or a combination thereof and wherein the blood cell-rich clot is light absorbing and the platelet-rich white clot is non-absorbing;
    obtaining a photoacoustic pattern induced by the at least one pulse of laser energy, wherein the photoacoustic pattern comprises at least one photoacoustic signal comprising a blood background signal produced by the red blood cells;
    simultaneously obtaining fluorescence, scattering, and photothermal signals from the target objects, via a photodetector;
    analyzing a combination of the photoacoustic pattern and the fluorescence, scattering, and/or photothermal signals to determine the presence of the at least one clot, wherein analyzing the photoacoustic pattern comprises determining the presence of positive and negative contrast peaks in the photoacoustic pattern, wherein the negative contrast in the photoacoustic pattern below the blood background signal indicates the presence of the white clot, the positive contrast in the photoacoustic pattern above the blood background signal indicates the presence of the red clot, and a combination of positive contrast and negative contrast indicates the presence of a combination of red and white clots; and
    producing a detection signal when the photoacoustic pattern and the fluorescence signal, scattering signal, photothermal signal, or combinations thereof indicates a clot.

2. The method of claim 1, wherein the positive and negative contrast peaks are a sharp increase or reduction in the magnitude of the photoacoustic signals compared to the blood background signal.

3. The method of claim 1, wherein the first pulse wavelength ranges from 500 nm to 600 nm.

4. The method of claim 1, wherein the photoacoustic pattern comprises a series of photoacoustic signals induced by a series of consecutive laser pulses at the first pulse wavelength.

5. The method of claim 1, further comprising administering a contrast agent to increase contrast of the photoacoustic pattern, the fluorescence signal, the scattering signal, and/or the photothermal signal.

6. The method of claim 5, wherein the contrast agent is a fluorescent, scattering, or photothermal signal contrast agent.

7. The method of claim 5, wherein the contrast agent comprises indocyanine green, FITC, evans blue, lymphzurin, magnetic nanoparticles, gold nanoparticles, and/or microbubbles.

8. The method of claim 5, wherein the contrast agent is functionalized with antibodies for targeting, detection, and destruction of the at least one clot.

9. The method of claim 1, further comprising initiating a clot treatment in response to the detection signal, wherein the clot treatment comprises pulsing the clot with a high-intensity laser pulse to destroy the at least one red clot or at least one white clot with the contrast agent.

10. The method of claim 1, wherein the at least one clot further comprises circulating tumor cells, dye, nanoparticles, or microbubbles.

11. The method of claim 1, further comprising:
    pulsing the target objects within the circulatory vessel with at least one additional pulse of laser energy at a second pulse wavelength; and
    obtaining a second photoacoustic, fluorescence, scattering, and/or the photothermal pattern comprising at least one additional photoacoustic, fluorescence, scattering, and/or the photothermal signal.

12. The method of claim 11, further comprising determining the velocity of the at least one clot using the signal duration of the photoacoustic pattern, the frequency shift of the photoacoustic pattern, or the time delay between the first photoacoustic pattern and the second photoacoustic pattern produced by a single clot pulsed by the at least one pulse of laser energy at the first pulse wavelength and the at least one additional pulse of laser energy at the second pulse wavelength applied at a known separation distance.

13. A device for continuous monitoring of a circulatory vessel of a living organism, comprising:
    an in vivo flow cytometer, wherein the in vivo flow cytometer comprises:
        a pulsed laser configured to pulse target objects comprising light absorbing at least one red blood cell-rich red clot and/or at least one non-absorbing platelet-rich white clot within the circulatory vessel with a plurality of laser pulses at a pulse wavelength ranging between about 400 nm and about 2500 nm;

an ultrasound transducer configured to receive photoacoustic signals emitted by the target objects in response to the laser pulses and generate an output;

a photodetector configured to receive fluorescence, scattering, and/or photothermal signals emitted by the target objects;

an optical module configured to convert the wavelength, pulse rate, or both wavelength and pulse rate of the laser pulses emitted by the pulsed laser to desired values; and a processor configured to:

receive the output from the ultrasound transducer and the fluorescence, scattering, and/or photothermal signals from the photodetector, wherein the output comprises a photoacoustic pattern; and analyze a combination of the photoacoustic pattern, the fluorescence signal, the scattering signal, and/or the photothermal signal to determine the presence of the at least one red clot and/or at least one red clot, wherein analyzing the photoacoustic pattern comprises determining the presence of positive and negative contrast peaks in the photoacoustic pattern, wherein the negative contrast in the photoacoustic pattern below a background photoacoustic signal indicates the presence of the white clot, the positive contrast in the photoacoustic pattern above the background photoacoustic signal indicates the presence of the red clot, and a combination of positive contrast and negative contrast indicates the presence of a combination of red and white clots.

14. The device of claim 13, wherein the target objects further comprise a contrast agent to increase contrast of the photoacoustic pattern and/or the fluorescence signal.

15. The device of claim 14, wherein the contrast agent is a fluorescent, scattering, and/or photothermal contrast agent.

16. The device of claim 14, wherein the contrast agent comprises indocyanine green, FITC, evans blue, lymphzurin, magnetic nanoparticles, gold nanoparticles, and/or microbubbles.

17. The device of claim 14, wherein the contrast agent is functionalized with antibodies for targeting, detection, and destruction of the at least one clot.

* * * * *